US008637046B2

(12) United States Patent
Osterrieder et al.

(10) Patent No.: US 8,637,046 B2
(45) Date of Patent: Jan. 28, 2014

(54) BOVINE HERPES VIRUS-1 COMPOSITIONS, VACCINES AND METHODS

(75) Inventors: Nikolaus Osterrieder, Potsdam (DE); Benedikt B. Kaufer, Berlin (DE); Gopinath Raju Seetharaman, Larchwood, IA (US); Richard Harland, Calgary (CA); Lee David Albee, II, Larchwood, IA (US); Mayur Navnitbhai Patel, Larchwood, IA (US)

(73) Assignees: Cornell University, Ithaca, NY (US); Novartis AG, Basel (CH)

( * ) Notice: Subject to any disclaimer, the term of this patent is extended or adjusted under 35 U.S.C. 154(b) by 191 days.

(21) Appl. No.: 13/121,566

(22) PCT Filed: Oct. 1, 2009

(86) PCT No.: PCT/US2009/059196

§ 371 (c)(1), (2), (4) Date: Oct. 12, 2011

(87) PCT Pub. No.: WO2010/039934
PCT Pub. Date: Apr. 8, 2010

(65) Prior Publication Data

US 2012/0034262 A1 Feb. 9, 2012

Related U.S. Application Data

(60) Provisional application No. 61/195,102, filed on Oct. 3, 2008.

(51) Int. Cl.
*A61K 39/295* (2006.01)

(52) U.S. Cl.
USPC .................. 424/201.1; 424/202.1; 424/229.1; 424/265.1

(58) Field of Classification Search
None
See application file for complete search history.

(56) References Cited

U.S. PATENT DOCUMENTS

| | | | | |
|---|---|---|---|---|
| 5,593,873 | A | 1/1997 | Cochran et al. | |
| 5,998,174 | A * | 12/1999 | Glorioso et al. | 435/91.4 |
| 6,410,033 | B1 | 6/2002 | Cochran | |
| 7,063,851 | B2 * | 6/2006 | Coffin | 424/199.1 |

FOREIGN PATENT DOCUMENTS

| | | | |
|---|---|---|---|
| WO | 2004/017990 | A1 | 3/2004 |
| WO | 2005/092374 | A2 | 10/2005 |
| WO | 2007/085962 | A2 | 8/2007 |
| WO | 2007/117303 | A2 | 10/2007 |

OTHER PUBLICATIONS

Watanabe et al (Virology 357:186-198, 2007).*
Koppers-Lalic et al (Journal of General Virology 82:2071-2081, 2001) (in IDS).*
Oosten et al (International Immunology 19:1115-1122, 2007).*
Liang et al (Vaccine 15:1057-1064, 1997).*
Schwyzer et al (Journal of General Virology 75:1703-1711, 1994).*
Taylor et al (Journal of General Virology 79:1759-1767, 1998).*
Koppers-Lalic, D., Immune Evasion by Varicelloviruses: the Identification of a New Family of TAP-inhibiting Protein, Doctoral Thesis, Chapter 9, Summary and Discussion, 2007.
Jones, C., et al., "A review of the biology of bovine herpesvirus type 1 (BHV-1), its role as a cofactor in the bovine respiratory disease complex and development of improved vaccines," Animal Health Research Reviews, vol. 8, No. 2, Dec. 2007, pp. 187-205.
Koppers-Lalic, D., et al., "The UL41-encoded virion host shutoff (vhs) protein and vhs-independent mechanisms are responsible for down-regulation of MHC class I molecules by bovine herpesvirus 1," Journal of General Virology, vol. 82, No. 9, Sep. 2001, pp. 2071-2081.
Kaashoek, M.J., et al., "Virulence, immunogenicity and reactivation of bovine herpesvirus 1 mutants with a deletion in the gC, gG, gI, gE, or in both the gI and gE gene," Vaccine, vol. 16, No. 8, May 1, 1998, pp. 802-809.
Van De Walle, G., et al., "Alphaherpesviruses and Chemokines: Pas de Deux Not Yet Brought to Perfection," Journal of Virology, vol. 82, No. 13, Jul. 2008, pp. 6090-6097.
Koppers-Lalic, D., et al., "Varicellovirus UL49.5 Proteins Differentially Affect the Function of the Transporter Associated with Antigen Processing, TAP," PLOS Pathogens, vol. 4, No. 5, May 2008, p. e1000080.
Fraefel, C., et al., "Identification of the Bovine Herpesvirus 1 circ Protein, a Myristylated and Virion-Associated Polypeptide Which is Not Essential for Virus Replication in Cell Culture," Journal of Virology, vol. 68, No. 12, Dec. 1, 1994, pp. 8082-8088.
Van Drunen Littel-Van Den Hurk, S., Cell-mediated immune responses induced by BHV-1: rational vaccine design, Expert Review of Vaccines, Jun. 1, 2007, vol. 6, No. 3, pp. 369-380.

* cited by examiner

*Primary Examiner* — Mary E Mosher
(74) *Attorney, Agent, or Firm* — Hodgson Russ LLP

(57) ABSTRACT

The disclosure relates generally to the treatment or prevention of disease in cattle. More particularly, the invention is directed to the production and use of modified bovine herpesvirus 1 (BHV-1) and their use in compositions and vaccines that protect cattle from BHV-1 infection while not suppressing the immunological response in the host. In one example, the invention is directed to the use of modified BHV-1, administered with additional immunogens, either through co-administration and/or through administration in combination vaccines, and the use of these vaccines for the protection of cattle from disease. In one example, use of the modified BHV-1 in the administered compositions facilitates an immune response to or against the additional immunogens.

13 Claims, 51 Drawing Sheets

Cooper Strain BHV-1 UL49.5

Figure 10:
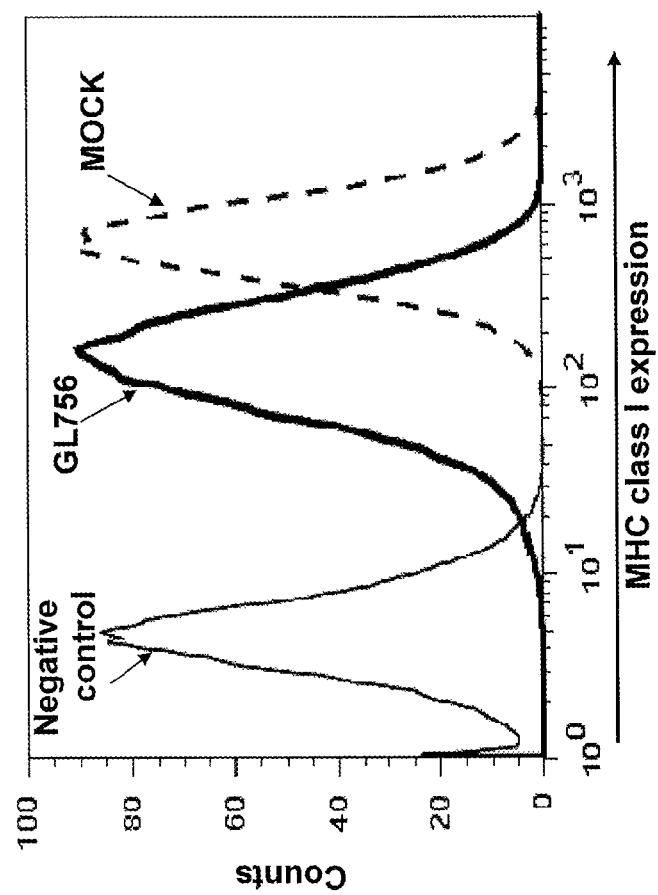

DNA (SEQ ID NO:1)
ATGCCGCGGTCGCCGCTCATCGTTGCGGTTGTGGCCGCCGCGCTGTTTGC
CATCGTGCGCGGCCGCGACCCCCTGCTAGACGCGATGCGGCGCGAGGG
GGCAATGGACTTTTGGAGCGCAGGCTGCTACGCGCGCGGGGTGCCGCTC
TCGGAGCCACCGCAGGCCCTGGTTGTTTTTACGTGGCCCTGACCGCGG
TAATGGTCGCCGTGGCCCTGTACGCGTACGGGCTTTGCTTTAGGCTCATG
GGCGCCAGCGGGCCCAATAAAAAGGAGTCGCGGGGGCGGGGCTGA

Amino Acid (SEQ ID NO:2)
MPRSPLIVAVVAAALFAIVRGRDPLLDAMRREGAMDFWSAGCYARGVPLS
EPPQALVVFYVALTAVMVAVALYAYGLCFRLMGASGPNKKESRGRG

Figure 1

Cooper Strain BHV-1 UL41

DNA (SEQ ID NO:3)

ATGGGGCTCTTCAAGCTACTGCGTTACGCGTACGGCAATCGGCTGGTAAA
GCACGACGCCATCACCACGCCGCCGGGCGTGATGACCCCGATCGCGGTCG
ACCTGTGGAACGTGATGTATACGCTCCTGGAGCGCTTCTGCGGCGACGCG
CCCGGCGGCGTAGGAGACGCCGCCGCGACCGCGCGCTGCTTCCTCTCGCT
GCTGCGGATGCTGCTCAAGCGCTCCTACTACCCGATCTTTGTAGCGGACCG
CGGCATCCACGGGGACCGGCGCGCCACGCGGGGTGCCAAGGCCATTGTGG
CGCAGACGATGCGCGCCGTCGGCGGCTCGGGCCGCCTCGGGCGGCTCGTC
AGCGACGATTATACCTCGGAGGACGAGGTGCTGGGCGCGTACGAGTACCC
CGTCCCGCACGCGGACGCGGCAGCCGACGACGACGAGGAGGCAACGGCG
AAGGAATTTGCCGGGCGCGCCTCGGCGGGGGCCGCGCGGGCCAACGCGCC
CAAGCTGGCACATCGCGTGTGCGTGAGCCTCATCCGCTTTTTGGGCTACGC
GTACGTCGACGCCGCTGAGATGGAGGCAGACGACGTCTGCGCAAACCTCT
TCCACACAAACACCGTGGCGCACATCTACACGACGGACACGGACATGATC
CTTATGGGCTGTGACCTGATTTTGGACGCGGCGCCGTTGTTCC

Figure 2-1

```
CCCCGACGCTACGCTGCCGCGACGTGCTGGGCTGGGCTCACGTA
CGGCCAGTTCCTCGGACGTTCGTGCCGCTGCCACACGACTGCACCAG
CCGCCAATGCTGCGCTCGGTGCAGGTGGCGGGGGTGCCGGCGCG
CTGCCGAGGCCGAGCCCGACTACCGAGACGGAGTCTGGCTCCGAGCG
CGAGCCGGAGTCCGAGTCGGTCCGGGCCGCTGGGCCGGGGCCGG
TTGCCCGCCCGGTCGACGCCGCTGAAAACTACGACGCGGACCG
TGGAAGCGCACAGGCGTGCCGCATGAAGTATACATCTCGGTACCCTCCGAT
TGCGCAGACGTGCGCGACGCGCTGCTGCCGGCGTCCCAGACG
CGCGGGCGGCGTGCTGGAGCGCAAATTGTAAAGCACGTGGTGGACACG
ATCGGGCGCGAATGCGGGGCGCTGGGCCGTGAAGCGGTGCCCA
TCGCACAGGACCCCCGACCCTCGGCTCGTGTACGACACCATCGTGAG
CGCCGTAGGCAGGCCCGCGAGGCCGACACGCTGATGGGCTCTCTGG
AAGCACACATCCCCACTCCACCCCCATTTGCCAAGGTGCTGGCAGACTACT
GGGACGAGGCCCCGGGGTCGCGACGGACGGCAACCCGGCCAAT
AA
```

Figure 2-2

Amino Acid (SEQ ID NO:4)

MGLFKLLRYAYGNRLVKHDAITTPPGVMTPIAVDLWNVMYTLLERFCGDA
PGGVGDAAATARCFLSLLRMLLKRSYYPIFVADRGIHGDRRATRGAKAIVA
QTMRAVGGSGRLGRLVSDDYTSEDEVLGAYEYPVPHADAAADDDEEATA
KEFAGRASAGAARANAPKLAHRVCVSLIRFLGYAYVDAAEMEADDVCAN
LFHTNTVAHIYTDTDMILMGCDLILDAAPLFPPTLRCRDVLASLGLTYGQF
LATFVRCHTDLHQPPMLRSVQQVVRGLRRAAEAEPATTETESGSEREPESEL
GRPGAGPRRRLPPAVDDPLKTTTPATVEAHSVRMKYTSRYPPIAQTCADAL
RLLPASQTRGGVLERKFVKHVVDTIAPRMRGRWAVLKRVPIAQDAPDPRL
VYDTIVSAVGSAAEADTLMGLFWKHIPTPPPFAKVLADYWDEAPAGPGSRR
TTRQ

Figure 2-3

Cooper Strain BHV-1 Circ

DNA (SEQ ID NO:5)

ATGGGTGCCCGCGCCTCCGCGCCTGCTGCCGGCCCGCCCCCAGCCCACG
CTGTTCTACTAGATGCGCTCTCCGGGGGCACGATTGACCTGCCTGGCGGC
GACGAGGCCGTCTTTGTGTCCTGCCCGACGACGCGCCCCGTGTACCACC
ACATGCGCCGCGGCCGCACGGCCCACACTACACCCGTGCACTTCGTTGG
CCGCGCCTATGCCATCTTGCCCTGCCGCAAGTTTATGCTGTATCTGATGC
GCGGTGGTGCCGTTTACGGCTACGAGCCCACCACTGGCCTGCACCGCCT
CGCCGATTCACTGCACGACTTTCTTACTACTGCCGGACTACAGCAGCGAG
ACCTACACTGCCTCGATGTCACGGTGCTTGACGCGCAGATGGACCCGGT
GACGTTCACCACCCCCGAGATCCTCATCGAGCTCGAGGCGGACCCGGCC
TTCCCACCGCCGCCCTCGGCCCGCGCGCCGCTCCACGCTGCGCCGGG
CGTCTATGCGCCGGCCCGCACGCACCTTCTGCCCCCACCAGCTGCTAGCA
GAGGGCTCCATTCTGGACCTCTGCTCGCCAGAGCAAGCGGCGGCGCCGG
GCTGTTCGCTGCTCCCCGCCTGTGACTCTGGAGACGCCGCGTGCCCCTGC
GACGCTGGCGAGACCGCCCGTGACTGTACTGCCGATGC

Figure 3-1

CGCGGCGGCTCCCAGCCCCCGGCGCCTTATCTCGCTATAGCTCCGTGCGCTCGGGTGTTCTTTTAG

Figure 3-2

Amino Acid (SEQ ID NO:6)

MGARASAPAAGPPPAHAVLLDALSGGTIDLPGGDEAVFVSCPTTRPVYHH
MRRGRTAHTTPVHFVGRAYAILPCRKFMLYLMRGGAVYGYEPTTGLHRLA
DSLHDFLTTAGLQQRDLHCLDVTVLDAQMDPVTFTTPEILIELEADPAFPPPP
SARARRSTLRRASMRRPARTFCPHQLLAEGSILDLCSPEQAAAPGCSLLPAC
DSGDAACPCDAGETARDCTADAARAPSPGALSRYSSVRSVFF

Figure 3-3

Cooper Strain BHV-1 LR-ORF1

DNA (SEQ ID NO: 7)

ATGGGCGTCGGCTGGCCTTCTCTCCCGGCCGGGGTTGCCATTGCGCGACC
TCGGCCCGGCGGCTCCGGCCAGGGCCGGAGCGCCGGCCCGCCGGGGTC
GGCGGCAGGGGCCGGGACGGGAGACGGGTCGGGTCGGGTGGAA
ATAGCCGCGGCTGTGCTGAGCCGCGGTAACAGCGGCTCGGCGC
CGAGCTCCGAGCGACGGAAGGTGCCGGGCAGTTACTGCCGCCG
CCGCGGGCGGGGTCCCAATTGCGCACCCGCGAGGCCGGCCGGGGCC
GCCGGGGCCGGGTCGGGAGGGGGCGGGGCGGTCGCCGTCAGGTC
TATCACTGTGGAGATGGGCGGGGGGGGTGGGCCGGGCCGGGGG
TCGGGGCGGGTCTAACTCTGTCCTTCTCTCCGGGGCCTGCACACGGG
GAGGCCAGCTCCCCGAGCAGCCTGGCCTCCCCTCGTCCCTCCT
CACTGCCCCAGCCCCCCAGCCCGGTCTCCCGGACTCCCAAGCCCG
CTCCCTCCCTCTCTGGGCTGCATGCGGGCTGCGGCCGC
GGGGCTGCCGCGGCCGCCGGCAATCGGGGTCTCGTCTCCCGCGC
GGCTCCGAGAGCTGGGGCGCGAAACTGCCGCGGCCGCAAGGG
CGGGCGCGTAGCGACCGGAGGCGCCGGCTGCACCGCGGGT

Figure 4-1

GTTTGTCGACCCTCTAGTGCTGACATACTGTCTTTCCGCAGGCCGCCGAGC
CCGGGGCCGGCCAGACGCCAGAGCCCCCGCGTGCCGCCTGACTCAACCTCCGCG
TCCGTCTCCGGCTTCCGTTCCGTCGTCGTCAATGGCGGTCAGGTCGGAGGT
GCTGAGCCCGACGACGACTCTTCTGACTCCGACCAAGAGTCGTCCTCC
GAGCCCTCCGAGTCCGAGTCCGAGGTGTCGAGAAACACCACCCCACGGC
CGCCAGGAGGCGCAGACTGCTGA

Figure 4-2

Amino Acid (SEQ ID NO: 8)
MALAGLLSRPGLPLRPTSARAAPARAGAPARRGSAAGARPAGDGVGARVEI
AAAVLVAAVTAGLGAELRATEGAAAAVTAAAAGVPICAPAEAGPGA
AAGAGSAGRAGAFAVRSITVEMGAGAGAGAGAGVGARSNVLLRRACT
RGGPASPSSLARRSPRPSSLPAPQPAVSPAATPKPAPLPSSLGSGLHARACAA
GAARGAAGNRGSRLPPRLRELGGAETAAARPQGRRASDRGAGCTAGVCRP
LVLTYCLSAGRRARAAPDAPRVRLDSTSASVSGSVSVSSMAVRSEVLSPDD
DSSDSDQESSSEPSESESEVSRNTTPRPPGGA

Figure 4-3

Cooper Strain BHV-1 LR-ORF2

DNA (SEQ ID NO: 9)

ATGCGCGACCTGGGCCATAAAAGCCCCGCGCATGCGCGAGCAGTTACTTT
CGGTTTGGGGATGACAGCGGCGACTGCGGCTCGAAAGTTAAGTATGCAG
GCTGGGGGTCGCAAATACACGGCGGTGCGGTGTGGTGGGCTGCGGGTCG
CGGAGTGGGTGGGCGGGGAGCCGGCCGCGGCGATTATTGCCGCCAGGCG
CTGCCGCCGCTGCAGCGGCCGAGCAGCCCGGCCAGGCTCGGGCCCTGGC
GACCGCCTGGCTGCGGCGCCAGGGCCGCGCTGCTGCGGCGGGGGTCCC
CAGGAGGCTTTCTCGCACCCAGGCGGCCACTTCCATTTCGGTGCGCCGCC
TCTTCTGCGCCGAGCTCTCGGGGCCGGGGTCCAGGTCGCCCCGCGCCATG
GCGCTCGCTGGCCTTCTCTCCCGGCCGGGGTTGCCATTGCGGCCGACCTC
GGCCCGGGCGGCTCCGGCCAGGGCCGGAGCGCCGGCCCGCCGGGGGTCG
GCGGCAGGGGCGCGGCCGGCGGGAGACGGGGTCGGGGCTCGGGTGGAA
ATA

Figure 5-1

Amino Acid (SEQ ID NO: 10)
MRDLGHKSPAHARAVTFGLGMTAATAARKLSMQAGGRKYTAVRCGGLR
VAEWVGGEPAAIIAARRCRRCSGRAARPGSGPGDRLAAAPGPRCCGGGSP
GGFLAPRRPLPFRCAASSAPSSRGRGPGRPAPWRSLAFSPGRGCHCGRPRPG
RLRPGPERRPAGGRRQGRGRRETGSGLGWK

Figure 5-2

Cooper Strain BHV-1 Us4

DNA (SEQ ID NO: 11)

ATGCCTGCCGCCCGGACCGGCACCTTGGCCGCCGTCGCCCTAATCCTGCTC
TGCGGGGCCGCCGTTTTGGGGCGCCCCGCGCCCGACGACCTCTGTTTCGCC
GACGTGCGCCGCACTGGCATGGCGCCCTCCCGCCCGCTGGGGCCCGTCCTG
AACCTAGCGGCCTCGGATTTGACCTCGCGGGTTTCGGTGCGCGCGGTGGAC
GCTTCGCGCGGCTGCGCCCTGGCCCTCTTGGACATGGCGGAGACGGTGGTG
CCCGGCGGACCGCGAGCCGCCGACGTCGTCGACGTCGGCTGGGCTTACCA
AGACGGGGACTGCATGGTGCCTCTGGCATATCGCCAGTACTTTAACTGCAC
GGGGGGCGCGCTGCCCGGCCAAAACGTCTGCGCCGGGCTCTCTGAGACCC
GCATCCGCGGTGGCTTTGGAACCTCCGACTACGCGCTCTACGGGACGTCGC
TAGTACTGCGCCCCGGCCTGTACGACCGCGGGACCTACATCTACTTCCTTG
GATACGGCCCAGACGACATCTACGTGGGCAGCGTCACGCTCATGGTGGGC
GCCGACATCCACAAATACCCCTGCGGGCTGGACCGAGGGCTCGGTGTGGC
CCTGCACCACAAGAGCGGACCGGCCCGACCTCTGACAGAGGACGACGCCA
CCGGCGACTGGGCCTGCGGCTGCTTCCCCGCCCTTGTTGA

Figure 6-1

```
GGTTGACGCGGGTGTGGGGCAACGTAAGCGCCGCAGAGCTGGGCCTGGCC
GACCCGATCGACTACGCCGACGAAGGGGTGAGGTCGAAGTGCTCGAG
GACGAAGCGGAGCGCCAGGCCAGGGAAACCTGCCGCAGGACGACCCGAC
CCCGACCTCGCAGATTGCCGACGTCGGGCTCTTTAGCGAAAGCGACA
TGTTCCGGACCGCCAGGCCCGAATCGCTGTGATCGGCGCCGTTGC
CAAGGACGTCCTGACGGTGCCCCTCAATCGCCCGGCGCTCTTAC
GAGCCCTGGAAACGCATGGAGTGCTGGAGTGCAACTCCGCCGGGAGA
CCGGGACGCAGGCGGGTGGTGATGTCTCTCCAGGAGCCGCTCGCCT
CGAGCGCCCGCCCCGATGCCCACCGATCCGGAGTTTGGGCTCTTT
GGCCTGCCCGATGACCCCGTGCGGCCATTCTCATCGGCCTCG
CGATCGCTCTGCTGCTGTGTTTCGCTGGTGATCGGCTCGTCTGC
GCCCGCCTCGCCGGCGCCCGGCCAAGGCCAGCCCGACGCCCGGCCG
CCACGTTCGCCAAGAGCAACCCCCGCGTACGAGCCGATGCTCAGCGTCTG
A
```

Figure 6-2

Amino Acid (SEQ ID NO: 12)

MPAARTGTLAAVALILLCGAAVLGRPAPDDLCFADVRRTGMAPSRPLGPVL
NLAASDLTSRVSVRAVDASRGCALALLDMAETVVPGGPRAADVVDVGWA
YQDGDCMVPLAYRQYFNCTGGALPGQNVCAGLSETRIRGGFGTSDYALYG
TSLVLRPGLYDRGTYIYFLGYGPDDIYVGSVTLMVGADIHKYPCGLDRGLG
VALHHKSGPARPLTEDDATGDWACGCFPALVEVDAVWGNVSAAELGLAD
PIDYADEGGEVLEDEAGSASGNLPQDDPPDLADCRTVGLFSESDMFRT
ASGPESLLIGAVAKDVLTVPLNLPPGRSYEALRNASLECNSRPRETGDAAVV
VMSLQEPARLERRPDARATDPEFGLFGLPDDPAVRRGILIGLAIALLVLLFSL
VIVLVCACRLARAAKAARRARAATFAKSNPAYEPMLSV

Figure 6-3

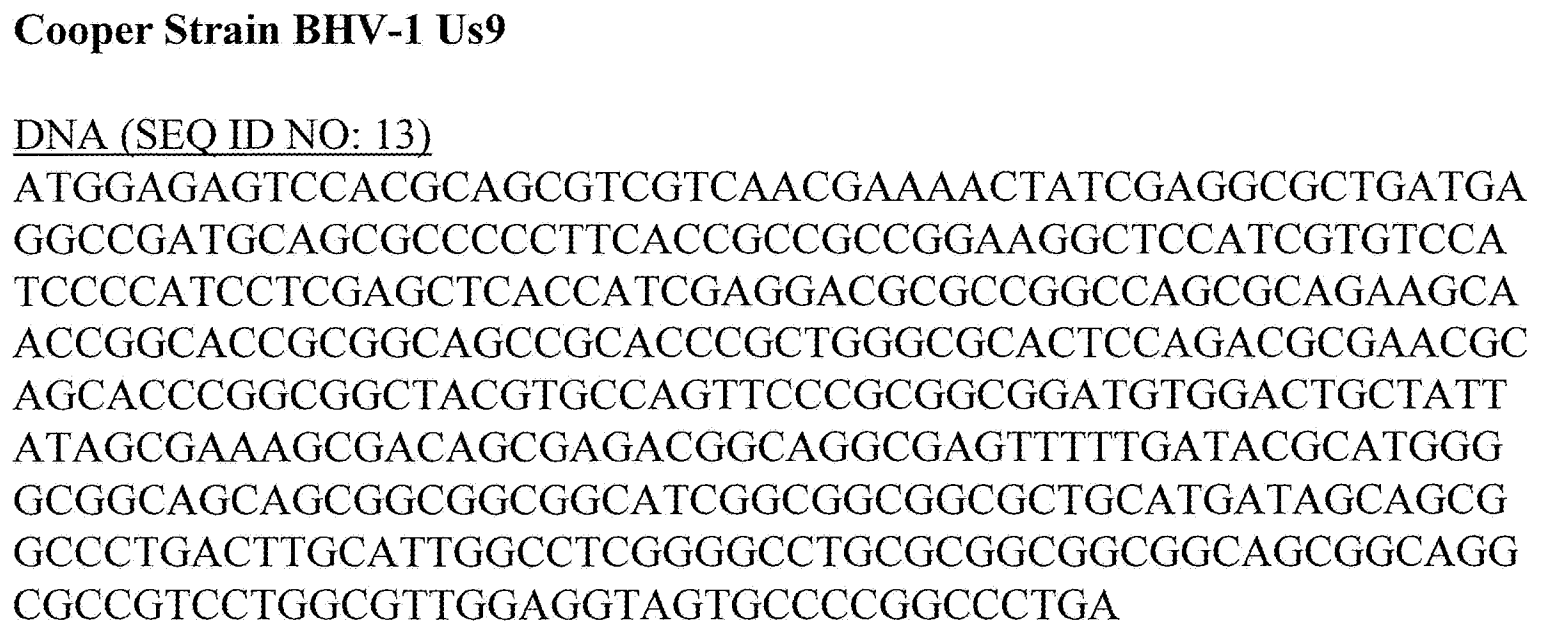

Cooper Strain BHV-1 Us9

DNA (SEQ ID NO: 13)

ATGGAGAGTCCACGCAGCGTCGTCAACGAAAACTATCGAGGCGCTGATGA
GGCCGATGCAGCGCCCCCTTCACCGCCGCCGGAAGGCTCCATCGTGTCCA
TCCCCATCCTCGAGCTCACCATCGAGGACGCGCCGGCCAGCGCAGAAGCA
ACCGGCACCGCGGCAGCCGCACCCGCTGGGCGCACTCCAGACGCGAACGC
AGCACCCGGCGGCTACGTGCCAGTTCCCGCGGCGGATGTGGACTGCTATT
ATAGCGAAAGCGACAGCGAGACGGCAGGCGAGTTTTTGATACGCATGGG
GCGGCAGCAGCGGCGGCGGCATCGGCGGCGGCGCTGCATGATAGCAGCG
GCCCTGACTTGCATTGGCCTCGGGGCCTGCGCGGCGGCGGCAGCGGCAGG
CGCCGTCCTGGCGTTGGAGGTAGTGCCCCGGCCCTGA

Figure 7-1

Amino Acid (SEQ ID NO: 14)
MESPRSVVNENYRGADEADAAPPSPPPEGSIVSIPILELTIEDAPASAEATGTA
AAAPAGRTPDANAAPGGYVPVPAADVDCYYSESDSETAGEFLIRMGRQQR
RHRRRCMIAAALTCIGLGACAAAAAGAVLALEVVPRP

Figure 7-2

Cooper Strain BHV-1 Us8

DNA (SEQ ID NO: 15)

ATGCAACCCACCGCGCCGCCCCGGCGGCGGTTGCTGCCGCTGCTGCTGC
CGCAGTTATTGCTTTTCGGGCTGATGGCCGAGGCCAAGCCCGCGACCGA
AACCCCGGGCTCGGCTTCGGTCGACACGGTCTTCACGGCGCGCGCTGGC
GCGCCCGTCTTTCTCCCAGGGCCCGCGGCGCGCCCGGACGTGCGCGCCG
TTCGCGGCTGGAGCGTCCTCGCGGGCGCCTGCTCGCCGCCCGTGCCGGA
GCCCGTCTGCCTCGACGACCGCGAGTGCTTCACCGACGTGGCCCTGGAC
GCGGCCTGCCTGCGAACCGCCCGCGTGGCCCCGCTGGCCATCGCGGAGC
TCGCCGAGCGGCCCGACTCAACGGGCGACAAAGAGTTTGTTCTCGCCGA
CCCGCACGTCTCGGCGCAGCTGGGTCGCAACGCGACCGGGGTGCTGATC
GCGGCCGCAGCCGAGGAGGACGGCGGCGTGTACTTCCTGTACGACCGGC
TCATCGGCGACGCCGGCGACGAGGAGACGCAGTTGGCGCTGACGCTGC
AGGTCGCGACGGCCGGCGCGCAGGGCGCCGCGCGGACGAGGAGAGGG
AACCAGCGACCGGGCCCACCCCCGGCCCGCCGCCCCACCGCA

Figure 8-1

CGACGACACGGCGGCCCCCGCGGGGCACGGGGCGCTTCCGCTGCT
GCCGTACCACTCCCACGTATACACCCGGGCGATTCCTTTCTGCTATCGG
TGCGTCTGCAGTCTGAGTTTTCGACGAGGCTCCCTTCTGGCCAGCATC
GACTGGTACTTCCTGCGGACGCGGGACTGCGGCTCATCCGCATAT
ACGAGACGTGCATCTTCCACCCCGAGGCACCGGCCTGCCACCCCGC
CGACGCGCAGTGCAGCTTCGCGTCCGTACCGTCCGAGACCGTGTAC
AGCCGGGCTGTACGAGCAGTGCCCCGACCCTGCCGGTCGCTGGCCGC
ACGAGTGCGAGGGGCGCCGGTACGCCCGGTACCTGGCACCTGGGTCC
CGCCAATAACAGGTAGACCTGGTCTTTGACAGGCCACGTGGAAGCTTG
TCCGGGCTTACGTCTTGTGCTGCAGTACAACGGCCACGTGGAAGCTTG
GGACTACAGCCTAGTCGTTACTTCGGACCGTTTGGTGCGGGTCACC
GACCACACGCCCCGAGCCAGCCCGACGCTCCCGAGCCAGGC
CCACCGCTCACCAGCGAGCGGGCGCCCACCGGGCCCCGGCCCT
GGCTGTGTGGTGCTGGGGCGCTTGGACTCGGCGGGAC

Figure 8-2

TGGTGGGCATGCGGCAGCCCCTCGCCGTTCGGGTGTGCGGCGCGCAAG
CCAGAAGGCCACCTACGACATCCTCAACCCTTCGGGCCCGTATACACC
AGCTTGCCGACCAAGAGCCGCTCGACGTTGGTGGTGCCAGTTAGCGACG
ACGAATTTCCCTCGACGAAGACTCTTTGCGGATGACGACAGGACGA
TGACGGGCCCGCTAGCAACCCCCTGGCAATGCCTACGACCTCGCCGGC
GCCCCAGAGCCAACTAGCGGGTTTGCGCGAGCCCCAACGGCACGC
GCTCGAGTCGCTCTGGGTTCAAAGTTTGGTTTAGGACCCGCTTGAAGA
CGATGCCGCCAGGCGGACCCCGGCCGCACCAGATTACACCGTGGTA
GCAGCGGACTCAAGTCCATCCCTCCGCTAG

Figure 8-3

Amino Acid (SEQ ID NO: 16)

MQPTAPPRRRLLPLLLPQLLLFGLMAEAKPATETPGSASVDTVFTARAGAP
VFLPGPAARPDVRAVRGWSVLAGACSPPVPEPVCLDDRECFTDVALDAAC
LRTARVAPLAIAELAERPDSTGDKEFVLADPHVSAQLGRNATGVLIAAAAE
EDGGVYFLYDRLIGDAGDEETQLALTLQVATAGAQGAARDEEREPATGPTP
GPPPHRTTRAPPRRHGARFRVLPYHSHVYTPGDSFLLSVRLQSEFFDEAPFS
ASIDWYFLRTAGDCALIRIYETCIFHPEAPACLHPADAQCSFASPYRSETVYS
RLYEQCRPDPAGRWPHECEGAAYAAPVAHLRPANNSVDLVFDDAPAAASG
LYVFVLQYNGHVEAWDYSLVVTSDRLVRAVTDHTRPEAAAADAPEPGPPL
TSEPAGAPTGPAPWLVVLVGALGLAGLVGIAALAVRVCARRASQKRTYDIL
NPFGPVYTSLPTNEPLDVVVPVSDDEFSLDEDSFADDDSDDDGPASNPPADA
YDLAGAPEPTSGFARAPANGTRSSRSGFKVWFRDPLEDDAAPARTPAAPDY
TVVAARLKSILR

Figure 8-4

GL756 Strain BHV-1 UL49.5 Mutant

DNA (SEQ ID NO:23)
ATGCCGCGGTCGCCGCTCATCGTTGCGGTTGTGGCCGCCGCGCTGTTTGC
CATCGTGCGCGGCCGCGACCCCTAGTAAGCTTTGCTAGACGCGATGCGG
CGCGAGGGGGCAATGGACTTTTGGAGCGCAGGCTGCTACGCGCGCGGG
GTGCCGCTCTCGGAGCCACCGCAGGCCCTGGTTGTTTTTACGTGGCCCT
GACCGCGGTAATGGTCGCCGTGGCCCTGTACGCGTACGGGCTTTGCTTT
AGGCTCATGGGCGCCAGCGGGCCCAATAAAAAGGAGTCGCGGGGGCGG
GGCTGA

Example UL49.5 Recombination Construct (SEQ ID NO: 17)
AAGCTTAAAGAAGGGCACTTCGACGCCCGCCTCTGTCCCGGCGTTTGC
GTCGTCGTCGACGGCGATGAGGCGAGGCAGCGTGGTGGTTAGCCGCG
CGAGCGTCAGCCGCAGCGCAAGCCCGGGAGCGGCCCGCTGCG
CGAGCGGCCCAGACGATGGCGCAAGATCCCGAGTAGCCCGA
GTCGACGATGCCGCCACGGCTGGTGGGCGGGCATGTGTGTGT
CACCCGAGCGCATTGCGACATTATAAATCAGCCGCTATAAAGGAGAGATCCC
GCCGCCTCATGTTTAAGTTAATCAGCCGGCTATAAAGGAGAGATCCC
GACGGGGCTGTTTCATCTCGCTTTGCTGCTGGCGCAATTGGGCCCAG
AGCGCCAGCGAGTCGGCTCACAGCAGCTTTCCAACCGCCAGGGGC
CGCCTCCGCGTTGAGCTCTACGACGAGGATCCCGGTGCGCCGCTCAT
CGTTGCGTTGTGCCGCCGCGCTGTTTGCCATATTAATGATATCCTT
AAGTGATTGACCGCAACGCTGCCGAGTAACTGTATATAAAGCTCGC
GGTCCCGGCCGACCGCTGCCTTTTCGCACTCGGCCCGACCCGCTTTGA
GCTGCACGCCCCGCCGCCCGGCCGACTCGCTTGCCATGGCCCG

Figure 14-2

GTTCCACAGGCCCTCCGAAGACGAGGACGATTACGAGTACGAGCGACCT
TGGGTGCGAGAAACAGCCTCTATGACTACGAGTCCGGCTCGGATGACC
AGTATACGAAGAGCTGCGCGACGAGCGACCCGAGCGAGCG
GGCGGCGAGCCGCTAGCGTCCGTGCGCCAGCGTGCAGCCGTCCAGCC
CGCCGCCCGCGGCCGGATCGAGCCGCGGGACGACCGTAGC
TGCGCCGCCCGCCCGCCCGCTCGAGCAGCCGGGGTCCTCG
CGCCCGCCGAGCTGCGACCCCGTCCGACCCGCCAGCCACGC
GCGGGTCCTCCGGGCGCCGGGGCA

Figure 14-3

Example Us4 Recombination Construct (SEQ ID NO: 18)
AAGCTTCTGGCATACCCGCGGCGCGCTGTTCGACAGCCCCGCGGGCCCGC
AGGGCGAGGACGCCGAGGCATCGGGCCCGACGATCTGGGCGACC
GCGACTGCGCCGGCAGCTGCTCCGCGTGATTCGCGGCTGGCCGTGCA
CGCCGAAGAGTTTCCACCCAGCCCCACTGACCGGCTGACCCGCAACTTC
AAGCCGCCACGCGAGCACGCCGAGAGCCCGCACAGCCCGTACCGCTGC
CTGGGCGTGCTCCGCTGACTTTGACTTTGCGGCGCCCCACCGCGAGCTGGA
TGCTGACCTTTGACTTTCGGCGCCCCACCGCCGGAGCTGTGGA
GCACCCGTCTCGGTGGCCTCGGGTAGCCCGGGGTTCCCGCA
AAACTGAGGCATATAAGGCGGGCACCGGCAAGTTGGCATCCACAC
TTCGCGCTGTGGACACGAGAGCGAACGCGAGCGAACGCGAGCGCAAGC
GCGAGCACACGACTGCGATCATTAATGATATCCTTAAGTCGCCGGCACC
CCACGCGCCCCGACCCCGCCTGTCCCGGTTACAATAAACAGTTATTC
TTACCAACGTTGGTGCGCCTGCGTGTCTATTGCGAGTTAAACCGAG
TGCCCCACCCCAGGCAGGGCGGGGGTTGGGCCGGCCG

Figure 14-4

CAGCCCCGGCTGGGTATATATCCCCGACGGGGACTAGAGATACACTCG
CCCGGCGGGCTGCTGCGAGCGGGGAACATGCAAGGGCCGACATTGG
CCGTGCTGGGCGGCTGCTCGCCCGTTGCGGGTGAGCTTGCCTACACCCGC
GCCGGCGGGGTGACGGTATACGTCGACCCGCGGTACCCGATGCCGGGA
TACAACTACACTGAAACGCTGGCACACTACCGGCCCATACCGTCGCCCT
TCGCAGAGCGCGAGCACATGCTGGCAGCCCGTCGAGGTGCCGTACGGACGAGCG
CGGGGCGTGCCACATGCTGGCTGATCGCAGACCCGCAGGTGGGGC
GCACGCTGTGGGAATCTAGA

Figure 14-5

Example UL41 Recombination Construct (SEQ ID NO: 19)

AAGCTTCTCTCGGCGGGGACGGCCACGTACACTTGCTCGTCGTAGAGGC
CGCTGTGTACCAGCATGCCCTCGCGGCTAAAGACCAAAAAGGCGTTCGC
AGCGAGGCGCCAAAGGGGCTCAGCAGGGGGAGAACGTCCGCCAGCTGGC
GGCCGATAAGCGAGGCGCTCGCAGGCCTTCGTCGGCGCAGATGGAGGG
AGACCGGGGTGAGCGGGCCTTCGTCGGCGCAGATGGAGGG
GGGCTGCAGCATCGCGGGGGGTCGGGGCGCTTCGCTCGCCTCTTA
CGCGCGGTCGCAAAGCGAGTCTGCGCGGCTCTTTATACTG
GGCGGACGCCCCGCAGCGGCAAAACACACTCGGGCCTCAGCGTAT
CAAACGGGACACGTTAAGTTTCGACGCCTATAAGCGGGCGCGCACT
AGGCCTCCCAATGCCGCGCGCGTGTGCGGGCGACCCTGCGAGA
GAGAGATTAATGATATCCTTAAGAAACGCGCATACGCGAGACTGGCTT
TCGTTGACATGGAACATTTTTATTCGCGGGCGTGGGGTGAGAAGGAGGA
GGAAAGGCGCCTGGCAGGGCAGCGGGGTGCCCTACACAGGTCGTT
GATTACGGGTGCCTGTGTAGTTGGTGCTGCGGGCGCTCAAAGAAGT

Figure 15-1

TCGTGTGCTTCTCGGCAGTCATCAGGGCCAAAGGAAAATCGGTCCCAGG
AGGCGGGGTGCCAAACAGAGGAGGCAGCTGGATAGCAGGAGCAGGCG
GTCCGCGCTGTACTCGACGCAGAAATAGCCTCCACGTCAAGTATA
TGACTGCCGCGGGCGCAACCAAATAAACTCGGCTCAATTTCCACG
CTTCGGGAACAGCTCGTAGATGCGGGGCCGGGGCGCTCCCGCC
GAGGTAGTTGTCGAAGATGCAGCACGACGCGGCCGTGTGCACGGCTTCG
TCGCGGCTGATGAGGTCGTTGGTTTGGCACGTCACGACTCTAGA

Figure 15-2

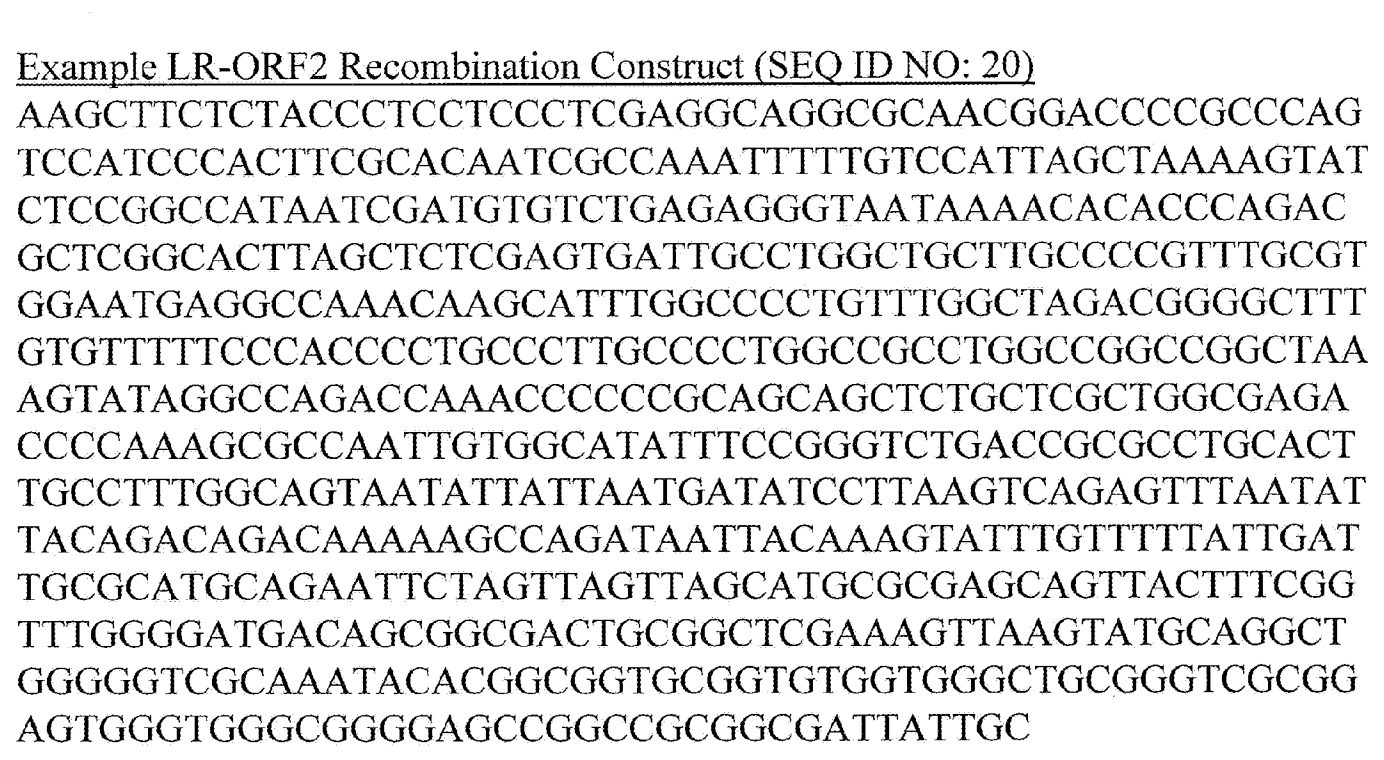

Example LR-ORF2 Recombination Construct (SEQ ID NO: 20)

AAGCTTCTCTACCCTCCTCCCTCGAGGCAGGCGCAACGGACCCCGCCCAG
TCCATCCCACTTCGCACAATCGCCAAATTTTTGTCCATTAGCTAAAAGTAT
CTCCGGCCATAATCGATGTGTCTGAGAGGGTAATAAAACACACCCAGAC
GCTCGGCACTTAGCTCTCGAGTGATTGCCTGGCTGCTTGCCCCGTTTGCGT
GGAATGAGGCCAAACAAGCATTTGGCCCCTGTTTGGCTAGACGGGGCTTT
GTGTTTTTCCCACCCCTGCCCTTGCCCCTGGCCGCCTGGCCGGCCGGCTAA
AGTATAGGCCAGACCAAACCCCCCGCAGCAGCTCTGCTCGCTGGCGAGA
CCCCAAAGCGCCAATTGTGGCATATTTCCGGGTCTGACCGCGCCTGCACT
TGCCTTTGGCAGTAATATTATTAATGATATCCTTAAGTCAGAGTTTAATAT
TACAGACAGACAAAAAGCCAGATAATTACAAAGTATTTGTTTTTATTGAT
TGCGCATGCAGAATTCTAGTTAGTTAGCATGCGCGAGCAGTTACTTTCGG
TTTGGGGATGACAGCGGCGACTGCGGCTCGAAAGTTAAGTATGCAGGCT
GGGGGTCGCAAATACACGGCGGTGCGGTGTGGTGGGCTGCGGGTCGCGG
AGTGGGTGGGCGGGGAGCCGGCCGCGGCGATTATTGC

Figure 15-3

CGCCAGGCGCTGCCGCCGCTGCCGGCTGCAGCGGCCGAGCAGCCCGGCCAGGCTCG
GGCCCTGGGACCGGCCTGGCCGCCTGGCCGCCAGGGCCGCCAGGCCGCTGCCGGCG
GGGGTCCCCAGGAGGCTTTCTCGCACCCAGGCGGCCACTTCCATTTCG
GTGCGCGCCTCTCTGGCCGAGTCTCGGGCCGGTCCAGGTCGC
CCCGCCGCCATGGCCGCTGGCCTTCTCCCGGCCGGGGTTGCCATTG
CGGCCGACCTCGGCCCGGACTCCCGGCCAGGGCCGGAGCCGCCGGCC
CGCCGGGGTCGGGGCAGGGGGCGGCCGGGGTCTAGA

Figure 15-4

SEQUENCE LISTING

<160> NUMBER OF SEQ ID NOS: 23

<210> SEQ ID NO 1
<211> LENGTH: 291
<212> TYPE: DNA
<213> ORGANISM: Bovine herpesvirus 1

<400> SEQUENCE: 1

```
atgccgcggt cgccgctcat cgttgcggtt gtggccgccg cgctgtttgc catcgtgcgc      60
ggccgcgacc ccctgctaga cgcgatgcgg cgcgaggggg caatggactt ttggagcgca     120
ggctgctacg cgcgcggggt gccgctctcg gagccaccgc aggccctggt tgttttttac     180
gtggccctga ccgcggtaat ggtcgccgtg gccctgtacg cgtacgggct ttgctttagg     240
ctcatgggcg ccagcgggcc caataaaaag gagtcgcggg ggcggggctg a              291
```

<210> SEQ ID NO 2
<211> LENGTH: 96
<212> TYPE: PRT
<213> ORGANISM: Bovine herpesvirus 1

<400> SEQUENCE: 2

```
Met Pro Arg Ser Pro Leu Ile Val Ala Val Val Ala Ala Ala Leu Phe
1               5                   10                  15

Ala Ile Val Arg Gly Arg Asp Pro Leu Leu Asp Ala Met Arg Arg Glu
            20                  25                  30

Gly Ala Met Asp Phe Trp Ser Ala Gly Cys Tyr Ala Arg Gly Val Pro
        35                  40                  45

Leu Ser Glu Pro Pro Gln Ala Leu Val Val Phe Tyr Val Ala Leu Thr
    50                  55                  60

Ala Val Met Val Ala Val Ala Leu Tyr Ala Tyr Gly Leu Cys Phe Arg
65                  70                  75                  80

Leu Met Gly Ala Ser Gly Pro Asn Lys Lys Glu Ser Arg Gly Arg Gly
                85                  90                  95
```

<210> SEQ ID NO 3
<211> LENGTH: 1380
<212> TYPE: DNA
<213> ORGANISM: Bovine herpesvirus 1

<400> SEQUENCE: 3

```
atggggctct tcaagctact gcgttacgcg tacggcaatc ggctggtaaa gcacgacgcc      60
atcaccacgc cgccgggcgt gatgaccccg atcgcggtcg acctgtggaa cgtgatgtat     120
acgctcctgg agcgcttctg cggcgacgcg cccggcggcg taggagacgc cgccgcgacc     180
gcgcgctgct tcctctcgct gctgcggatg ctgctcaagc gctcctacta cccgatcttt     240
gtagcggacc gcggcatcca cggggaccgg cgcgccacgc ggggtgccaa ggccattgtg     300
gcgcagacga tgcgcgccgt cggcggctcg ggccgcctcg ggcggctcgt cagcgacgat     360
tatacctcgg aggacgaggt gctgggcgcg tacgagtacc ccgtcccgca cgcggacgcg     420
gcagccgacg acgacgagga ggcaacggcg aaggaatttg ccgggcgcgc ctcggcgggg     480
gccgcgcggg ccaacgcgcc caagctggca catcgcgtgt gcgtgagcct catccgcttt     540
ttgggctacg cgtacgtcga cgccgctgag atggaggcag acgacgtctg cgcaaacctc     600
ttccacacaa acaccgtggc gcacatctac acgacggaca cggacatgat ccttatgggc     660
tgtgacctga ttttggacgc ggcgccgttg ttccccccga cgctacgctg ccgcgacgtg     720
```

-continued

```
ctggcgtcgc tggggctcac gtacggccag ttcctcgcga cgttcgtgcg ctgccacacc    780
gacttgcacc agccgccaat gctgcgctcg gtgcagcagg tggtgcgggg gctgcggcgc    840
gctgccgagg ccgagcccgc gactaccgag acggagtctg gctccgagcg cgagccggag    900
tccgagctcg gtcgtccggg cgctgggccg cggcgccggt tgccgcccgc ggtcgacgac    960
ccgctgaaaa ctacgacgcc ggcgaccgtg aagcgcaca gcgtgcgcat aagtataca     1020 tctcggtacc ctccgattgc gcagacgtgc gccgacgcgc tgcggctgct gccggcgtcc    1080
cagacgcgcg gcggcgtgct ggagcgcaaa tttgtaaagc acgtggtgga cacgatcgcg    1140
ccgcgaatgc gcgggcgctg ggccgtgctg aagcgcgtgc ccatcgcaca ggacgccccc    1200
gaccctcggc tcgtgtacga caccatcgtg agcgccgtag gcagcgccgc cgaggccgac    1260
acgctgatgg ggctcttctg gaagcacatc cccactccac ccccatttgc caaggtgctg    1320
gcagactact gggacgaggc ccccgcgggg ccggggtcgc gacggacaac ccgccaataa    1380
```

<210> SEQ ID NO 4
<211> LENGTH: 459
<212> TYPE: PRT
<213> ORGANISM: Bovine herpesvirus 1

<400> SEQUENCE: 4

```
Met Gly Leu Phe Lys Leu Leu Arg Tyr Ala Tyr Gly Asn Arg Leu Val
1               5                   10                  15

Lys His Asp Ala Ile Thr Thr Pro Pro Gly Val Met Thr Pro Ile Ala
            20                  25                  30

Val Asp Leu Trp Asn Val Met Tyr Thr Leu Leu Glu Arg Phe Cys Gly
        35                  40                  45

Asp Ala Pro Gly Gly Val Gly Asp Ala Ala Thr Ala Arg Cys Phe
    50                  55                  60

Leu Ser Leu Leu Arg Met Leu Leu Lys Arg Ser Tyr Tyr Pro Ile Phe
65                  70                  75                  80

Val Ala Asp Arg Gly Ile His Gly Asp Arg Ala Thr Arg Gly Ala
                85                  90                  95

Lys Ala Ile Val Ala Gln Thr Met Arg Ala Val Gly Gly Ser Gly Arg
            100                 105                 110

Leu Gly Arg Leu Val Ser Asp Asp Tyr Thr Ser Glu Asp Glu Val Leu
        115                 120                 125

Gly Ala Tyr Glu Tyr Pro Val Pro His Ala Asp Ala Ala Asp Asp
    130                 135                 140

Asp Glu Glu Ala Thr Ala Lys Glu Phe Ala Gly Arg Ala Ser Ala Gly
145                 150                 155                 160

Ala Ala Arg Ala Asn Ala Pro Lys Leu Ala His Arg Val Cys Val Ser
                165                 170                 175

Leu Ile Arg Phe Leu Gly Tyr Ala Tyr Val Asp Ala Ala Glu Met Glu
            180                 185                 190

Ala Asp Asp Val Cys Ala Asn Leu Phe His Thr Asn Thr Val Ala His
        195                 200                 205

Ile Tyr Thr Thr Asp Thr Asp Met Ile Leu Met Gly Cys Asp Leu Ile
    210                 215                 220

Leu Asp Ala Ala Pro Leu Phe Pro Pro Thr Leu Arg Cys Arg Asp Val
225                 230                 235                 240

Leu Ala Ser Leu Gly Leu Thr Tyr Gly Gln Phe Leu Ala Thr Phe Val
                245                 250                 255

Arg Cys His Thr Asp Leu His Gln Pro Pro Met Leu Arg Ser Val Gln
            260                 265                 270
```

```
Gln Val Val Arg Gly Leu Arg Arg Ala Ala Glu Ala Glu Pro Ala Thr
            275                 280                 285
Thr Glu Thr Glu Ser Gly Ser Glu Arg Glu Pro Glu Ser Glu Leu Gly
        290                 295                 300
Arg Pro Gly Ala Gly Pro Arg Arg Leu Pro Ala Val Asp Asp
305                 310                 315                 320
Pro Leu Lys Thr Thr Thr Pro Ala Thr Val Glu Ala His Ser Val Arg
                325                 330                 335
Met Lys Tyr Thr Ser Arg Tyr Pro Pro Ile Ala Gln Thr Cys Ala Asp
            340                 345                 350
Ala Leu Arg Leu Leu Pro Ala Ser Gln Thr Arg Gly Gly Val Leu Glu
        355                 360                 365
Arg Lys Phe Val Lys His Val Val Asp Thr Ile Ala Pro Arg Met Arg
    370                 375                 380
Gly Arg Trp Ala Val Leu Lys Arg Val Pro Ile Ala Gln Asp Ala Pro
385                 390                 395                 400
Asp Pro Arg Leu Val Tyr Asp Thr Ile Val Ser Ala Val Gly Ser Ala
                405                 410                 415
Ala Glu Ala Asp Thr Leu Met Gly Leu Phe Trp Lys His Ile Pro Thr
            420                 425                 430
Pro Pro Pro Phe Ala Lys Val Leu Ala Asp Tyr Trp Asp Glu Ala Pro
        435                 440                 445
Ala Gly Pro Gly Ser Arg Arg Thr Thr Arg Gln
    450                 455

<210> SEQ ID NO 5
<211> LENGTH: 744
<212> TYPE: DNA
<213> ORGANISM: Bovine herpesvirus 1

<400> SEQUENCE: 5
atgggtgccc gcgcctccgc gcctgctgcc ggcccgcccc cagcccacgc tgttctacta      60
gatgcgctct ccgggggcac gattgacctg cctggcggcg acgaggccgt ctttgtgtcc     120
tgcccgacga cgcgccccgt gtaccaccac atgccgccgc gccgcacggc ccacactaca     180
cccgtgcact tcgttggccg cgcctatgcc atcttgccct gccgcaagtt tatgctgtat     240
ctgatgcgcg gtggtgccgt ttacggctac gagcccacca ctggcctgca ccgcctcgcc     300
gattcactgc acgactttct tactactgcc ggactacagc agcgagacct acactgcctc     360
gatgtcacgg tgcttgacgc gcagatggac ccggtgacgt tcaccacccc cgagatcctc     420
atcgagctcg aggcggaccc ggccttccca ccgccgccct cggcccgcgc cgccgctcc     480 acgctgcgcc gggcgtctat cgccggcc gcacgcacct tctgccccca ccagctgcta     540
gcagagggct ccattctgga cctctgctcg ccagagcaag cggcggcgcc gggctgttcg     600
ctgctccccg cctgtgactc tggagacgcc gcgtgccccct gcgacgctgg cgagaccgcc     660
cgtgactgta ctgccgatgc cgcgcgcgct cccagccccg cgccttatc tcgctatagc     720 tccgtgcgct cggtgttctt ttag                                             744

<210> SEQ ID NO 6
<211> LENGTH: 247
<212> TYPE: PRT
<213> ORGANISM: Bovine herpesvirus 1

<400> SEQUENCE: 6

Met Gly Ala Arg Ala Ser Ala Pro Ala Ala Gly Pro Pro Pro Ala His
```

-continued

```
1               5                   10                  15

Ala Val Leu Leu Asp Ala Leu Ser Gly Gly Thr Ile Asp Leu Pro Gly
            20                  25                  30

Gly Asp Glu Ala Val Phe Val Ser Cys Pro Thr Thr Arg Pro Val Tyr
        35                  40                  45

His His Met Arg Arg Gly Arg Thr Ala His Thr Thr Pro Val His Phe
    50                  55                  60

Val Gly Arg Ala Tyr Ala Ile Leu Pro Cys Arg Lys Phe Met Leu Tyr
65                  70                  75                  80

Leu Met Arg Gly Gly Ala Val Tyr Gly Tyr Glu Pro Thr Thr Gly Leu
                85                  90                  95

His Arg Leu Ala Asp Ser Leu His Asp Phe Leu Thr Thr Ala Gly Leu
            100                 105                 110

Gln Gln Arg Asp Leu His Cys Leu Asp Val Thr Val Leu Asp Ala Gln
        115                 120                 125

Met Asp Pro Val Thr Phe Thr Thr Pro Glu Ile Leu Ile Glu Leu Glu
    130                 135                 140

Ala Asp Pro Ala Phe Pro Pro Pro Pro Ser Ala Arg Ala Arg Arg Ser
145                 150                 155                 160

Thr Leu Arg Arg Ala Ser Met Arg Arg Pro Ala Arg Thr Phe Cys Pro
                165                 170                 175

His Gln Leu Leu Ala Glu Gly Ser Ile Leu Asp Leu Cys Ser Pro Glu
            180                 185                 190

Gln Ala Ala Ala Pro Gly Cys Ser Leu Leu Pro Ala Cys Asp Ser Gly
        195                 200                 205

Asp Ala Ala Cys Pro Cys Asp Ala Gly Glu Thr Ala Arg Asp Cys Thr
    210                 215                 220

Ala Asp Ala Ala Arg Ala Pro Ser Pro Gly Ala Leu Ser Arg Tyr Ser
225                 230                 235                 240

Ser Val Arg Ser Val Phe Phe
                245
```

<210> SEQ ID NO 7
<211> LENGTH: 1014
<212> TYPE: DNA
<213> ORGANISM: Bovine herpesvirus 1

<400> SEQUENCE: 7

```
atggcgctcg ctggccttct ctcccggccg gggttgccat tgcggccgac ctcggcccgg      60
gcggctccgg ccagggccgg agcgccggcc cgccgggggt cggcggcagg ggcgcggccg     120
gcgggagacg gggtcggggc tcgggtggaa atagccgcgg cggtgctggt agccgccgcg     180
gtaacagcgg ggctcggcgc cgagctccga gcgacggaag gtgccgccgc ggcggcagtt     240
actgccgccg ccgcggccgg ggtcccaatt tgcgcacccg ccgaggccgg ccccggggcc     300
gccgcggggg ccgggtcggc ggggcgggcg ggcgcgttcg ccgtcaggtc tatcactgtg     360
gagatgggcg cgggggctgg ggccggggcc ggggccgggg tcggggcgcg gtctaactct     420
gtccttcttc tccggcgggc ctgcacacgg ggaggcccag cctccccgag cagcctggcc     480
cggcgctccc ctcgtccctc ctcactgccc gccccccagc ccgcggtctc tcccgccgcg     540
actcccaagc ccgctcccct cccctcttct ctgggctcgg ggctgcatgc gcgcgcttgc     600
gccgcggggg ctgcccgcgg cgccgccggc aatcgggggt ctcgtctccc gccgcggctc     660
cgagagctgg ggggcgcgga aactgccgcc gcgcggccgc aagggcggcg cgctagcgac     720
cgaggcgccg gctgcaccgc gggtgtttgt cgacctctag tgctgacata ctgtctttcc     780
```

```
gcaggccgcc gagcccgggc cgcgccagac gcccccgcg tgcgcctcga ctcaacctcc    840
gcgtccgtct ccggctccgt ttccgtgtcg tcaatggcgg tcaggtcgga ggtgctgagc    900
cccgacgacg actcttctga ctccgaccaa gagtcgtcct ccgagccctc cgagtccgag    960
tccgaggtgt cgagaaacac caccccacgg ccgccaggag gcgcagactg ctga        1014

<210> SEQ ID NO 8
<211> LENGTH: 335
<212> TYPE: PRT
<213> ORGANISM: Bovine herpesvirus 1

<400> SEQUENCE: 8

Met Ala Leu Ala Gly Leu Leu Ser Arg Pro Gly Leu Pro Leu Arg Pro
1               5                   10                  15

Thr Ser Ala Arg Ala Ala Pro Ala Arg Ala Gly Ala Pro Ala Arg Arg
            20                  25                  30

Gly Ser Ala Ala Gly Ala Arg Pro Ala Gly Asp Gly Val Gly Ala Arg
        35                  40                  45

Val Glu Ile Ala Ala Ala Val Leu Val Ala Ala Ala Val Thr Ala Gly
    50                  55                  60

Leu Gly Ala Glu Leu Arg Ala Thr Glu Gly Ala Ala Ala Ala Ala Val
65                  70                  75                  80

Thr Ala Ala Ala Ala Ala Gly Val Pro Ile Cys Ala Pro Ala Glu Ala
                85                  90                  95

Gly Pro Gly Ala Ala Ala Gly Ala Gly Ser Ala Gly Arg Ala Gly Ala
            100                 105                 110

Phe Ala Val Arg Ser Ile Thr Val Glu Met Gly Ala Gly Ala Gly Ala
        115                 120                 125

Gly Ala Gly Ala Gly Val Gly Ala Arg Ser Asn Ser Val Leu Leu Leu
    130                 135                 140

Arg Arg Ala Cys Thr Arg Gly Gly Pro Ala Ser Pro Ser Ser Leu Ala
145                 150                 155                 160

Arg Arg Ser Pro Arg Pro Ser Ser Leu Pro Ala Pro Gln Pro Ala Val
                165                 170                 175

Ser Pro Ala Ala Thr Pro Lys Pro Ala Pro Leu Pro Ser Ser Leu Gly
            180                 185                 190

Ser Gly Leu His Ala Arg Ala Cys Ala Ala Gly Ala Ala Arg Gly Ala
        195                 200                 205

Ala Gly Asn Arg Gly Ser Arg Leu Pro Pro Arg Leu Arg Glu Leu Gly
    210                 215                 220

Gly Ala Glu Thr Ala Ala Ala Arg Pro Gln Gly Arg Arg Ala Ser Asp
225                 230                 235                 240

Arg Gly Ala Gly Cys Thr Ala Gly Val Cys Arg Pro Leu Val Leu Thr
                245                 250                 255

Tyr Cys Leu Ser Ala Gly Arg Arg Ala Arg Ala Ala Pro Asp Ala Pro
            260                 265                 270

Arg Val Arg Leu Asp Ser Thr Ser Ala Ser Val Ser Gly Ser Val Ser
        275                 280                 285

Val Ser Ser Met Ala Val Arg Ser Glu Val Leu Ser Pro Asp Asp Asp
    290                 295                 300

Ser Ser Asp Ser Asp Gln Glu Ser Ser Ser Glu Pro Ser Glu Ser Glu
305                 310                 315                 320

Ser Glu Val Ser Arg Asn Thr Thr Pro Arg Pro Pro Gly Gly Ala
                325                 330                 335
```

<210> SEQ ID NO 9
<211> LENGTH: 545
<212> TYPE: DNA
<213> ORGANISM: Bovine herpesvirus 1

<400> SEQUENCE: 9

| | | | | | |
|---|---|---|---|---|---|
| atgcgcgacc | tgggccataa | aagccccgcg | catgcgcgag | cagttacttt | cggtttgggg | 60 |
| atgacagcgg | cgactgcggc | tcgaaagtta | agtatgcagg | ctgggggtcg | caaatacacg | 120 |
| gcggtgcggt | gtggtgggct | gcgggtcgcg | gagtgggtgg | gcggggagcc | ggccgcggcg | 180 |
| attattgccg | ccaggcgctg | ccgccgctgc | agcggccgag | cagcccggcc | aggctcgggc | 240 |
| cctggcgacc | gcctggctgc | ggcgccaggg | ccgcgctgct | gcggcggggg | gtccccagga | 300 |
| ggctttctcg | cacccaggcg | gccacttcca | tttcggtgcg | ccgcctcttc | tgcgccgagc | 360 |
| tctcggggcc | ggggtccagg | tcgccccgcg | ccatggcgct | cgctggcctt | ctctcccggc | 420 |
| cggggttgcc | attgcggccg | acctcggccc | gggcggctcc | ggccagggcc | ggagcgccgg | 480 |
| cccgccgggg | gtcggcggca | ggggcgcggc | cggcgggaga | cggggtcggg | gctcgggtgg | 540 |
| aaata | | | | | | 545 |

<210> SEQ ID NO 10
<211> LENGTH: 181
<212> TYPE: PRT
<213> ORGANISM: Bovine herpesvirus 1

<400> SEQUENCE: 10

Met Arg Asp Leu Gly His Lys Ser Pro Ala His Ala Arg Ala Val Thr
1               5                   10                  15

Phe Gly Leu Gly Met Thr Ala Ala Thr Ala Ala Arg Lys Leu Ser Met
            20                  25                  30

Gln Ala Gly Gly Arg Lys Tyr Thr Ala Val Arg Cys Gly Gly Leu Arg
        35                  40                  45

Val Ala Glu Trp Val Gly Gly Glu Pro Ala Ala Ile Ile Ala Ala
    50                  55                  60

Arg Arg Cys Arg Arg Cys Ser Gly Arg Ala Ala Arg Pro Gly Ser Gly
65                  70                  75                  80

Pro Gly Asp Arg Leu Ala Ala Ala Pro Gly Pro Arg Cys Cys Gly Gly
                85                  90                  95

Gly Ser Pro Gly Gly Phe Leu Ala Pro Arg Arg Pro Leu Pro Phe Arg
            100                 105                 110

Cys Ala Ala Ser Ser Ala Pro Ser Arg Gly Arg Gly Pro Gly Arg
        115                 120                 125

Pro Ala Pro Trp Arg Ser Leu Ala Phe Ser Pro Gly Arg Gly Cys His
    130                 135                 140

Cys Gly Arg Pro Arg Pro Gly Arg Leu Arg Pro Gly Pro Glu Arg Arg
145                 150                 155                 160

Pro Ala Gly Gly Arg Arg Gln Gly Arg Gly Arg Glu Thr Gly Ser
                165                 170                 175

Gly Leu Gly Trp Lys
            180

<210> SEQ ID NO 11
<211> LENGTH: 1335
<212> TYPE: DNA
<213> ORGANISM: Bovine herpesvirus 1

<400> SEQUENCE: 11

-continued

```
atgcctgccg cccggaccgg caccttggcc gccgtcgccc taatcctgct ctgcggggcc    60
gccgttttgg ggcgccccgc gcccgacgac ctctgtttcg ccgacgtgcg ccgcactggc   120
atggcgccct cccgcccgct ggggcccgtc ctgaacctag cggcctcgga tttgacctcg   180
cgggtttcgg tgcgcgcggt ggacgcttcg cgcggctgcg ccctggccct cttggacatg   240
gcggagacgg tggtgcccgg cggaccgcga ccgccgacg tcgtcgacgt cggctgggct   300
taccaagacg gggactgcat ggtgcctctg catatcgcc agtactttaa ctgcacgggg   360
ggcgcgctgc ccggccaaaa cgtctgcgcc gggctctctg agacccgcat ccgcggtggc   420
tttggaacct ccgactacgc gctctacggg acgtcgctag tactgcgccc cggcctgtac   480
gaccgcggga cctacatcta cttccttgga tacggcccag acgacatcta cgtgggcagc   540
gtcacgctca tggtgggcgc cgacatccac aaataccccct gcgggctgga ccagggctc   600
ggtgtggccc tgcaccacaa gagcggaccg gcccgacctc tgacagagga cgacgccacc   660
ggcgactggg cctgcggctg cttccccgcc cttgttgagg ttgacgcggt gtggggcaac   720
gtaagcgccg cagagctggg cctggccgac ccgatcgact acgccgacga agggggtgag   780
gtcgaagtgc tcgaggacga agccgggagc gccagcggaa acctgccgca ggacgacccc   840
gaccccgacc tcgcagattg ccggaccgtc gggctcttta gcgaaagcga catgttccgg   900
accgccagcg ggcccgaatc gctgctgatc ggcgccgttg ccaaggacgt cctgacggtg   960
cccctcaatc tgccgcccgg ccgctcttac gaggccctgc gaaacgcatc gctggagtgc  1020
aactcccgcc cgcgcgagac cggcgacgca gcggtggtgg tgatgtctct ccaggagccc  1080
gctcgcctcg agcgccgccc cgatgcccgc gccaccgatc cggagtttgg gctctttggc  1140
ctgcccgatg accccgccgt gcggcgcggc attctcatcg gcctcgcgat cgctctgctg  1200
gtgctgctgt tttcgctggt gatcgtgctc gtctgcgcct gccggctcgc ccgcgcagcc  1260
aaggctgcgc gacgcgcccg cgccgccacg ttcgccaaga gcaacccgc gtacgagccg  1320
atgctcagcg tctga                                                   1335
```

<210> SEQ ID NO 12
<211> LENGTH: 444
<212> TYPE: PRT
<213> ORGANISM: Bovine herpesvirus 1

<400> SEQUENCE: 12

Met Pro Ala Ala Arg Thr Gly Thr Leu Ala Ala Val Ala Leu Ile Leu
1               5                   10                  15

Leu Cys Gly Ala Ala Val Leu Gly Arg Pro Ala Pro Asp Asp Leu Cys
            20                  25                  30

Phe Ala Asp Val Arg Arg Thr Gly Met Ala Pro Ser Arg Pro Leu Gly
        35                  40                  45

Pro Val Leu Asn Leu Ala Ala Ser Asp Leu Thr Ser Arg Val Ser Val
    50                  55                  60

Arg Ala Val Asp Ala Ser Arg Gly Cys Ala Leu Ala Leu Leu Asp Met
65                  70                  75                  80

Ala Glu Thr Val Val Pro Gly Gly Pro Arg Ala Ala Asp Val Val Asp
                85                  90                  95

Val Gly Trp Ala Tyr Gln Asp Gly Asp Cys Met Val Pro Leu Ala Tyr
            100                 105                 110

Arg Gln Tyr Phe Asn Cys Thr Gly Gly Ala Leu Pro Gly Gln Asn Val
        115                 120                 125

Cys Ala Gly Leu Ser Glu Thr Arg Ile Arg Gly Gly Phe Gly Thr Ser
    130                 135                 140

```
Asp Tyr Ala Leu Tyr Gly Thr Ser Leu Val Leu Arg Pro Gly Leu Tyr
145                 150                 155                 160

Asp Arg Gly Thr Tyr Ile Tyr Phe Leu Gly Tyr Gly Pro Asp Asp Ile
                165                 170                 175

Tyr Val Gly Ser Val Thr Leu Met Val Gly Ala Asp Ile His Lys Tyr
            180                 185                 190

Pro Cys Gly Leu Asp Arg Gly Leu Gly Val Ala Leu His His Lys Ser
        195                 200                 205

Gly Pro Ala Arg Pro Leu Thr Glu Asp Asp Ala Thr Gly Asp Trp Ala
    210                 215                 220

Cys Gly Cys Phe Pro Ala Leu Val Glu Val Asp Ala Val Trp Gly Asn
225                 230                 235                 240

Val Ser Ala Ala Glu Leu Gly Leu Ala Asp Pro Ile Asp Tyr Ala Asp
                245                 250                 255

Glu Gly Gly Glu Val Glu Val Leu Glu Asp Glu Ala Gly Ser Ala Ser
            260                 265                 270

Gly Asn Leu Pro Gln Asp Asp Pro Asp Pro Asp Leu Ala Asp Cys Arg
        275                 280                 285

Thr Val Gly Leu Phe Ser Glu Ser Asp Met Phe Arg Thr Ala Ser Gly
    290                 295                 300

Pro Glu Ser Leu Leu Ile Gly Ala Val Ala Lys Asp Val Leu Thr Val
305                 310                 315                 320

Pro Leu Asn Leu Pro Pro Gly Arg Ser Tyr Glu Ala Leu Arg Asn Ala
                325                 330                 335

Ser Leu Glu Cys Asn Ser Arg Pro Arg Glu Thr Gly Asp Ala Ala Val
            340                 345                 350

Val Val Met Ser Leu Gln Glu Pro Ala Arg Leu Glu Arg Arg Pro Asp
        355                 360                 365

Ala Arg Ala Thr Asp Pro Glu Phe Gly Leu Phe Gly Leu Pro Asp Asp
    370                 375                 380

Pro Ala Val Arg Arg Gly Ile Leu Ile Gly Leu Ala Ile Ala Leu Leu
385                 390                 395                 400

Val Leu Leu Phe Ser Leu Val Ile Val Leu Val Cys Ala Cys Arg Leu
                405                 410                 415

Ala Arg Ala Ala Lys Ala Ala Arg Arg Ala Arg Ala Ala Thr Phe Ala
            420                 425                 430

Lys Ser Asn Pro Ala Tyr Glu Pro Met Leu Ser Val
        435                 440
```

<210> SEQ ID NO 13
<211> LENGTH: 435
<212> TYPE: DNA
<213> ORGANISM: Bovine herpesvirus 1

<400> SEQUENCE: 13

```
atggagagtc cacgcagcgt cgtcaacgaa aactatcgag gcgctgatga ggccgatgca      60
gcgccccctt caccgccgcc ggaaggctcc atcgtgtcca tccccatcct cgagctcacc     120
atcgaggacg cgccggccag cgcagaagca accggcaccg cggcagccgc acccgctggg     180
cgcactccag acgcgaacgc agcacccggc ggctacgtgc cagttcccgc ggcggatgtg     240
gactgctatt atagcgaaag cgacagcgag acggcaggcg agtttttgat acgcatgggg     300
cggcagcagc ggcggcggca tcggcggcgg cgctgcatga tagcagcggc cctgacttgc     360
attggcctcg gggcctgcgc ggcggcggca gcggcaggcg ccgtcctggc gttggaggta     420
```
gtgccccggc cctga 435

<210> SEQ ID NO 14
<211> LENGTH: 144
<212> TYPE: PRT
<213> ORGANISM: Bovine herpesvirus 1

<400> SEQUENCE: 14

```
Met Glu Ser Pro Arg Ser Val Val Asn Glu Asn Tyr Arg Gly Ala Asp
1               5                   10                  15

Glu Ala Asp Ala Ala Pro Pro Ser Pro Pro Pro Glu Gly Ser Ile Val
            20                  25                  30

Ser Ile Pro Ile Leu Glu Leu Thr Ile Glu Asp Ala Pro Ala Ser Ala
        35                  40                  45

Glu Ala Thr Gly Thr Ala Ala Ala Ala Pro Ala Gly Arg Thr Pro Asp
    50                  55                  60

Ala Asn Ala Ala Pro Gly Gly Tyr Val Pro Val Pro Ala Ala Asp Val
65                  70                  75                  80

Asp Cys Tyr Tyr Ser Glu Ser Asp Ser Glu Thr Ala Gly Glu Phe Leu
                85                  90                  95

Ile Arg Met Gly Arg Gln Gln Arg Arg Arg His Arg Arg Arg Arg Cys
            100                 105                 110

Met Ile Ala Ala Ala Leu Thr Cys Ile Gly Leu Gly Ala Cys Ala Ala
        115                 120                 125

Ala Ala Ala Ala Gly Ala Val Leu Ala Leu Glu Val Val Pro Arg Pro
    130                 135                 140
```

<210> SEQ ID NO 15
<211> LENGTH: 1728
<212> TYPE: DNA
<213> ORGANISM: Bovine herpesvirus 1

<400> SEQUENCE: 15

```
atgcaaccca ccgcgccgcc ccggcggcgg ttgctgccgc tgctgctgcc gcagttattg      60
cttttcgggc tgatggccga ggccaagccc gcgaccgaaa ccccgggctc ggcttcggtc     120
gacacggtct tcacggcgcg cgctggcgcg cccgtctttc tcccagggcc cgcggcgcgc     180
ccggacgtgc gcgccgttcg cggctggagc gtcctcgcgg gcgcctgctc gccgcccgtg     240
ccggagcccg tctgcctcga cgaccgcgag tgcttcaccg acgtggccct ggacgcggcc     300
tgcctgcgaa ccgcccgcgt ggccccgctg gccatcgcgg agctcgccga gcggcccgac     360
tcaacgggcg acaaagagtt tgttctcgcc gacccgcacg tctcggcgca gctgggtcgc     420
aacgcgaccg gggtgctgat cgcggccgca gccgaggagg acggcggcgt gtacttcctg     480
tacgaccggc tcatcggcga cgccggcgac gaggagacgc agttggcgct gacgctgcag     540
gtcgcgacgg ccggcgcgca gggcgccgcg cgggacgagg agagggaacc agcgaccggg     600
cccacccccg gcccgccgcc ccaccgcacg acgacacgcg cgcccccgcg gcggcacggc     660
gcgcgcttcc gcgtgctgcc gtaccactcc cacgtataca ccccgggcga ttcctttctg     720
ctatcggtgc gtctgcagtc tgagtttttc gacgaggctc ccttctcggc cagcatcgac     780
tggtacttcc tgcggacggc cggcgactgc gcgctcatcc gcatatacga gacgtgcatc     840
ttccaccccg aggcaccggc ctgcctgcac cccgccgacg cgcagtgcag cttcgcgtcg     900
ccgtaccgct ccgagaccgt gtacagccgg ctgtacgagc agtgccgccc ggaccctgcc     960
ggtcgctggc cgcacgagtg cgagggcgcc gcgtacgcgg cgcccgttgc gcacctgcgt    1020
cccgccaata acagcgtaga cctggtcttt gacgacgcgc cggctgcggc ctccgggctt    1080
```

```
tacgtctttg tgctgcagta caacggccac gtggaagctt gggactacag cctagtcgtt    1140
acttcggacc gtttggtgcg cgcggtcacc gaccacacgc gccccgaggc cgcagccgcc    1200
gacgctcccg agccaggccc accgctcacc agcgagccgg cgggcgcgcc caccgggccc    1260
gcgccctggc ttgtggtgct ggtgggcgcg cttggactcg cgggactggt gggcatcgca    1320
gccctcgccg ttcgggtgtg cgcgcgccgc gcaagccaga agcgcaccta cgacatcctc    1380
aaccccttcg ggcccgtata caccagcttg ccgaccaacg agccgctcga cgtggtggtg    1440
ccagttagcg acgacgaatt ttccctcgac gaagactctt ttgcggatga cgacagcgac    1500
gatgacgggc ccgctagcaa ccccctgcg gatgcctacg acctcgccgg cgccccagag    1560
ccaactagcg ggtttgcgcg agcccccgcc aacggcacgc gctcgagtcg ctctgggttc    1620
aaagtttggt ttagggaccc gcttgaagac gatgccgcgc cagcgcggac cccggccgca    1680
ccagattaca ccgtggtagc agcgcgactc aagtccatcc tccgctag              1728
```

<210> SEQ ID NO 16
<211> LENGTH: 575
<212> TYPE: PRT
<213> ORGANISM: Bovine herpesvirus 1

<400> SEQUENCE: 16

```
Met Gln Pro Thr Ala Pro Pro Arg Arg Leu Leu Pro Leu Leu
1               5                   10                  15

Pro Gln Leu Leu Leu Phe Gly Leu Met Ala Glu Ala Lys Pro Ala Thr
            20                  25                  30

Glu Thr Pro Gly Ser Ala Ser Val Asp Thr Val Phe Thr Ala Arg Ala
        35                  40                  45

Gly Ala Pro Val Phe Leu Pro Gly Pro Ala Ala Arg Pro Asp Val Arg
    50                  55                  60

Ala Val Arg Gly Trp Ser Val Leu Ala Gly Ala Cys Ser Pro Val
65                  70                  75                  80

Pro Glu Pro Val Cys Leu Asp Asp Arg Glu Cys Phe Thr Asp Val Ala
                85                  90                  95

Leu Asp Ala Ala Cys Leu Arg Thr Ala Arg Val Ala Pro Leu Ala Ile
            100                 105                 110

Ala Glu Leu Ala Glu Arg Pro Asp Ser Thr Gly Asp Lys Glu Phe Val
        115                 120                 125

Leu Ala Asp Pro His Val Ser Ala Gln Leu Gly Arg Asn Ala Thr Gly
    130                 135                 140

Val Leu Ile Ala Ala Ala Glu Glu Asp Gly Gly Val Tyr Phe Leu
145                 150                 155                 160

Tyr Asp Arg Leu Ile Gly Asp Ala Gly Asp Glu Glu Thr Gln Leu Ala
                165                 170                 175

Leu Thr Leu Gln Val Ala Thr Ala Gly Ala Gln Gly Ala Ala Arg Asp
            180                 185                 190

Glu Glu Arg Glu Pro Ala Thr Gly Pro Thr Pro Gly Pro Pro His
        195                 200                 205

Arg Thr Thr Thr Arg Ala Pro Pro Arg Arg His Gly Ala Arg Phe Arg
    210                 215                 220

Val Leu Pro Tyr His Ser His Val Tyr Thr Pro Gly Asp Ser Phe Leu
225                 230                 235                 240

Leu Ser Val Arg Leu Gln Ser Glu Phe Phe Asp Glu Ala Pro Phe Ser
                245                 250                 255

Ala Ser Ile Asp Trp Tyr Phe Leu Arg Thr Ala Gly Asp Cys Ala Leu
```

```
              260             265             270
Ile Arg Ile Tyr Glu Thr Cys Ile Phe His Pro Glu Ala Pro Ala Cys
            275                 280                 285

Leu His Pro Ala Asp Ala Gln Cys Ser Phe Ala Ser Pro Tyr Arg Ser
        290                 295                 300

Glu Thr Val Tyr Ser Arg Leu Tyr Glu Gln Cys Arg Pro Asp Pro Ala
305                 310                 315                 320

Gly Arg Trp Pro His Glu Cys Glu Gly Ala Ala Tyr Ala Ala Pro Val
                325                 330                 335

Ala His Leu Arg Pro Ala Asn Asn Ser Val Asp Leu Val Phe Asp Asp
            340                 345                 350

Ala Pro Ala Ala Ala Ser Gly Leu Tyr Val Phe Val Leu Gln Tyr Asn
        355                 360                 365

Gly His Val Glu Ala Trp Asp Tyr Ser Leu Val Val Thr Ser Asp Arg
370                 375                 380

Leu Val Arg Ala Val Thr Asp His Thr Arg Pro Glu Ala Ala Ala Ala
385                 390                 395                 400

Asp Ala Pro Glu Pro Gly Pro Pro Leu Thr Ser Glu Pro Ala Gly Ala
                405                 410                 415

Pro Thr Gly Pro Ala Pro Trp Leu Val Val Leu Val Gly Ala Leu Gly
            420                 425                 430

Leu Ala Gly Leu Val Gly Ile Ala Ala Leu Ala Val Arg Val Cys Ala
        435                 440                 445

Arg Arg Ala Ser Gln Lys Arg Thr Tyr Asp Ile Leu Asn Pro Phe Gly
450                 455                 460

Pro Val Tyr Thr Ser Leu Pro Thr Asn Glu Pro Leu Asp Val Val Val
465                 470                 475                 480

Pro Val Ser Asp Asp Glu Phe Ser Leu Asp Glu Asp Ser Phe Ala Asp
                485                 490                 495

Asp Asp Ser Asp Asp Gly Pro Ala Ser Asn Pro Pro Ala Asp Ala
            500                 505                 510

Tyr Asp Leu Ala Gly Ala Pro Glu Pro Thr Ser Gly Phe Ala Arg Ala
        515                 520                 525

Pro Ala Asn Gly Thr Arg Ser Ser Arg Ser Gly Phe Lys Val Trp Phe
530                 535                 540

Arg Asp Pro Leu Glu Asp Ala Ala Pro Ala Arg Thr Pro Ala Ala
545                 550                 555                 560

Pro Asp Tyr Thr Val Val Ala Ala Arg Leu Lys Ser Ile Leu Arg
            565                 570                 575

<210> SEQ ID NO 17
<211> LENGTH: 1026
<212> TYPE: DNA
<213> ORGANISM: Bovine herpesvirus 1

<400> SEQUENCE: 17
aagcttaaag aagggcactt cgacgcccgc ctctgtcccg gcgtttgcgt cgtcgtcgac    60
ggcgatgagg cgaggcagcg tggtggttag ccgcgcgagc gtcagccgca gcgcaagccc   120
cgccggggga gcggccgctg cggactcggg cgcccagacg atggcgcgca agatccccga   180
gtagcccgag tcgacgatgc cgacggccac ggctggtggg cggggcatgt gtgtgtcacc   240
cgagcgcatt tgcgacatta taatggcata tccgccgggc gcggccgcct tcatgtttaa   300
gttaatcagc cggctatataaa ggagagatcc cgacggggct gttcatctc gctttgctgc   360 tggcgcaatt gggccccaga gcgccagcga gtcgggctca cagcagcttt ccaaccgcca   420
```

-continued

```
gggggccgcc tccgcgttga gctctacgac gaggatcccg cggtcgccgc tcatcgttgc    480
ggttgtggcc gccgcgctgt ttgccatatt aatgatatcc ttaagtgatt gaccgcaacg    540
ctgcggagta acttgtatat aaagctcgcg gtcccggcga ccgctgcctt tttcgcactc    600
ggcccgaccc gctttgagct gcacgcccgc cggcccgccg actcgcttgc catggcccgg    660
ttccacaggc cctccgaaga cgaggacgat tacgagtaca gcgacctttg ggtgcgagaa    720
aacagcctct atgactacga gtccggctcg gatgaccacg tatacgaaga gctgcgcgcc    780
gcgacgagcg gacccgagcc gagcgggcgg cgcgctagcg tccgtgcgtg cgccagcgct    840
gcagccgtcc agcccgccgc ccgcggccgc gatcgagccg cagccgcggg gacgaccgta    900
gctgcgcccg ccgccgcgcc ggcccgccgc tcgagcagcc gggcgtcctc gcgcccgccg    960
cgagctgccg ccgacccgcc cgtcctccgg ccagccacgc gcgggtcctc cggcggcgcc   1020
ggggca                                                              1026
```

```

<210> SEQ ID NO 18
<211> LENGTH: 1030
<212> TYPE: DNA
<213> ORGANISM: Bovine herpesvirus 1

<400> SEQUENCE: 18
aagcttctgg catacccgcg cgcgctgttc gacagccccg cgggcccgca gggcgaggac     60
gccgaggcat cgggcccgcc gacgatcttg ggcgaccgcg actgcgcccg gcagctgctc    120
cgcgtgattc gccggctggc cgtgcacgcc gaagagtttc cacccagccc cactgaccgg    180
ctgacccgca acttcaagcg ccacgcgagc acgcgccgag agccgcacag cccgtaccgc    240
tgcctggcgg tgctccggct gccctgcgac gccgaccgcc tcctacacca gatgctgacc    300
tttgactttc gcgcgcgccc caccgccgcg gagctgctgg agcaccccgt cttcggtgcg    360
gcctcggggt agccccgggg gtttcccgca aaactgaggc atataaggcg cgggcaccgg    420
caagtttggc atccacactt cgcgctgtgg acacgagagc gaacgcgagc gaacgcgagc    480
gcaagcgcga gcacacgact gcgatcatta atgatatcct taagtcgccg gcaccccacg    540
ccgccccgac cccgctgtcc cgcgtttaca ataaacagtt attcttacca acgttggtgc    600
gcctgtcgcg tgtctattgc gagttaaacc gagtgcccca cccaggcagg gcgggggttg    660
ggccgggccg cagccccggc tgggtatata tccccgacgg gcgactagag atacactcgc    720
cccgcgcggc tgctgcgagc gggcgaacat gcaagggccg acattggccg tgctgggcgc    780
gctgctcgcc gttgcggtga gcttgcctac acccgcgccg cgggtgacgg tatacgtcga    840
cccgccggcg tacccgatgc cgcgatacaa ctacactgaa cgctggcaca ctaccgggcc    900
cataccgtcg cccttcgcag acggccgcga gcagcccgtc gaggtgcgct acgcgacgag    960
cgcggcggcg tgcgacatgc tggcgctgat cgcagacccg caggtggggc gcacgctgtg   1020
ggaatctaga                                                          1030
```

```

<210> SEQ ID NO 19
<211> LENGTH: 1031
<212> TYPE: DNA
<213> ORGANISM: Bovine herpesvirus 1

<400> SEQUENCE: 19
aagcttcttc tcggcgggga cggccacgta cacttgctcg tcgtagaggc cgctgtgtac     60
cagcatgccc tcgcggctaa agaccaaaaa ggcgtttcgc agcgaggcgc caaaggggct    120
cagcagggcg gagacgtccg ccagctggcg gccgataagc gaggcgctcg cgattgggtt    180
```

```
gccgttgccg ccgtcggaca gaccggcggt gaggcgggcc tcgccttcgt cggcgcgcag    240
atgcgagggg ggctgcagca tcgcggcggg tgcttcggcg gcgctttcgc tcgcctctta    300
cgcgcgcggt cgcaaagcga gtctgcgctg cggcggcgct ctttatactg ggcggacgcc    360
cccgcagcgg caaaacacac actcggcggc ctcagcgtat caaacggcga cacgtttaag    420
tttcgacgcc tataagcggg cgcgcgcact aggcctccca atcggcaccg cgcgcggctg    480
tgcgggcgac cctgcgcaga gagagattaa tgatatcctt aagaaacgcg cgcatacgcg    540
agactggctt tcgttgacat ggaacatttt ttattcgcgg cgtgggggtg agaaggagga    600
ggaaaggcgg ggcgctctgg cagggcagcg ggggtgccct acaggtcgtt gattacggtg    660
cctgtgtagt tggtgctgcg gcgctcaaag aagttcgtgt gcttctcggc agtcatcagg    720
gccaaaggaa aatcggtccc aggaggcggg gtgccaaaca gaggaggcag ctggatagca    780
gcgagcaggc ggtccgcgct gtactcgacg tacgcagaaa tagcctccac gtcaagtata    840
tgactgccgc gcgcgcgcgca accaaataaa ctcgcgctca atttccacgc ttcgcggaac    900
agctcgtaga tgcgggccgg cggcggccgc tccccgccga ggtagttgtc gaagatgcag    960
cacgacgcgg ccgtgtgcac ggcttcgtcg cggctgatga ggtcgttggt ttggcacgtc   1020
acgactctag a                                                        1031

<210> SEQ ID NO 20
<211> LENGTH: 1022
<212> TYPE: DNA
<213> ORGANISM: Bovine herpesvirus 1

<400> SEQUENCE: 20
aagcttctct accctcctcc ctcgaggcag gcgcaacgga ccccgcccag tccatcccac     60
ttcgcacaat cgccaaattt ttgtccatta gctaaaagta tctccggcca taatcgatgt    120
gtctgagagg gtaataaaac acacccagac gctcggcact tagctctcga gtgattgcct    180
ggctgcttgc cccgtttgcg tggaatgagg ccaaacaagc atttggcccc tgtttggcta    240
gacggggctt tgtgtttttc ccaccccctgc ccttgcccct ggccgcctgg ccggccggct    300
aaagtatagg ccagaccaaa ccccccgcag cagctctgct cgctggcgag accccaaagc    360
gccaattgtg gcatatttcc gggtctgacc gcgcctgcac ttgcctttgg cagtaatatt    420
attaatgata tccttaagtc agagtttaat attacagaca gacaaaaagc cagataatta    480 caaagtatttt gttttttattg attgcgcatg cagaattcta gttagttagc atgcgcgagc    540
agttactttc ggtttgggga tgacagcggc gactgcggct cgaaagttaa gtatgcaggc    600
tgggggtcgc aaatacacgg cggtgcggtg tggtgggctg cgggtcgcgg agtgggtggg    660
cggggagccg gccgcggcga ttattgccgc caggcgctgc cgccgctgca gcggccgagc    720
agcccggcca ggctcgggcc ctggcgaccg cctggctgcg gcgccagggc cgcgctgctg    780
cggcgggggg tccccaggag gctttctcgc acccaggcgg ccacttccat ttcggtgcgc    840
cgcctcttct gcgccgagct ctcggggccg gggtccaggt cgccccgcgc catggcgctc    900
gctggccttc tctcccggcc ggggttgcca ttgcggccga cctcggcccg gcggctccg    960 gccagggccg gagcgccggc ccgccggggg tcggcggcag gggcgcggcc ggcgggtcta   1020
ga                                                                 1022

<210> SEQ ID NO 21
<211> LENGTH: 24
<212> TYPE: DNA
<213> ORGANISM: Artificial Sequence
```

```
<220> FEATURE:
<223> OTHER INFORMATION: Sequence encoding four repeats of -Gly-Ser-
      designed for insertion into a Bovine Herpes virus gene to
      construct a mutant gene (insertion mutant)

<400> SEQUENCE: 21
ggatctggta gtggctccgg gagc                                            24

<210> SEQ ID NO 22
<211> LENGTH: 8
<212> TYPE: PRT
<213> ORGANISM: Artificial Sequence
<220> FEATURE:
<223> OTHER INFORMATION: Peptide encoded by nucleotide designed for
      insertion into wild-type Bovine Herpes virus gene to create a
      mutant gene (insertion mutant)

<400> SEQUENCE: 22

Gly Ser Gly Ser Gly Ser Gly Ser
1               5

<210> SEQ ID NO 23
<211> LENGTH: 300
<212> TYPE: DNA
<213> ORGANISM: Bovine herpesvirus 1

<400> SEQUENCE: 23
atgccgcggt cgccgctcat cgttgcggtt gtggccgccg cgctgtttgc catcgtgcgc      60
ggccgcgacc cctagtaagc tttgctagac gcgatgcggc gcgaggggc aatggacttt      120 tggagcgcag gctgctacgc gcgcggggtg ccgctctcgg agccaccgca ggccctggtt     180
gttttttacg tggccctgac cgcggtaatg gtcgccgtgg ccctgtacgc gtacgggctt      240
tgctttaggc tcatgggcgc cagcgggccc aataaaaagg agtcgcgggg gcggggctga     300
```

BOVINE HERPES VIRUS-1 COMPOSITIONS, VACCINES AND METHODS

CROSS REFERENCE TO RELATED APPLICATIONS

This application claims priority to U.S. provisional application No. 61/195,102, filed Oct. 3, 2008, which is incorporated herein by reference.

BACKGROUND

Bovine herpesvirus 1 (BHV-1), is the causative agent of infectious bovine rhinotracheitis (IBR), and is an economically significant viral pathogen of cattle that can cause severe respiratory infection, conjunctivitis, abortions, vulvovaginitis, balanoposthitis, and systemic infection in neonate calves (Wyler et al. (1989) HERPESVIRUS DISEASES OF CATTLE, HORSES, AND PIGS 1-72 (Boston) In G. Witman (ed.) Kluwer Academic Publishers). The nucleotide sequence of the BHV-1 genome (136 kb) is known. It generally contains 67 unique genes and 2 genes, both duplicated, in the inverted repeats. In general, the BHV-1 genes exhibit homology at the amino acid sequence level to those of other alphaherpesviruses (HSV-1, VZV, EHV-1) and are arranged in similar order BHV-1 is a member of the varicellovirus genus, part of the subfamily Alphaherpesvirinae (family Herpesviridae). The subfamily includes human herpesvirus 3, pseudorabies virus, and bovine and equid herpesviruses.

BHV-1 infection is also a component of the upper respiratory tract infection referred to as "shipping fever" or bovine respiratory complex (Tikoo et al. (1995) Adv. Virus Res. 45:191; US patent publication no. 2004-0185056). BHV-1 is not the sole infectious agent associated with shipping fever, but it initiates the disorder by immunosuppressing infected cattle, which generally results in secondary bacterial infections and pneumonia increased susceptibility to secondary infection correlates with depressed cell-mediated immunity after BHV-1 infection (Carter et al. (1989) J. Virol. 63:1525; Griebel et al. (1990) J. Gen. Virol. 71:369; Griebel et al. (1987) Viral Immunol. 1:287; Griebel et al. (1987) Viral Immunol. 1:267). BHV-1 generally establishes lifelong latency in ganglionic neurons of the peripheral nervous system after initial replication in mucosal epithelium and results in animals being contagious beyond acute infection. Reactivation from latency generally results in virus shedding and transmission to other susceptible animals. Reactivation generally occurs after natural or corticosteroid-induced stress (Rock et al. (1992) J. Virol. 66:2484; Sheffy and Davies (1972) Proc. Soc. Exp. Biol. Med. 140:974).

In an effort to control BHV-1 infections, conventional killed-virus and attenuated live-virus vaccines have been developed. Commercially available vaccines, attenuated live-virus vaccines for example, may cause immunosuppression or immune depression, or other alterations of the host immune system. These alterations can be attributed to BHV-1 encoded proteins that suppress or otherwise alter the infected host's immune system. This immunosupression may result in the inability of these vaccines to prevent establishment of a latent infection by a virulent field strain of BHV-1 (see, e.g., Gerber et al. (1978) Am. J. Vet. Res. 39:753: Jericho et al. (1983) Can J. Com. Med. 47:133; Pastoret et al. (1980) Infect. Immun. 29:483).

A trend in current vaccines is co-administered or combination vaccines, which generally contain antigens from multiple agents or organisms. These vaccines can provide vaccination and protection for multiple agents and/or diseases and may be given in a single time point or administration. In vaccines containing BHV-1, BHV-1 may affect or change the host immune response against co-administered. In one example, the immune response to antigens co-administered with BHV-1 or present in combination vaccines along with BHV-1 may be suppressed, decreased, or otherwise changed, relative to the host immune response to those antigens when administered without BHV-1. The affected or altered immune response may reduce the ability of vaccine antigens co-administered with BHV-1 to stimulate an immune response protective against infection and/or disease caused by the infectious agents from which the co-administered antigens were derived. Prior and current attenuated BHV-1 viruses do not generally address BHV-1 immunosuppression and/or altered host immune responses against co-administered antigens.

SUMMARY

It has been found that BHV-1 viruses with modifications, and/or altered expression, of certain BHV-1 genes can relieve, prevent or reverse alterations of host immune responses (e.g., immunosuppression) attributed to BHV-1. It has also been found that BHV-1 viruses containing the modifications and/or alterations can relieve or prevent the alterations in host immune response to co-administered antigens or antigens administered in combination (e.g., suppressed immune response to additional antigens) as compared to BHV-1 viruses that do not have the modifications. Based on these findings, the following inventions are described.

In one example, compositions and vaccines containing a BHV-1 immunogen where at least one gene of the BHV-1 has been modified. In one example, the vaccine with the modified BHV-1 is administered with a non-BHV-1 immunogen either through co-administration or in a combination vaccine. The BHV-1 may be a modified live BHV-1 vaccine strain. In one example, the modified genes of the BHV-1 generally may be genes which encode proteins involved in the depression of the host immunological response during BHV-1 infection. The compositions and vaccines may also include modification such that the virulence of the BHV-1 has been reduced.

Examples of modified BHV-1 genes may include modified BHV-1 UL49.5, BHV-1 UL41, BHV-1 Us4, and BHV-1 Cir. The genes may be modified by single point mutations, in some cases with the single mutation being deletion mutations. Deletion mutations may be complete deletions or partial deletions of the genes. The modifications may result in production of no protein from that gene. The modifications may result in production of non-native or non-wild-type proteins from that gene. In one example, BHV-1 UL49.5 is modified. In one example, BHV-1 UL41 is modified. In one example, BHV-1 Us4 is modified. In one example, BHV-1 Circ is modified. Modification in other or additional genes is contemplated.

BHV-1 viruses containing gene modifications may contain one modification, two modifications, three modifications or lour or more modifications. These modifications may be in addition to modifications that may already exist, as in attenuated vaccine strains, for example. In one example, a BHV-1 virus may contain two modified genes that are UL49.5 and UL41. In one example, at least one gene selected from the group of BHV-1 UL49.5, BHV-1 UL41, BHV-1 Us4 and BHV-1 Circ and at least one gene selected from the group of BHV-1 LR-ORF 1, BHV-1 LR-ORF 2, and BHV-1 Us9 are modified.

In any of the composition and vaccine examples disclosed, a marker gene may be included, in certain embodiments, the marker genes may be BHV-1 UL49.5, BHV-1 UL41, BHV-1

Us4, and/or BHV-1 Circ. Certain compositions and vaccines may also include BHV-1 Us8 as the marker gene.

Figure 18:
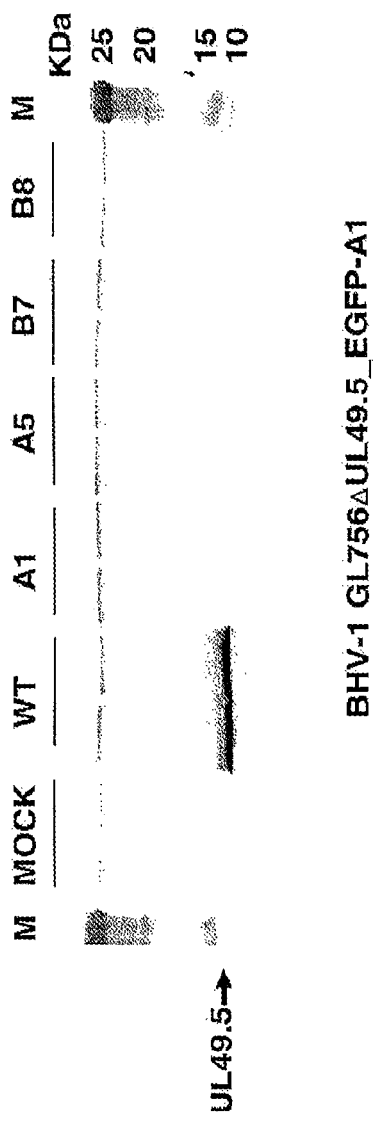

Disclosed vaccines may also include pharmaceutically acceptable vehicles. The compositions and vaccines may also include additional immunogens (e.g., an immunogen other than an BHV-1 immunogen). The additional immunogens may be co-administered or may be administered in a combination cocktail vaccine. Other administrations are contemplated. The additional immunogens may be bacterial immunogens, such as *Vibrio, Mannheimia haemolytica, Histophilus somni, Fusobacterium necrophorum, Clostridial, E. coli, Salmonella enterica, mycoplasma bovis,* and/or *Leptospirosis* immunogens, and/or viral immunogens such as BVD I and II. PI3 and BRSV immunogens, The compositions and vaccines may additionally include parasitic immunogens such as *Neospora caninum* and/or *Trichomonas* spp. immunogens.

Disclosed methods include prevention or treatment of a BHV-1 infection in a host (generally a bovine) by administering a therapeutic dose of the disclosed compositions or vaccines (e.g., BHV-1 containing modified gene or genes and at least one additional immunogen). Generally, the methods also include treatment or prevention of infection and/or disease by pathogens from which the additional immunogen or immunogens is/are obtained. In one example, administration of the disclosed compositions or vaccines facilitates immune responses in a host to or against BHV-1 and the additional immunogens, in one example, administration of the disclosed compositions or vaccines facilitates relieving or preventing immunosuppression of the host's immune responses attributed to BHV-1 that does not contain the modified genes. In one example, administration of the disclosed compositions facilitates relieving or preventing immunosuppression of the host's immune response to or against the additional immunogens attributed to unmodified BHV-1.

BRIEF DESCRIPTION OF THE DRAWINGS

In the accompanying drawings, which are incorporated in and constitute a part of the specification, embodiments of or related to compositions, vaccines and methods are illustrated, which, together with the detailed description given below, serve to describe the examples. It should be appreciated that the embodiments illustrated in the drawings are shown for the purpose of illustration and not for limitation. It should be appreciated that changes, modifications and deviations from the embodiments illustrated in the drawings may be may without departing from the spirit and scope of the invention, as disclosed below.

FIG. 1 illustrates DNA (SEQ ID NO:1) and amino acid sequences (SEQ ID NO:2) of Cooper strain BHV-1 UL49.5.

FIG. 2 illustrates DNA (SEQ ID NO:3) and amino acid sequences (SEQ NO:4) of Cooper strain BHV-1 UL41

FIG. 3 illustrates DNA (SEQ ID NO:5) and amino acid sequences (SEQ ID NO:6) of Cooper strain BHV-1 Circ.

FIG. 4 illustrates DNA (SEQ ID NO:7) and amino acid sequences (SEQ ID NO:8) of Cooper strain BHV-1 LR-ORF 1.

FIG. 5 illustrates DNA (SEQ ID NO:9) and amino acid sequences (SEQ ID NO:10) of Cooper strain BHV-1 LR-ORF 2.

FIG. 6 illustrates DNA (SEQ ID NO:11) and amino acid sequences (SEQ ID NO:12) of Cooper strain BHV-1 Us4. As described in the specification, the underlined nucleotides indicate the region that was deleted, in the Us4 gene from the GL756 strain of BHV-1 to produce the Us4 mutant used in some studies. Deletion of the underline nucleotides results in absence of the underlined amino acids when the gene is expressed.

FIG. 7 illustrates DNA (SEQ ID NO:13) and amino acid sequences (SEQ ID NO:14) of Cooper strain BHV-1 Us9.

FIG. 8 illustrates DNA (SEQ ID NO:15) and amino acid sequences (SEQ ED NO:16) of Cooper strain BHV-1 Us8.

FIG. 9 illustrates the DNA sequence (SEQ ID NO:23) of a UL49.5 mutant gene from the GL756 strain of BHV-1. The underlined nucleotides indicate sequences added to the wild-type GL756 UL49.5 sequence. The underlined nucleotides add two in-frame translational stop codons to the coding sequence.

FIG. 10 illustrates example flow cytometry data of BHV-1 GL756 effect on cell surface expression of MHC class I molecules. MDBK cells, mock-infected and infected with BHV-1 GL756 were stained with monoclonal antibody PT85A, specific for MHC class I molecules. Negative control cells were stained with MM605, a non-reactive, isotype matched control antibody.

FIG. 11 illustrates example data from a study where LkT antigen was administered to calves alone (LkT) or with BHV-1 (GL756+LkT) on day 0 and again on day 21 (LkT administered alone on day 21). Control calves were administered only BHV-1 (GL756) on day 0. Sera were obtained from the calves on the days indicated and the levels of antibodies specific for LkT was determined using ELISA. Error bars indicate standard error of the mean (SEM) for the measurements. The triangles indicate time points where there was a significant difference between the levels of LkT-specific antibodies in serum samples from GL756+LkT animals as compared to LkT animals.

FIG. 12 illustrates example data from a study where LkT antigen was administered to calves alone (LkT) or with BHV-1 (GL756+LkT) on day 0 and again on day 21 (LkT administered alone on day 21). Sera were obtained from the calves on the days indicated and the levels of IgG1 and IgG2 antibodies specific for LkT were determined using ELISA. The data are expressed as ratios of IgG1 versus IgG2. Error bars indicate SEM.

FIG. 13 illustrates example data from a study where LkT antigen was administered to calves alone (LkT) or with BHV-1 (GL756+LkT) on day 0 and again on day 21 (LkT administered alone on day 21). Control calves were administered only BHV-1 (GL756) on day 0. Peripheral blood was obtained from the calves on day 23. Cells within the blood samples were contacted with LkT antigen and, subsequently, IL-2 levels in the samples were determined using ELISA.

FIG. 14 illustrates example BHV-1 GL756Δ UL49.5 (A) and Us4Δ (B) Deletion-Recombination Constructs (DRC) used to generate deletion modifications by homologous recombination. Also illustrated are example DNA sequences of UL49.5 (SEQ ID NO:17) and Us4 (SEQ ID NO:18) recombination constructs.

FIG. 15 illustrates example DNA sequences of BHV-1 UL41 (SEQ ID NO:19) and BHV-1 LR-ORF 2 (SEQ ID NO:20) recombination constructs.

FIG. 16 illustrates example polymerase chain reaction (PCR) products from nucleotide amplification of BHV-1 GL756ΔUL49.5_EGFP clones A1 and B8, and background GL756 BHV-1, using flanking primers to the site of deletion/recombination.

FIG. 17 illustrates example polymerase chain reaction (PCR) products from nucleotide amplification of BHV-1 GL756ΔUs4_EGFP clones 1 and 2, and background GL756 BHV-1 using flanking primers to the site of deletion/recombination.

FIG. 18 illustrates an example Western blot of BHV-1 GL756ΔUL49.5 clones A1, A5, B7 and B8 or background GL756 BHV-1, using antibody against UL49.5. The Western blot confirms deletion of the target gene in the modified BHV-1.

Figure 19:
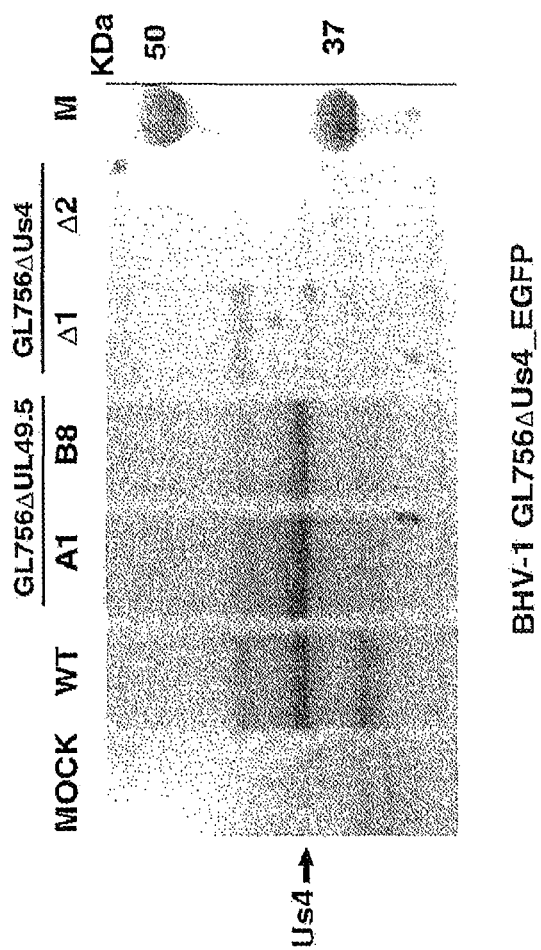

FIG. 19 illustrates an example Western blot, of BHV-1 GL756ΔUL49.5 clones A1, B8; GL756ΔUs4 clones 1, 2, or background GL756 BHV-1 using antibody against Us4. The Western blot confirms deletion of the target gene in the modified BHV-1.

Figure 20:
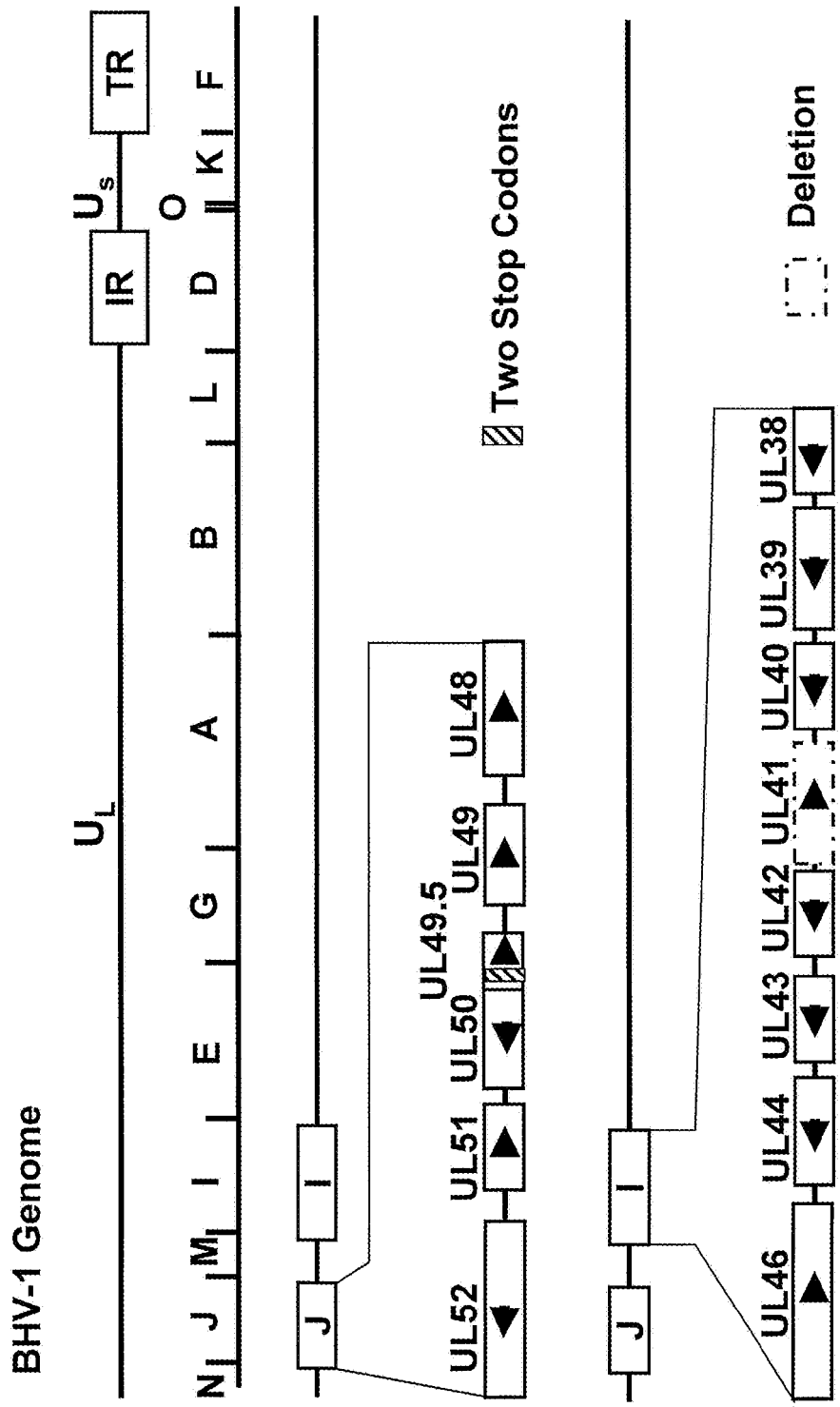

FIG. 20 illustrates the mutations within the UL49.5 (insertion of two stop codons) and UL41 (complete deletion) genes of the BHV-1 GL756 genome. In the upper part of the illustration is shown the unique ($U_L$ and $U_S$) and repeated (IR and TR) regions of the genome. In the lower part of the illustration is shown the UL49.5 gene within the J fragment, and the UL41 gene within the I fragment, of the genome.

Figure 21:
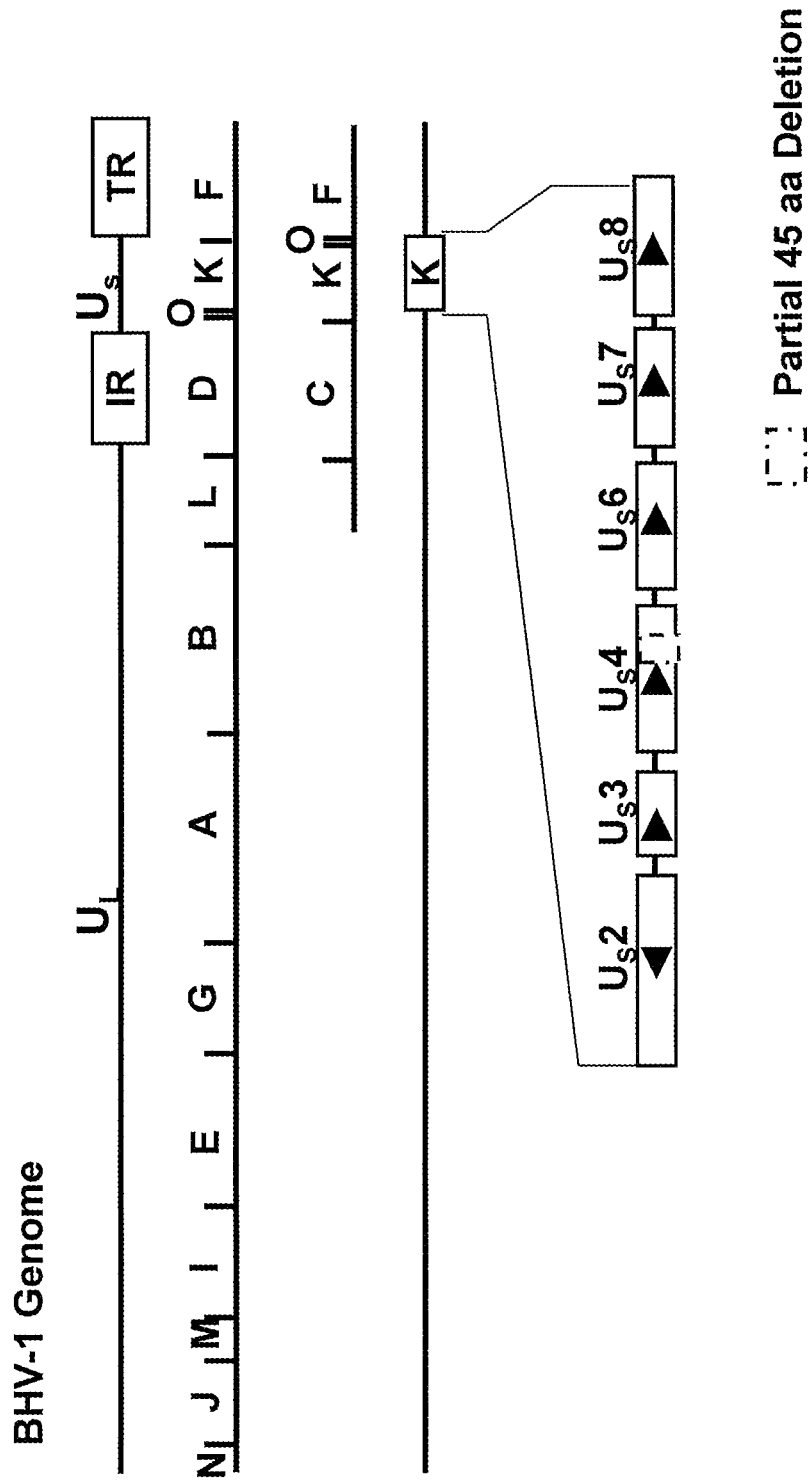

FIG. 21 illustrates the mutations within the Us4 gene (partial deletion and insertion) of the BHV-1 GL756 genome. In the upper part of the illustration is shown the unique ($U_L$ and $U_S$) and repeated (IR and TR) regions of the genome. In the lower part of the illustration is shown the Us4 gene within the K fragment of the genome.

Figure 22:
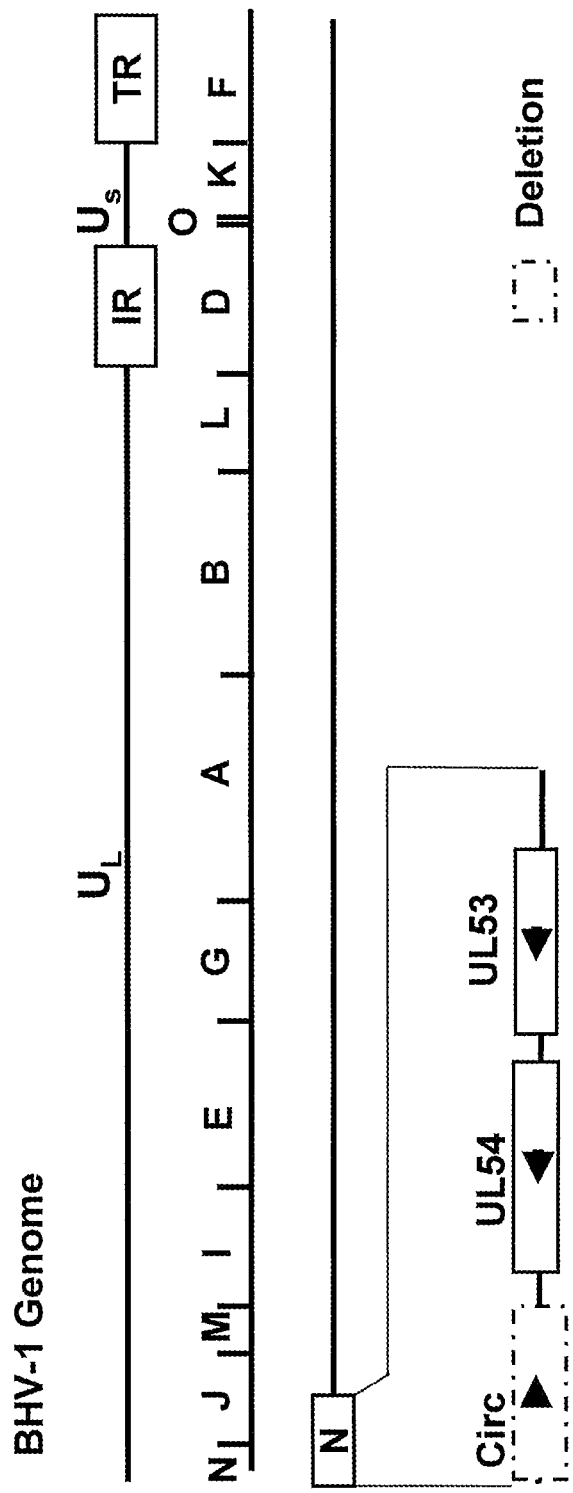

FIG. 22 illustrates the mutations within the Circ gene (complete deletion) of the BHV-1 GL756 genome. In the upper part of the illustration is shown the unique ($U_L$ and $U_S$) and repeated (IR and TR) regions of the genome. In the lower part of the illustration is shown the Circ gene within the N fragment of the genome.

Figure 23:
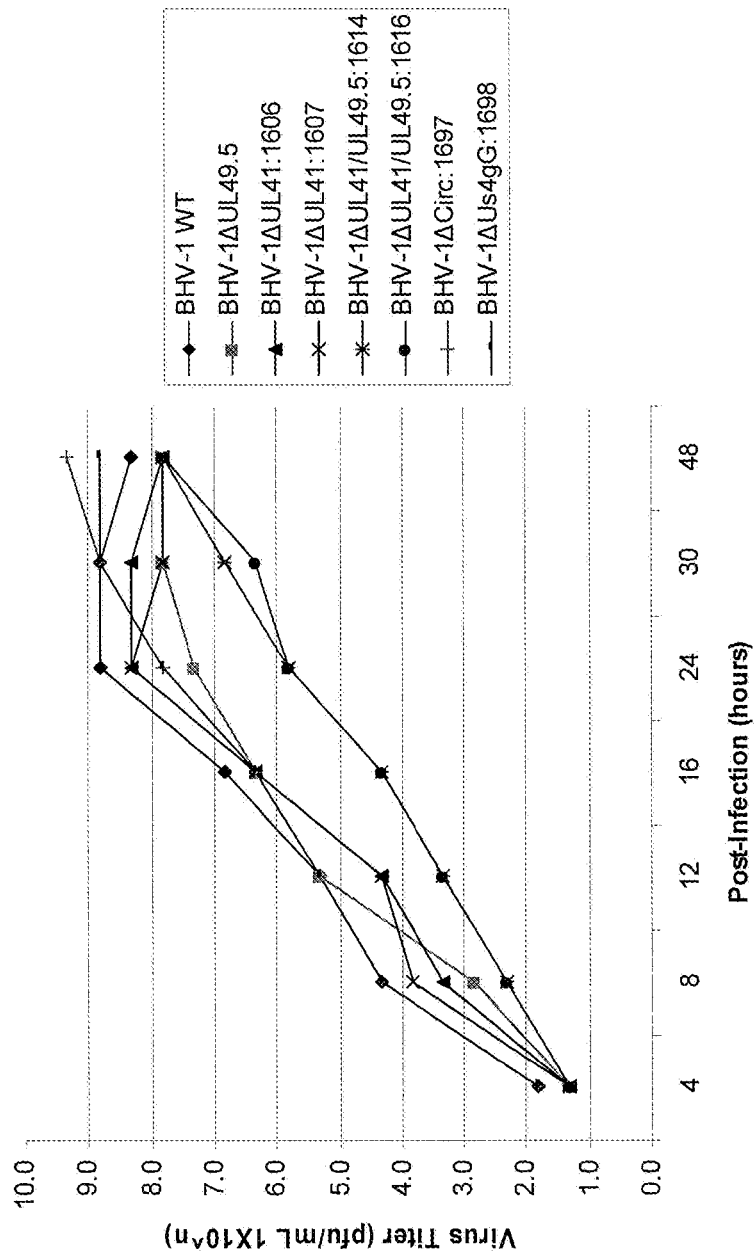

FIG. 23 illustrates growth curves of BHV-1 viruses on MDBK cells. The viruses had the GL756 background. GL756 (BHV-1 WT), UL49.5 mutant of GL756 (BHV-1ΔUL49.5), clones of two UL41 mutants of GL756 (BHV-1ΔUL41:1606 and BHV-1ΔUL41:1607), clones of two UL41/UL49.5 double mutants (BHV-1ΔUL41/UL49.5:1614 and BHV-1ΔUL41/UL49.5:1616), Circ mutant of GL756 (BHV-1ΔCirc:1697) and Us4 mutants (BHV-1ΔUs4gG:1698) were tested.

Figure 24:
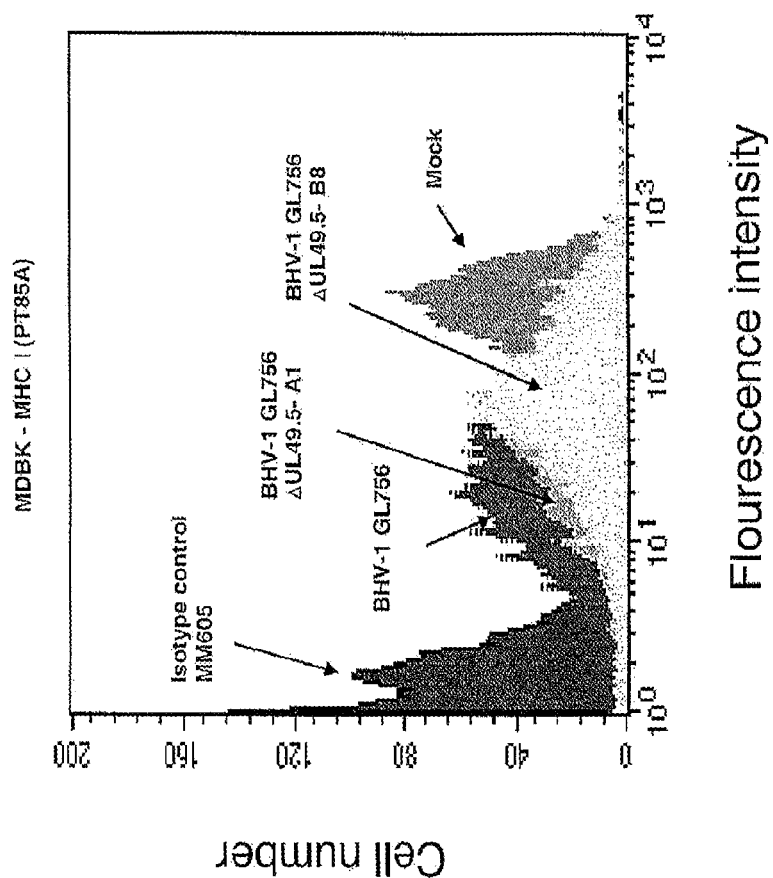

FIG. 24 illustrates example flow cytometry data of BHV-1 GL756 and modified effect on cell surface expression of MHC class I molecules. MDBK cells, mock-infected, infected with BHV-1 GL756 or GL756ΔUL4.5 clones A1 or B8 were stained with monoclonal antibody PT85A, an antibody specific for MHC class I molecules. Negative control cells were stained with MM605, a non-reactive, isotype matched control antibody.

FIG. 25 illustrates example flow cytometry data of the effect of BHV-1 GL576 and GL756ΔUL49.5-ΔUL41 on cell surface expression of MHC class I molecules. MDBK cells mock-infected, infected with BHV-1 GL756 or GL756ΔUL49.5-ΔUL41 were stained with monoclonal antibody PT85A, an antibody specific for MHC class I molecules. Negative control cells were stained with MM605, a non-reactive, isotype matched control antibody.

FIG. 26 illustrates example flow cytometry data of the effect of various mutant BHV-1 viruses on cell surface expression of MHC class I molecules. The data are expressed as percent expression compared to mock-infected cells (100%). MDBK cells were infected with BHV-1 GL576, GL756ΔUL49.5, GL756ΔUL41 or GL756ΔUL49.5-ΔUL41 and were stained with an antibody reactive with MHC class I molecules.

FIG. 27 illustrates example Western blotting data of the effect of various mutant BHV-1 viruses on expression of MHC class I molecules (top). The blots were scanned and quantified, and the data are expressed as percent expression compared to mock-infected cells (100%, bottom). MDBK cells were infected with BHV-1 GL576, GL756ΔUL49.5, GL756ΔUL41, GL756ΔUL49.5-ΔUL41, GL756ΔCirc or GL756ΔUs4.

FIG. 28 illustrates example flow cytometry data of the effect of BHV-1 and various mutant BHV-1 viruses on cell surface expression of MHC class II molecules. The data are expressed as percent expression compared to mock-infected, IFN-γ-treated cells (100%). MDBK cells were infected with BHV-1 GL576 (WT clone 1584), GL756ΔUL49.5 (clone 1610), GL756ΔUL41 (clone 1606), GL756ΔUL41 (clone 1607), GL756ΔUL49.5-ΔUL41 (clone 1614), GL756ΔUL49.5-ΔUL41 (clone 1616), GL756ΔCirc (clone 1697) or GL756ΔUs4 (clone 1698), incubated at 4° C. for 30 mins, then at 37'C for 1 hour followed by IFN-γ treatment At 72 hours post-infection, the cells were stained with monoclonal antibody CAT82A, specific for MHC class II. Negative control cells were unstained.

FIG. 29 illustrates example flow cytometry data of the effect of various mutant BHV-1 viruses on cell surface expression of MHC class II molecules. The data are expressed as percent restoration of MHC class II expression (i.e., MHC class II levels in GL576-infected cells given value of 0; restoration of MHC class II to the levels present in mock-infected cells would be given value of 100). IFN-γ-treated MDBK cells were infected with BHV-1 GL576 (WT clone 1584), GL756ΔUL49.5 (clone 1610), GL756ΔUL41 (clone 1606), GL756ΔUL41 (clone 1607), GL756ΔUL49.5-ΔUL41 (clone 1614), GL756ΔUL49.5-ΔUL41 (clone 1616), GL756ΔCirc (clone 1697) or GL756ΔUs4 (clone 1698) and were stained with an antibody reactive with MHC class II molecules.

FIG. 30 illustrates example data from a study where LkT antigen was administered to calves alone (LkT), with BHV-1 GL756 (GL756+LkT), with GL756ΔUL49.5-ΔUL41 or GL756ΔUs4 on day 0 and again on day 21 (LkT administered alone on day 21). Sera were obtained from the calves on the days indicated and the levels of IgG1 and IgG2 antibodies specific for LkT were determined using ELISA. The data are expressed as ratios of IgG1 versus IgG2. Error bars indicate SEM.

FIG. 31 illustrates example data from a study where LkT antigen was administered to calves with BHV-1 GL756 (LkT+GL756), GL756ΔUL49.5-ΔUL41 or GL756ΔUs4 on day 0 and again on day 21 (LkT administered alone on day 21). Peripheral blood was obtained from the calves on day 23. Cells within the blood samples were contacted with LkT antigen and, subsequently, IL-2 levels in the samples were determined using ELISA.

DETAILED DESCRIPTION

BHV-1 viruses are known to cause immunosuppression of infected hosts. When BHV-1 is administered to a host as a vaccine, it can also suppress or depress the immune response to an immunogen that may be administered with the BHV-1. This application describes BHV-1 viruses that immunosuppress infected hosts to a lesser extent than normal, wild-type BHV-1 viruses. The BHV-1 viruses disclosed here also can relieve the suppression or depression of the immune response to an immunogen that is administered with BHV-1. In some cases, there is no suppression of the immune response to an immunogen administered with the inventive BHV-1 viruses compared to an immune response raised when that immunogen is administered alone (without BHV-1). In some cases, there is an enhancement of the immune response to an immunogen administered with the inventive BHV-1 viruses compared to an immune response raised when that immunogen is administered alone. Also disclosed are compositions containing the inventive BHV-1 viruses and additional immunogens. Also disclosed are methods of using the inventive BHV-1 viruses, through co-administration to a host or through administration in a combination vaccine, to elicit an immune response in a host to BHV-1 and an additional immunogen.

The practice of the present invention will employ, unless otherwise indicated, conventional virology, microbiology, molecular biology and recombinant DNA techniques within the skill of the art. These techniques are explained fully in the literature.

All patents, patent applications and publications cited herein, whether supra or infra, are hereby incorporated by reference in their entirety. The following terminology will be used in accordance with the definitions set out below in describing the present invention.

Definitions

"Vaccine composition" and "vaccine" refer to an agent used to stimulate an immunological response in an animal so that current harm is alleviated, or protection against future harm is provided. A "co-administered vaccine" is a vaccine given or administered at the same approximate time but in a separate dose. As used herein, the same approximate time can be at any time between administration of the first dose and five days following administration of the first dose. A "combination" or "cocktail vaccine" is a vaccine that stimulates an immunological response to more than one pathogen which is manufactured with multiple immunogens and delivered in a single dose.

A "double-stranded DNA molecule" refers to the polymeric form of deoxyribonucleotides (adenine, guanine, thymine or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide when placed under the control of appropriate regulatory sequences. The boundaries of the coding sequence is determined by a start codon at the 5' (amino)terminus and a translation stop codon at the 3' (carboxy)terminus. A coding sequence can include, but is not limited to, procaryotic sequences, cDNA from eucaryotic mRNA, genomic DNA sequences from eucaryotic (e.g., mammalian) DNA, and synthetic DNA sequences. A polyadenylation signal and transcription termination sequence will usually be located 3' to the coding sequence. A polynucleotide is said to "encode" a polypeptide if in its native state or when manipulated by methods well known to those skilled in the art, it can be transcribed and/or translated to produce the mRNA for the polypeptide and/or a fragment thereof. The anti-sense strand is the complement of such a nucleic acid, and the encoding sequence can be deduced therefrom.

DNA "regulatory sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. This can be done to replace a codon with a redundant codon encoding the same or a conservative amino acid, while typically introducing or removing a sequence recognition site. Alternatively, it is performed to join together nucleic acid segments of desired functions to generate a desired combination of functions. A polypeptide produced as an expression product of an isolated and manipulated genetic sequence is an "isolated polypeptide", as used herein, even if expressed in a homologous cell type. Synthetically made forms or molecules expressing by heterologous cells are inherently isolated molecules.

"Recombinant polypeptides" refer to poly peptides produced by recombinant DNA techniques or recombinant, nucleic acid; i.e., produced from cells transformed by an exogenous DNA construct encoding the desired polypeptide.

A "promoter sequence" or "promoter" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate and properly regulate transcription at levels detectable above background. Within the promoter sequence will be found a transcription initiation site as well as protein binding domains responsible for the binding of RNA polymerase. Eucaryotic promoters will often, but not always, contain "TATA" boxes and "CAT" boxes. Procaryotic promoters may contain Shine-Dalgarno sequences in addition to the −10 and −35 consensus sequences.

"Operably linked" refers to a juxtaposition of components wherein the components so described are in a relationship permitting them to function in their intended manner. For instance, a promoter is operably linked to a coding sequence if the promoter affects the coding sequence's transcription or expression.

Two DNA or polypeptide sequences are "substantially homologous" when at least about 85% unless specifically stated otherwise, (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art.

The term "functionally equivalent" intends that the amino acid sequence of the encoded protein is one that will elicit a biological response equivalent to the biological response of the specified immunogen or protein, generally a native protein. In some cases, this biological response will be an immunological response. In some cases, this biological response refers to the ability of an encoded protein to suppress an immunological response in a host. "Non-functionally equivalent" refers to a biological response that is not equivalent to the biological response mediated by the native protein. Additionally, a gene sequence is functionally equivalent to another gene sequence if it encodes an identical polypeptide or a polypeptide that in itself is functionally equivalent.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like A "glycoprotein" is a glycosylated polypeptide.

"Native" proteins or polypeptides refer to proteins or polypeptides with sequences identical to those of wild-type BHV-1 proteins and fragments thereof. A "native" gene is a gene having a nucleotide sequence identical to a gene or fragment thereof found in wild-type BHV-1.

"Modification" of a gene as used herein means mutation, substitution or deletion of a nucleotide sequence encoding a gene or a fragment thereof for a BHV-1 protein, which results in a non-functionally equivalent BHV-1 protein as compared to background BHV-1 protein. A gene that has been completely deleted or has been partially deleted has also undergone modification. A gene that has been completely deleted generally does not encode a protein. A gene that has been partially deleted may encoded a modified protein. Modification of a gene may also include an insertion of one or more sequences into a gene. Modification of a gene may include combinations of individual types of modifications or mutations. In one example, part of a gene may be deleted and an additional sequence may be inserted at the location of the original deletion or at another location within the gene.

Protein sequences may also be modified. Modified proteins may be encoded by modified genes. A modified protein generally has a different amino acid sequence than the non-modified or native protein. In some cases, a modified protein will not have the same function as the native protein. In this case the modified protein may also be a non-functionally equivalent protein, as compared to background BHV-1. The modified protein may have amino acid mutations, substitutions or deletions as compared to background BHV-1. In certain embodiments, a gene or protein will be modified if it results in a protein that is not functionally equivalent to a wild-type gene or protein. Techniques to modify genes and protein, such as gene deletion constructs and bacterial artificial chromosomes (BACs) are well-known within the art and not meant to be limiting. Any method to modify the genes or protein sequences of the present invention may be used. For example, any modification technique that results in a non-functionally equivalent protein may be used. A gene modification may also include changes, not to the coding sequence of a gene, but to a regulatory sequence that affects level of expression of the gene. In one example, a modification of this type may result in down regulation of expression of a gene.

Within the context of this invention, the types of modifications that can be made in a specific gene may depend, in part, on the function of the encoded protein. In one example, the protein encoded by a particular BHV-1 gene may be known to suppress a host immunological response to an antigen administered with BHV-1. Therefore, it may be desired to delete the gene so that no protein is expressed from the gene (e.g., complete gene deletion). However, it may be that absent the protein encoded by the particular BHV-1 gene, the BHV-1 is too virulent to be used as a vaccine strain. One way, but not the only way, this may happen is if the protein encoded by the particular BHV-1 gene is a strong immunogen that, in part, stimulates a strong immunological response in the host. Absence of this protein from the virus may result in an inability of the host to mount a sufficient immunological response to keep the infecting virus in check. Disease or other deleterious side effects may occur in the host. One potential solution to this problem may be to modify the particular BHV-1 gene so the encoded protein is still immunogenic but is unable to suppress a host immunological response. In this way, the host may still be able to mount an immunological response sufficient to keep the infecting BHV-1 virus in check, but the function of the protein to suppress a host immunological response is disabled. There may be other scenarios where not every type of modification in a particular BHV-1 gene known to suppress the host immune system may be used. One of skill in the art will have knowledge of approaches to identify and solve this and similar problems.

As used herein, a "MHC related protein" is any protein directly involved in the pathway of antigen processing and presentation through a MHC class I or MHC class II molecule. These proteins are well known to those skilled in the art. Thus, a MHC related protein may be not only a MHC molecule but also, although not limited to, proteins active in the transport of antigens for MHC class I presentation such as transporter associated with antigen processing (TAP) proteins of a host animal.

A "marker gene" refers to a gene that can be used to differentiate infected animals from vaccinated animals. As used herein, marker genes differ from wild-type genes in a way that can be measured using a diagnostic test. A marker vaccine is a vaccine containing at least one marker gene. In one embodiment of the present invention, the marker genes will be either BHV-1 UL49.5, BHV-1 UL41, BHV-1 Us4, or BHV-1 Circ. In other embodiments, the marker gene may be BHV-1 Us8. Marker genes in vaccines may be used for a "DIVA" (Differentiating infected from Vaccinated Animals) vaccine as is known in the art. In one example, a diagnostic test may be designed and used to differentiate between an administered BHV-1 vaccine (DIVA vaccine) and a BHV-1 that has naturally infected the host "Mutant analog" of a BHV-1 protein or gene as used herein means a protein having an amino acid sequence or a gene having a nucleotide sequence either of which differs from the wild-type BHV-1 protein or gene sequence by one or more modifications.

A "host" refers to an animal capable of naturally acquiring BHV-1 infection. Thus, a host is one for which it may be desirable to immunize against BHV-1 infection, whether or not the host is already infected or latently infected by BHV-1. Generally the host is an ungulate. An ungulate host may be bovine, which includes cattle of any breed and any age. A bovine host encompasses calves as well as adult cattle, and is intended to include steers, bulls, heifers, cows and calves. Bovine or cattle may also include pregnant and lactating bovine animals. Veterinary applications are clearly contemplated by the present invention. In some embodiments, the compositions and vaccines of the present invention will not be given to a host that is pregnant, nursing, or under about three months of age. In certain embodiments, the compositions and vaccines of the present invention will be given to hosts that are at or around one month of age. In yet additional embodiments, the compositions and vaccines of the current invention will be given to pregnant animals. In these embodiments, the compositions and vaccines may be given to prevent fetal infection. In other embodiments, the composition and vaccines will not be given to a host within approximately 30 days of breeding.

An "antigen" refers to a molecule containing one or more epitopes that will stimulate a host's immune system to make a secretory, humoral and/or cellular antigen-specific response. The term is used interchangeably with "immunogen." The specific anti en can be a protein, a polysaccharide, a lipopolysaccharide, a lipopeptide or other molecules; or it can be a combination of any of these. Other combinations are possible. Particularly, the specific antigen can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; or it can include a recombinant nucleic acid expression product. Non-limiting examples of antigens include, without limitation, those that are capable of eliciting an immune response against viral bovine herpes virus, bovine respiratory virus, bovine viral diarrhea virus, bovine corona virus, and bacterial strains commonly associated with "shipping fever".

The term "effective amount of an immunogen" defines an amount of immunogen capable of eliciting a demonstrable humoral, secretory, and/or cell-mediated immune response. The appropriate amount of immunogen to be used is dependent on the specific immunogen and is well known in the art.

The term "epitope" refers to the site on an immunogen or hapten to which a specific antibody molecule binds or is recognized by T cells. The term is also used interchangeably with "antigenic determinant" or "antigenic determinant site."

An "immunological response" is the development in the individual of a cellular and/or antibody-mediated immune response. Usually, such a response includes but is not limited to one or more of the following effects; the production of antibodies, B cells, helper T cells, suppressor T cells, and/or cytotoxic T cells and/or γδT cells, directed specifically to an antigen or antigens included in the composition or vaccine of interest. There are many components that can result in the immune responses as defined by antibodies, B cells, T cells and the like, as described in the previous sentence. Measurement of these components may be used to infer whether or not a humoral, cellular, combination of humoral and cellular, or other response exists or is changed. For example, a humoral or cellular immune response, that may take the form of specific antibodies or antigen-specific cytotoxic T cells, respectively, may be affected by a variety of components. One component may be the ability of a specific epitope to be "presented" to T cells in the context of MHC class I and/or MHC class II molecules on the surface of antigen presenting cells (APCs) or other cells. Therefore, the presence or levels of MHC class I and/or MHC class II molecules may indicate the ability of an organism to mount a specific type of immune response. Also, changes in the levels of MHC class I and/or MHC class II molecules over time or in different situations may allow inference as to whether a specific type of immune response exists or can exist.

Another component of an immunological response is the ability of an antigen, that has already been presented to the immune system of an organism and has stimulated a primary immune response, to stimulate a secondary immune response or to "recall" the primary immune response. When an antigen is used to recall an immune response, various cytokines may be secreted by immune cells involved in the process. In one instance, measurement of changes in interleukin-2 (IL-2) may be used to infer whether and to what extent an immunogen has recalled a primary immune response. Recall of an immune response may be proportional to the amount of IL-2.

Related to a humoral immune response, one characteristic of whether this immune response exists and can be protective against a pathogen, for example, may the levels of serum antibodies that are specific for an antigen of the pathogen. In addition to levels of antibodies, the specific antibody isotypes or combination of isotypes or, for a given antibody isotype, the specific subtype or subclass, or combination or ratio of specific subtypes or subclasses may be informative. In one example, serum may contain different subtypes of the IgG isotype. The subtype IgG1 may be an antibody that is neutralizing for a specific antigen (and therefore thought to be protective). The subtype IgG2 may be an antibody that is not neutralizing for a specific antigen (and therefore not protective or less protective than the IgG1 subtype). In this example, therefore, a higher ratio of IgG1/IgG2 (for IgG specific for a given antigen) may indicate the potential for a better immunological response to a given antigen than a lower ratio of IgG1/IgG2.

An immunological response, or components of an immunological response, are usually measured with immunoassays. An increase in immunological response can be measured against the immunological response following wild-type BHV-1 infection or infection with commercially available BHV-1 vaccines. Depression of an immunological response can be measured as compared to infection with commercially available BHV-1 vaccines or uninfected cells. In some embodiments, depression of immunological response will be determined by evaluating MHC class I cell surface expression. In other embodiments, depression of immunological response will be determined by evaluating MHC class I cell cytoplasmic expression, with or without cell surface expression. In other embodiments, depression of immunological response will be determined by evaluating MHC class II expression. In additional embodiments, depression of immunological response will be determined by evaluating cytokines and other immune response indicators, such as measuring immunosuppression of a host response to co-administered immunogens as an indicator. Methods used to measure immunological response, and components of immunological responses, are well known in the art and not meant to be limiting.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity or cell mediated immunity to provide protection of an immunized host. An "immunogenic polypeptide" as used herein, includes the full-length (or near full-length) sequence of the inserted, protein or an immunogenic fragment thereof. By "immunogenic fragment" is meant a fragment of a polypeptide which includes one or more epitopes and thus elicits an antibodies that neutralize viral infectivity, and/or mediates antibody-complement or antibody dependent cell cytotoxicity or cell mediated immunity to provide protection of an immunized host. These fragments will usually be at least about 5 amino acids in length, and in certain embodiments at least about 10 to 15 amino acids in length. There is no critical upper limit to the length of the fragment, which could comprise nearly the full length of the protein sequence, or even a fusion protein comprising fragments of two or more subunit antigens.

The terms "treatment" and "treated" as used herein refer to the administration, to an individual of a composition which either prevents infection or reinfection (prophylaxis), or reduces or eliminates the symptoms of BHV-1 (therapy) or other diseases associated with additional immunogens. As used herein, treatment also occurs if the BHV-1 latency-reactivation cycle is reduced or prevented as measured by viral shedding following reactivation as compared to reactivation following infection of wild-type BHV-1. For example, an animal host has been treated if the amount of BHV-1 shed in feces either during primary infection or during latency is reduced or eliminated. An animal host has also been treated if the time of latency infection is reduced. Successfulness of this treatment may be measured by a reduction of ocular shedding or reduced shedding of infectious virus in the tonsil or TG.

"Latency-reactivation cycle" refers to the process of BHV-1 establishment of latency, maintenance of latency, and reactivation. Establishment of latency includes acute infection. Maintenance of latency is a phase that lasts for the life of the host and can be operationally defined as a period when infectious virus is not detected by standard virus isolation procedures. "Reactivation" and "reactivation from latency" refer to the process of viral reactivation following exogenous administration of corticosteroids or elevated levels of natural corticosteroids as a consequence of stress. Immunosuppression may also stimulate viral gene expression to cause reactivation. Upon reactivation, abundant viral gene expression may be detected in sensory neurons, and infectious BHV-1 virus can be isolated from trigeminal ganglia, eye swabs, and/or nasal swabs. During reactivation, virus is translocated back to the initial site of infection, from which it can spread to other susceptible hosts. The ability to reactivate from latency results in recurrent disease and virus transmission.

A virus has been "attenuated" when the strain of the virus has reduced pathogenicity and/or virulence such that it will initiate an immunological response without producing the specific disease. As used herein, a modified live vaccine (MLV) is a vaccine containing live virus that has been attenuated. In some embodiments, the vaccines of the invention will be further attenuated. An example further attenuated virus is one that has a reduction or elimination of the fever, lymphopenia, milk production drop, feed intake drop, abortion in naive pregnant cows and fatal viremia in calves less than 3 days of age as compared to vaccination with a conventional attenuated live-virus vaccine. In certain embodiments, BHV-1 virus will be further attenuated.

A "pharmaceutically acceptable vehicle" is formulated to be compatible with its intended route of administration and is interchangeable herein with the term "veterinary acceptable carrier" or "veterinary acceptable vehicle". Examples of routes of administration include parenteral, e.g., intravenous, intradermal, subcutaneous, oral (e.g., inhalation), transdermal (topical), transmucosal, rectal, and other administrations. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

A "deletion modification" or "deletion mutant" includes gene sequences with deletion of at least one nucleotide, generally in the open reading frame of a protein. As one of skill in the art will understand, in certain cases, a deletion mutation may include a point mutation. In certain embodiments, a deletion mutant has knocked-out or eliminated protein expression of the protein encoded by the modified nucleotide sequence. In other embodiments, a deletion mutant results in a protein, which although expressed, is not functionally equivalent, to wild-type protein. In some embodiments, deletion mutants will be missing the entire gene sequence. These deletion mutants may be called complete deletions. In other embodiments, the deletion mutants will be missing less than 1%, 1%-5%, 5%-10%, or more of the gene sequence. These deletion mutants may be called partial deletions. In certain embodiments, the deletion will be a point deletion as defined by deletion of a single nucleotide. A deletion modification or deletion mutant may also include more than one deletion of a single nucleotide.

A "reporter gene" can be any sequence the expression of which can be detected or measured, other than the coding sequence to which the promoter naturally is operably linked. Typically, the reporter gene is heterologous to the cell in which promoter activity is measured. Examples of reporter genes include, without limitation, genes that encode green fluorescent protein (or any other fluorescent marker), chloramphenicol acetyl transferase (cat), β-glucuronidase (gus), β-Galactosidase (lacZ), luciferase, and the like. Reporter gene expression can be measured by any of a number of conventional methods, and the optimal method will depend upon factors such as the nature and function of the reporter gene. In general, suitable assays of reporter gene expression include methods such as (i) assaying the function of a product of the reporter gene (e.g., measuring an enzymatic reaction catalyzed by a product of the reporter gene); (ii) measuring the level of protein expressed from the reporter gene (e.g., by SDS-PAGE or in an immunoassay using antibodies (e.g., polyclonal or monoclonal antibodies) that specifically bind to the product of the reporter gene); and (iii) measuring the level of mRNA transcribed from the reporter gene. Included within the invention are assays that permit high throughput screening of test compounds. In one example, expression of GFP or EGFP can be detected by visualization of green fluorescence in white light.

Modified BHV-1 Viruses

Broadly, in many embodiments, the present invention involves the modification of BHV-1 genes of modified live BHV-1 vaccine viruses so as to prevent or decrease the immunosuppression of the host seen in infection with BHV-1 wild-type or vaccine viruses. In one example, the BHV-1 modifications result in a virus that is less able or unable to decrease or suppress an immunological response specific to or against an immunogen that is administered with BHV-1. In one example, the BHV-1 modifications result in virus that, when administered with an additional, non-BHV-1 immunogen, results in an immunological response against the additional immunogen that is more robust than the immunological response that results when the additional immunogen is administered alone (without BHV-1).

Generally, the BHV-1 used in the invention is a live virus. This virus may or may not be attenuated. In certain embodiments, modified killed BHV-1 virus may be used. This invention also provides a method of relieving immunosuppression of host response to additional immunogens either co-administered and/or in a combination vaccine. The invention also provides a method of treating a host animal with the inventive vaccines.

The invention includes compositions and vaccines comprising modified BHV-1 genes wherein the genes are modified in order to treat depression of host immunological response during, bovine herpes virus infection and/or to relieve immunosuppression of host response to an additional immunogen either co-administered and/or in a combination vaccine. In most embodiments, vaccines to treat both BHV-1.1 and BHV-1.2 subtypes are encompassed by the invention. Methods of using the vaccines of the current invention are also envisioned. Many, but certainly not all. BHV-1 genes active in suppressing the immune system have cellular homologues, allowing them to be easily recognized. In certain embodiments, the modification will be in genes that play a role in MHC immunogen processing and presentation. MHC class I are antigen-presenting molecules found on all nucleated vertebrate cells, whereas MHC class II are antigen-presenting molecules found primarily on macrophages and B lymphocytes. Modifications may occur in genes involved with both MHC class I and MHC class II functions.

In many embodiments, modified BHV-1 genes will be genes that encode proteins that cause downregulation of the host MHC related proteins and or evade host immune response to the virus by evasion of the host immune system. Examples of these types of genes include BHV-1 UL49.5 [SEQ ID NO.:1], BHV-1 UL41 [SEQ ID NO.:3], and BHV-1 Circ [SEQ ID NO.:5].

In yet other embodiments, the modified genes encode proteins that suppress immune function though regulation of complement, action on cell growth and/or interference, with interferon expression. BHV-1 Us4 [SEQ ID NO.: 11] is believed to be immunomodulatory through its function as a chemokine binding protein.

The BHV-1 UL49.5 gene encodes a protein homologous to the highly conserved glycoprotein N (gN), found in all known herpesviruses. gN plays a role in down regulation of MHC class I on the cell surface, thus allowing BHV-1 to evade antigen presentation and activation of the host's immune system. Lipinska et al. (2006) J. Virol. 80:5822, hereby incorporated by reference, describes the BHV-1 UL49.5 gene in detail.

The BHV-1 UL41 gene encodes a protein homologous to tegument host shutoff protein or virion host shutoff (vhs). The tegument host shutoff protein appears to play a role in immunosuppression by down regulating, the expression of MHC Class I mRNA. Gopinath et al. (2002) Viral Immun. 15: 595, describes modification of BHV-1 UL41.

The BHV-1 Circ gene encodes a protein homologous to myristylated tegument protein. BHV-1 myristylated tegument protein appears to down regulate MHC Class II expression. Schwyzer et al. (2002) Vet. Microbiol. 86.165, describes Circ.

The BHV-1 Us4 gene encodes a protein homologous to glycoprotein(g)G, a chemokine binding protein. Bryant et al. (2003) EMBO J. 22:833, describes Us4.

The BHV-1 Us9 gene encodes a protein likely involved in anterograde transport from trigeminal ganglia to nasal sites during reactivation of latency.

The BHV-1 LR-ORF 1 and 2 genes or Latency Related ORF's are implicated in development of latent infection and viral persistence in trigeminal ganglia.

The BHV-1 Us8 gene encodes a protein homologous to glycoprotein(g)E, a protein thought to inhibit IgG-mediated immune response.

Modification of all of the above-named genes are contemplated by the disclosed invention.

In one embodiment, a modified BHV-1 virus may have a modification in a single gene. In other embodiments, a modified BHV-1 virus may have modifications in two, three, four, or even more separate genes. In many embodiments, modification of genes active in apoptosis will be in conjunction with modification of genes active in MHC processing and in these other embodiments, although not limiting, the modification may be in genes that either suppress immunological response through induction or suppression of apoptosis or programmed cell death. As a non-limiting example, modification may occur in UL49.5 and in LR-ORF 1 [SEQ. ID NO.: 7]. In still other embodiments, modification may occur in UL49.5, Us4, and in LR-ORF 1 or simply in UL49.5 and Us4. In still another embodiment, modification may occur in UL49.5 and UL41. It is understood that these embodiments are exemplary only and different combinations of immunosuppressive genes are contemplated by the invention. In certain embodiments, compositions will be chosen based on the ability of modified genes to act synergistically in stimulating immune response.

In certain embodiments, compositions and vaccines will include at least one modified BHV-1 UL49.5, BHV-1 Us4, BHV-1 UL41, and/or BHV-1 Circ. These modified genes are generally recognized to relieve immunosuppression. In some embodiments, all four genes will be modified. In other embodiments, one, two or three genes will be modified. The genes may be modified in any combination. As a non-limiting example, in compositions or vaccines where two of the genes have been modified, those genes may be BHV-1 UL49.5 and BHV-1 41, UL49.5 and Us4, UL41 and Us4, as well as BHV-1 Circ and BHV-1 UL49.5. In embodiments that include modifications in genes active in relieving immunosuppression, modifications in BHV-1 LR-ORF 1 and 2 [SEQ ID NO.: 9] and BHV-1 Us9 [SEQ ID NO.: 13] may also occur. Conversely, compositions and vaccines may exist where modifications have only occurred in BHV-1 LR-ORF 1 and 2 and/or BHV-1 Us9. It is understood that modification may occur in either BHV-1 LR-ORF 1 and 2 and BHV-1 Us9. BHV-1 LR-ORF 1 and 2 and BHV-1 Us 9 are thought to be active in the prevention/reduction of latency and the shedding of BHV-1. In yet other embodiments, marker genes may be modified either in conjunction with the modifications of the genes active in immunosuppression and/or the genes active in the prevention/reduction of latency and the shedding of BHV-1 or in conjunction with modification in both immunosuppression and latency genes. The marker gene may be BHV-1 Us8 [SEQ. ID NO.:15]. In a single embodiment, the vaccine may consist of three modifications in genes involved in immunosuppression, two modifications in genes involved in latency, and a marker gene. The only limitations on the combinations of modified genes are the resulting immunogens must be compatible both in the animal and in the vaccine preparation.

Methods for the preparation and evaluation of modified genes and proteins within the present invention are well known in the art. Non-limiting examples of modification techniques include modification of DNA sequences such that there is (1) substitution of one or more amino acids by another, for example, substitution by an isosteric residue having a different function, e.g., substituting Asn for Asp; a residue having an identical function but a different primary, secondary or tertiary structure, e.g., Asp for Glu; helix breakers such as Pro; substitution of glycosylated amino acids for non-glycosylated amino acids and the like or vice versa; replacing Cys with another residue to delete disulfide bridge formation; and (2) addition or deletion of one or more amino acids to produce isosteric, functional or structural differences in the proteins. Primary structure changes include hydrophobicity or hydrophilicity alterations, secondary structure changes include local folding alterations and tertiary structure changes include changes in the 3-D structure of a protein. In many embodiments, these structure changes will result in knocked out proteins or proteins unable to function equivalently to wild-type protein.

In some embodiments, the genes will result in immunosuppression from non-MHC related pathways e.g. Us4, UL41. In these other embodiments, although not limiting, the modification may be in genes that either suppress the immunological response through induction or suppression of apoptosis or programmed cell death. For example, when apoptosis occurs in leukocyte subsets, including CD4+ cells, the host's immune system is suppressed. Genes active in this apoptosis activation include bICP0 (Geiser et al. (2008) Microb. Pathog. 44: 459). In some embodiments, modifications will be in genes that encode bICP0 (Jones et al. (2006) Vet. Microb. 113: 199). In still other embodiments, modifications may be in the latency related genes such as BHV-1 LR-ORF 1 and 2 and BHV-1 Us49. Other non-MHC related pathways may include modification of genes such as BHV-1 LR-ORF 1 and BHV-1 Us9.

All of the embodiments of the present invention are envisioned as possible in different BHV-1 backgrounds. For example, the BHV-1 background may be the Cooper strain (wild-type) or conversely may be a strain such as BHV-1 GL756, found in commercially available vaccines. GL756 is an example of a conventionally derived modified live BHV-1 virus. Other conventionally derived modified live BHV-1 viruses are contemplated. These example strains are not meant to be limiting and the embodiments may use as background any BHV-1 strain capable of infecting a host. In the vaccines of the invention, the background BHV-1 will commonly be an attenuated or modified live virus. In certain embodiments, the background BHV-1 will be killed virus.

In certain embodiments, the depression of host immunological response will be measured against immunological response seen following wild type BHV-1 infection or infection with an additional immunogen. In alternative embodiments, the depression of host immunological response will be measured against BHV-1 GL756 infection or infection with BHV-1 Cooper Strain. A variety of methods of measurement of host immunological response, such as enzyme-linked immunosorbent assays (ELISAs) or measurement of MHC expression, are envisioned and well-known to those in the art.

In certain embodiments, the compositions of the invention are placed into a vector suitable for producing the BHV-1 containing modified genes in vivo. This vector may be built into a vaccine composition by the addition of a pharmaceutically acceptable vehicle and, optionally, an adjuvant. Such formulations are well within the skill of the art. Suitable vectors may include artificial chromosome constructs containing the modified genes. An example of an artificial chromosome is a bacterial artificial chromosome (BAC), e.g., pBeloBAC11 or pBAC108L; see, e.g., Shizuya et al. (1992) Proc. Natl. Acad. Sci. USA 89:8794; Wang et al. (1997) Biotechniques 23:992. The components of the artificial chromosome constructs can be assembled using standard methods. For example, the modified genes can be inserted into an artificial chromosome by co-transfection of cells with (i) a construct containing the artificial chromosome, flanked by sequences homologous to regions of the BHV-1 genome, and (ii) the BHV-1 genes, so that recombination takes place in the cells, resulting in production of a recombinant virus including the artificial chromosome. Recombinant BHV-1 can be isolated from cells in which an artificial chromosome construct and BHV-1 have been co-transfected, leading to production of a recombinant virus by homologous recombination, and the isolated BHV-1 can be manipulated to produce the BHV-1 modified genes, as desired. Direct cloning methods, employing unique sites in the BHV-1 genome and the artificial chromosome, can also be used to assemble the components of the artificial chromosome. For examples of artificial chromosomes with inserted foreign genes, see U.S. Patent Publication 2004-0171569, herein incorporated by reference. In the vaccine embodiments of the invention, the recombinant BHV-1 virus, produced upon introduction of the artificial chromosome construct into a cell, does not kill the cell. Specific instances of incorporation of specific modified BHV-1 genes into a viable virus are described in Examples 5 and 6 of this disclosure.

Formulations

The immunogenic compositions and vaccines employed herein as contemplated by the present invention can include one or more veterinary-acceptable carriers. Such veterinary acceptable carriers include any solvent, dispersion media, coating, adjuvant, stabilizing agent, diluent, antibacterial agent, antifungal agent, isotonic agent, adsorption agent, delaying agent and the like. As used herein, veterinary acceptable carriers and pharmaceutically acceptable carriers are used interchangeably.

Diluents can include, water, saline, dextrose, ethanol, glycerol, and the like. Isotonic agents can include sodium chloride, dextrose, mannitol, sorbitol, and lactose, among others, Stabilizers include albumin, among others.

A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity enhancing agents, such as sodium carboxymethylcellulose, sorbitol, or dextran. The vehicle may also contain minor amounts of additives, such as substances that enhance isotonicity and chemical stability, such as buffers and preservatives. Examples of buffers include phosphate buffer, bicarbonate buffer and tris buffer, while examples of preservatives include thimerosal, m- or o-cresol, formalin and benzyl alcohol. Standard formulations will either be liquid injectables or solids which can be taken up in a suitable liquid as a suspension or solution for injection. Thus, in a nonliquid formulation, the vehicle may comprise dextrose, human serum albumin, preservatives, etc., to which sterile water or saline could be added prior to administration.

Any pharmaceutically acceptable water soluble material or mixture of materials may be utilized in the invention. The pharmaceutically acceptable water soluble material may comprise one or more monosaccharides, disaccharides, polysaccharides or carbohydrates. Examples include dextrose, mannitol, fructose, polyfructosan, polydextrose, dextrin, glucose, invert sugar, lactitol, lactose, isomalt, maltitol, maltose, maltodextrin, sorbitol, xylitol, sucrose, sucralose, mannose, galactose, xylose, arabinose, fructose, glucosamine, galactosamine, rhamnose, 6-O-methyl-D-galactose, 2-O-acetol-beta-D-xylose, 2-acetamido-2-dioxy-beta-D-galactose-4-sulphate, N-acetylglucosamine, iduronate, mannuronate, methyl galacturonate, galactose, arabinose, alpha-D-manopyranose and biopolymers formed by covalent bonding between one or more monosaccharide or disaccharide units. Examples of carbohydrates include alginate, amylose, cellulose, carrageenan, pectin. For convenience, monosaccharides, disaccharides, polysaccharides and carbohydrates may be collectively referred to as "sugars". Other pharmaceutically acceptable materials that are well known in the art may also be utilized.

Various adjuvants, a field well-known in the art, can also be employed in the vaccine formulations of the present invention. Adjuvants may include, but are not limited to: mineral gels, e.g., aluminum hydroxide; surface active substances such as lysolecithin; glycosides, e.g., saponin derivatives such as Quil A or GPI-0100; pluronic polyols; polyanions; non-ionic block polymers, e.g., Pluronic® F-127 (B.A.S.F., USA); peptides; mineral oils, e.g. Montanide ISA-50, carbopol, Amphigen®, Amphigen® Mark II (Hydronics, USA), Alhydrogel® (BSA2; Accurate Scientific, Westbury, N.Y.), oil emulsions, e.g. an emulsion of mineral oil such as BayolF/Arlacel A and water, or an emulsion of vegetable oil, water and an emulsifier such as lecithin; alum, bovine cytokines; cholesterol; and combinations of adjuvants. Additional oil emulsions include a water in oil emulsion, and a water in oil in water emulsion. Other adjuvants or agents with immunostimulation or in immunomodulating or antigen presenting properties, and commercial products Impran™ (Boehringer Ingelheim Vetmedica, St. Joseph, Mo.), Emunade® (Schering-Plough Animal Health, Summit, N.J.), MetaStim® (Fort Dodge Animal Health, Overland Park, Kans.) and/or Emulsigen® (MVP Laboratories, Inc., Omaha, Nebr.) may also be used. Emulsigen D may also be used. In most embodiments, the type of adjuvant is not limiting as long as it does not interfere with Beef Quality Assurance™. Amounts and concentration of adjuvants and additives useful in the context of the present invention can readily be determined by the skilled artisan.

Adjuvants may be used in different ways depending on how the inventive vaccine is administered. For example, when the inventive BHV-1 and an additional, non-BHV-1 immunogen are co-administered (e.g., BHV-1 administered in one location and the additional antigen administered to another location of the host), the adjuvant may be administered with the additional immunogen, but not with the BHV-1. In other examples, adjuvant may be administered with the BHV-1, but not with the additional immunogen. Both the BHV-1 and additional immunogen may be administered with adjuvant or without adjuvant (e.g., in the case where BHV-1 and non-BHV-1 immunogens are administered in a combination cocktail). In some examples, BHV-1 may be administered with one adjuvant and additional immunogens may be administered with a different adjuvant.

In some embodiments, the vaccines of the present invention will be supplied in liquid form. In other embodiments, the vaccines will be supplied as a dry powder. In embodiments where the vaccine is supplied as a dry powder, the end user of the vaccine may reconstitute the vaccine using an appropriate diluent. Diluents are well-known in the art and can include, but are not limited to, substances such as sterile water. In some cases, the vaccine is preferably used within a certain period of time, such as 24 hours, once it has been reconstituted.

Administration and Additional Immunogens

Generally, the modified BHV-1 vaccines will be administered with at least one additional immunogen, either through co-administration and/or through administration of a combination vaccine. As used herein, an "additional immunogen" is an immunogen other than a BHV-1 immunogen. Further, in certain embodiments, an additional immunogen may not comprise a foreign gene inserted in to a BHV-1 vector. An additional immunogen can be in a co-administered vaccine or in a combination/cocktail vaccine, i.e. a vaccine with at least two types of immunogens. These additional immunogens may be a single immunogen from one or more particular pathogens (bacteria, mycoplasma, viruses, parasites, etc.) or may include a combination of more than one immuno en from one or more particular pathogens. The co-administered and/or combination vaccines can be whole or partial cell preparations and/or modified live preparations and such are commonly known by one of skill in the art. They may also include other immunomodulatory molecules. Non-limiting examples of pathogens and immunomodulatory molecules from which additional immunogens may be selected include, but are not limited to Bovine Viral Diarrhea Virus (BVDV); I, II and III; Bovine Respiratory Syncytial Virus (BRSV); Parainfluenza 3 Virus (PI3); *Mannheimia Haemolytica; Histophilus somni* (previously *Haemophilus somnus*) (*H. somni*); *Rotavirus* (BRV); *Coronavirus* (BCV); *Mycoplasma bovis; Leptospirosis; Neospora caninum; Trichomonas* spp. *Vibrio*; Clostridial antigens, *Pasteurella multocida; Fusobacterium necrophorum; E. coli* O157:H7; *Salmonella enterica* and immunomodulatory cytokines such as, for example interleukin-1α (IL-1 α), interleukin-1β (IL-1 β), interleukin-2 (IL-2), interleukin-4 (IL-4), granulocyte-macrophage colony stimulating factor (GM-CSF), and interferons.

As stated above, in certain embodiments, immunogens against BVD will be included in co-administered and/or combination vaccines. BVDV Types 1, 2 and 3 have been implicated in a variety of clinical syndromes. Studies have established that the virus causes severe primary respiratory disease; that persistently infected cattle are a major source of infection for susceptible calves; and that BVD infects white cell reservoirs, causing profound and broad-based deficits in the immune system. Furthermore, abortion or mummification can result when pregnant cattle become infected especially during the first trimester. Mucosal disease, another often fatal manifestation of bovine viral diarrhea (BVD), results from early fetal infection with a noncytopathic BVD biotype, development of immunotolerance to the virus, birth of a persistently infected calf, and subsequent superinfection with a cytopathic BVD biotype. BVD Type 2, was previously recognized chiefly as a hemorrhagic BVD isolate mostly in dairy herds.

In certain embodiments, additional immunogens against *Mycoplasma bovis* will be included in a co-administered and/or combination vaccine to prevent the clinical disease and losses associated with infections caused by *Mycoplasma bovis* in beef and dairy cattle. These diseases include contagious mastitis, respiratory pneumonia, joint infections (arthritic conditions), keratoconjunctivitis, and middle ear infections.

*Pasteurella multocida*, a bacterial cause of pneumonia in cattle, is another bacteria from which additional immunogens can be included in co-administered and combination vaccines.

*Mannheimia haemolytica* immunogens may include leukotoxin (LkT) or Outer Membrane Protein (OMP) associated antigens, or other antigens.

Additional bacterial immunogens against Leptospirosis are also envisioned in co-administered and combination vaccines. Leptospirosis, caused by bacteria of the genus *Leptospira*, is an economically important zoonotic infection of livestock. *Leptospira borgpetersenii* serovar *hardjo* (*L. hardjo*) and *L. interrogans* serovar *pomona* (*L. pomona*) are the two serovars most commonly associated with cattle leptosporosis worldwide in many cases, additional immunogens from these two serovars will be included in the co-administered and/or combination vaccine. Additional Leptospirosis immunogens include those from *Leptospira cannicola, Leptospira grippotyphosa*, and *Leptospira icterohaernorrhagiae*. Leptospiral infection of cattle may result in acute fever, agalactia, abortion, or birth of premature and weak infected calves, and may contribute to breeding failures and to conception rates.

Other bacterial pathogen foreign immunogens that ma be used in embodiments of the current invention come from *Vibrio* spp. and *Clostridial* species. Examples of *Clostridial* immunogens include those from *Clostridium chauvoei, Clostridium septicum, Clostridium novyi, Clostridium sordellii, Clostridium perfringens* Types C and D, and *Clostridium haemolyticum.*

In yet further embodiments, additional immunogens against *Neospora canimun* will be included in co-administered and/or combination vaccines. *Neospora caninum* is a cyst-forming protozoan which causes abortion in cattle. In cattle, abortion due to *N. caninum* infection usually occurs in mid to late gestation, although not all infected fetuses are aborted. Many congenitally infected calves are born healthy and persistently infected, although some infected calves are diseased at birth and die in the neonatal period with lesions similar to those of aborted calves.

*Trichomonas* is yet another parasite for which additional immunogens may be included in co-administered and/or combination vaccines.

In certain embodiments. BHV-1 co-administered and/or combination vaccines may include additional immunogens chosen from any combination of or from each of the bacterial, viral, parasitic, and immunomodulatory cytokine groups above. In other embodiments, the co-administered and/or combination vaccine may only include an additional immunogen from one of the groups above. In yet other embodiments, it is understood that co-administered and/or combination vaccines may include any number of multiple combinations of additional immunogens taken from the groups above. As an example, a combination vaccine may consist of immunogens of modified BHV-1, BVDV Type I and Type II, PI3, and BRSV. In one embodiment, a combination vaccine containing modified BHV-1, BVD I & II, *L. Pomona, Lepto hardjo-bovis, vibrio*, and *trichomonas* antigens will be used. This vaccine may be particularly useful in beef cattle females greater than one year of age. This example vaccine may be used in pregnant females for the prevention of fetal infection due to BVD I & II, the prevention BHV-1, abortion, prevention of early embryonic death due to *vibrio* and *L. hardjo bovis*, and prevention of *trichomonas* infection. In another embodiment, a combination vaccine containing antigens against modified BHV-1, BVD I & II, *L. Pomona, Lepto hardjo-bovis, vibrio*, and *Neospora* is envisioned. This vaccine may be particularly suiting for dairy cattle females over one year in age. In yet another embodiment, suitable for calves from one to six months of age, the combination vaccine may contain modified BHV-1, BVD I & II, BRSV, *M. haemolytica, H. somnus, Mycoplasma bovis, L. pomona*, and *Lepto hardjo-bovis* antigens. In some embodiments, calves younger than one month of age but older than one day of age will be vaccinated. For calves between the ages of six to twelve months, an example combination vaccine may contain antigens against modified BHV-1, BVD I & II, *M. haemolytica, H. somnus, Mycoplasma bovis, L. pomona*, and *Lepto hardjo-bovis*.

Example co-administered vaccines include those with additional immunogens to one or more of clostridial antigens, *Mannheimia haemolytica., Histophilus somni, Pasteurella multocida, Fusobacterium necrophorum, E. coli* O157:H7 and *Salmonella enterica*. In certain embodiments, the co-administered vaccine will be one against only *Clostridial* bacterin. In other embodiments, the co-administered vaccine will be against only *Histophilus Somni* bacterin, *Fusobacterium Necrophorum* bacterin, or *Salmonella Dublin-Typhimurium* bacterin.

As is understood by one of skill in the art, the only confines on co-administered and/or combination vaccines are that the individual components can be co-administered or administered as a combination vaccine to achieve the desired result of countering immunosuppression caused by BHV-1. In each of the vaccines contemplated by the present invention, it is also understood that any of the veterinary acceptable components, including but not limited to adjuvants, diluents, solvents, etc., described herein, may also be incorporated into the co-administered and/or combination vaccine.

It is understood that in certain embodiments, even though co-administered and/or combination vaccines may not elicit the same immunogenicity as individual vaccines, the co-administered or combination vaccine may still be preferred. In many instances, it is advantageous to administer a combination vaccine instead of administering several different vaccines as combination vaccines commonly reduce costs, both in terms of labor and materials. Furthermore, combination vaccines take less space, making them easier to transport and store.

Many protocols for administering the vaccine compositions of the present invention to host animals are within the skill of the art, including oral, intranasal, topical, transdermal, and parenteral. In certain embodiments, the route of administration is intranasally or parenterally, particularly intramuscularly. In certain embodiments, the formulations will be particularly adapted for intramuscular injection, as intravenous injection may not be practical for large-scale application to domestic animals. Nevertheless, other administration routes, such as subcutaneously or intradermal are envisioned as it may be unfavorable to administer intramuscularly in hosts slotted for food composition. Alternatively, the vaccines may be given orally and the subunits formulated with a pharmaceutically acceptable oral vehicle. In these embodiments, the vaccines of the present invention may be administered orally to raise mucosal immunity, as well as intramuscularly for systemic immunity.

For intranasal instillation, host animals can be inoculated with approximately 102 to 108 TCID50 of the respective modified live vaccine strains. For IM vaccination, the vaccine can be injected into the flank (caudal muscle, mass) or the neck (brachiocephalicus muscle) using 102 to 108 TCID50 of the virus. For subcutaneous administration, host animals can be inoculated with approximately 102 to 108 $TCID_{50}$ of the respective modified live vaccine strains. In many embodiments, vaccines will include at least 102.5 TCID50 of virus per dose. In certain embodiments, the vaccination may contain a dose volume of approximately 2 ml to approximately 5 ml. The routes of vaccination provided above are exemplary only, and any suitable means known in the art may be used in the practice of the present invention.

The concentration of the antigen(s) in the vaccine composition is selected so that an effective dose is presented in the host to elicit cell mediated immunity or antibodies to the polypeptide neutralizing epitopes. Within wide limits, the dosage is not believed to be critical.

Although optional, in certain embodiments, a second booster immunization will be administered to the animal host several weeks to several months after the initial immunization. In specific embodiments, such booster may be administered as late as one year after the initial immunization. To insure sustained high levels of protection against disease, it may be helpful to re-administer a booster immunization to the host animals on a periodic basis.

This periodic basis may range from monthly, to every six months, to yearly, to multiple years. In certain embodiments, the compositions will not be used in pregnant or nursing individuals. In certain other embodiments, the compositions will not be used in individuals that are within less than one week, one week, two weeks, three weeks, or four weeks of breeding. In yet other embodiments, the vaccine will not be used in animals slated for slaughter within 28 days or less.

Not meant to be limiting, beef animals may be commonly be vaccinated at branding (or pre turn out to summer pasture), weaning time, at time of delivery to a back-grounding facility (winter wheat pasture), and at arrival in a feedlot. For cows, fall weaning or pregnancy checking are also common times for vaccination. For dairy cattle, a common time for vaccination is at the time of drying off.

The present modified compositions and vaccines may be used as markers. Analysis of host animal samples can be used to determine if the host animal is protected by the vaccine of the invention and has not been exposed to a wild-type BHV-1 strain. In certain embodiments, the invention includes a method for determining the absence or presence and/or concentration of antibodies directed against BHV-1 genes and modified BHV-1 genes in a sample by employing an immunoassay, the immunoassay characterized by using modified BHV-1 immunogens reactive with BHV-1 antibodies as a reagent in the immunoassay, whereby a complex of the BHV-1 antibodies and the modified BHV-1 immunogen is formed, and determining the absence or presence and/or concentration of such a complex to determine if antibodies directed against such modified BHV-1 are present in a sample and, if present, to provide a means of determining their concentration. For example, the modified immunogens can be used as substrate reagents in immunoassays to identify antibodies to these BHV-1 proteins in a sample, e.g., blood, from a host animal as one means of determining if the host animal is infected with BHV-1 and to determine the concentration of the antibodies in the sample. BHV-1 immunogens can be mixed with or bound to a suitable matrix (support) or carrier, such as a latex particle, plastic microtitration plate or a similar material. They can also be conjugated with an enzyme, dye, radioisotope or similar material, depending upon shat immunological method is used. Immunoassays employing modified immunogens of BHV-1 within the present invention include, but are not limited to, radioimmunoassay, competition immunoassay, immunoprecipitation, enzyme-linked immunoadsorbent assay, immunofluorescence assay and the like. In any embodiments, detection is preferably convenient, rapid, sensitive and specific.

Described below are examples of the present invention which are provided only for illustrative purposes. The examples are not intended to limit the scope of the present invention in any way, as numerous embodiments within the scope of the claims will be apparent to those of ordinary skill in the art in light of the present disclosure. Those of ordinary skill in the art are presumed to be familiar with (or to have ready access to) the references cited in the application, and the disclosures thereof are incorporated by reference herein.

EXAMPLES

The following examples are for the purpose of illustrating an embodiment and is not to be construed as a limitation.

Example 1

BHV-1 Infection Caused Down Regulation of MHC Class I Molecules on Infected Cells To evaluate the effect of BHV-1 infection on MHC class I expression on the surface of infected cells, Madin-Darby bovine kidney (MDBK) cells were infected with BHV-1 GL756 strain at a multiplicity of infection (moi) of 10, or mock infected. At 16-24 hours post infection, the cells were stained with monoclonal antibody PT85A (VMRD, Inc.; Pullman, Wash., USA), specific for MHC class I molecules. Negative control cells were stained with a non-reactive, isotype matched control antibody (MM605; Dr. Subramaniam Srikumaran; Washington State University). The primary antibodies were either labeled with Zenon® Mouse IgG Labeling Kits (Molecular Probes, Invitrogen Detection Technologies, Carlsbad, Calif., USA) or fluorescently labeled secondary antibodies were used. The cells were then examined for surface immunofluorescence by flow cytometry.

In FIG. 10, the data show that cells infected with BHV-1 expressed MHC class I molecules on the cell surface but the levels of expression were decreased or down regulated as compared to mock infected cells. Therefore, wild-type BHV-1 decreased expression of MHC class I molecules on the surface of infected cells.

Example 2

BHV-1 Administration Caused a Suppressed Immune Response to an Additional, Co-Administered Immunogen in Calves To evaluate the effect of BHV-1 on the immune response to a non-BHV-1 immunogen co-administered to calves, the following study was performed. BHV-1 sero-negative calves (Hereford-Angus or Holstein-Dairy cross), 3-6 months of age, were used. The calves also had minimal amounts of LkT titers as measured by ELISA. Calves were subcutaneously administered in the neck either recombinant LkT from *Mannheimia haemolytica* alone (100 µg in 2 ml containing Emulsigen D adjuvant), BHV-1 alone (approximately $10^{5.5}$ BHV-1 GL756 strain in 2 ml) or LkT and BHV-1 (BHV-1 and LkT co-administered in the neck approximately 5 cm apart) on day 0. LkT was administered again on day 21 to the LkT alone and BHV-1 plus LkT groups of calves. Blood was drawn and sera collected prior to administration (day 0) and on days 4, 10, 14, 21, 28 and 35. Serum antibodies reactive with LkT were measured for each time point using ELISA. Levels of antibodies at the various time points were normalized to the levels for day 4, which were given values of 1.

Figure 11:
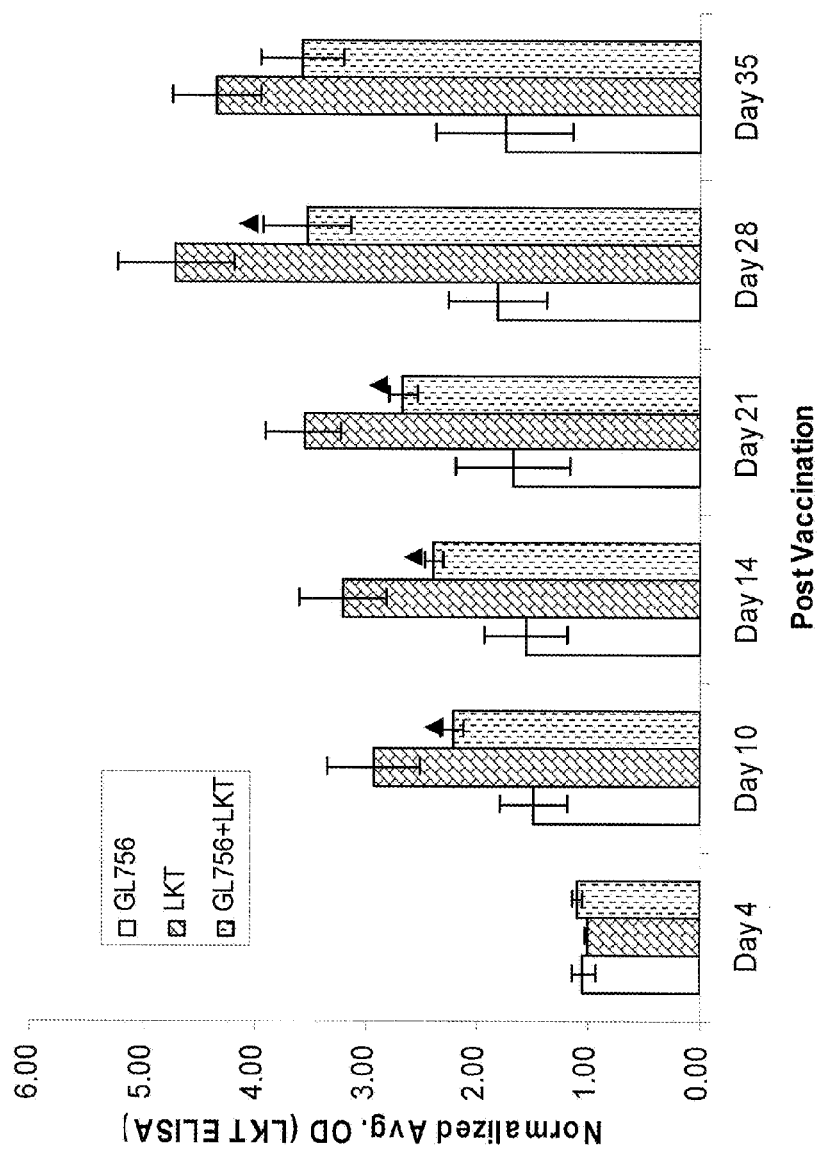

The results in FIG. 11 showed that levels of LkT-specific antibodies in the LkT alone and BHV-1 plus LkT groups generally rose during the time course of the study and peaked at 28-35 days. At all time points, the levels of LkT-specific antibodies present in the sera from calves administered LkT alone were greater than the levels of LkT-specific antibodies present in the sera from the calves administered BHV-1 plus LkT. Significant differences between the LkT alone and BHV-1 plus LkT groups were seen on days 10, 14, 21 and 28. These data indicated that the co-administered BHV-1 suppressed the immune response to a co-administered immunogen in the calves as compared to calves that were administered the immunogen alone.

Example 3

BHV-1 Administration Caused a Suppressed Ratio of IgG1 to IgG2 Subtypes for IgG Specific to a Co-Administered Immunogen in Calves To evaluate the effect of BHV-1 on IgG subtypes for IgG reactive with a non-BHV-1 immunogen co-administered with BHV-1, the serum samples from the groups administered LkT alone and BHV-1 plus LkT in the stud described in Example 2 were used. These serum samples were examined for LkT-specific IgG1 and IgG2 subtypes using ELISA plates coated with LkT and IgG subtype-specific antibodies.

Figure 12:
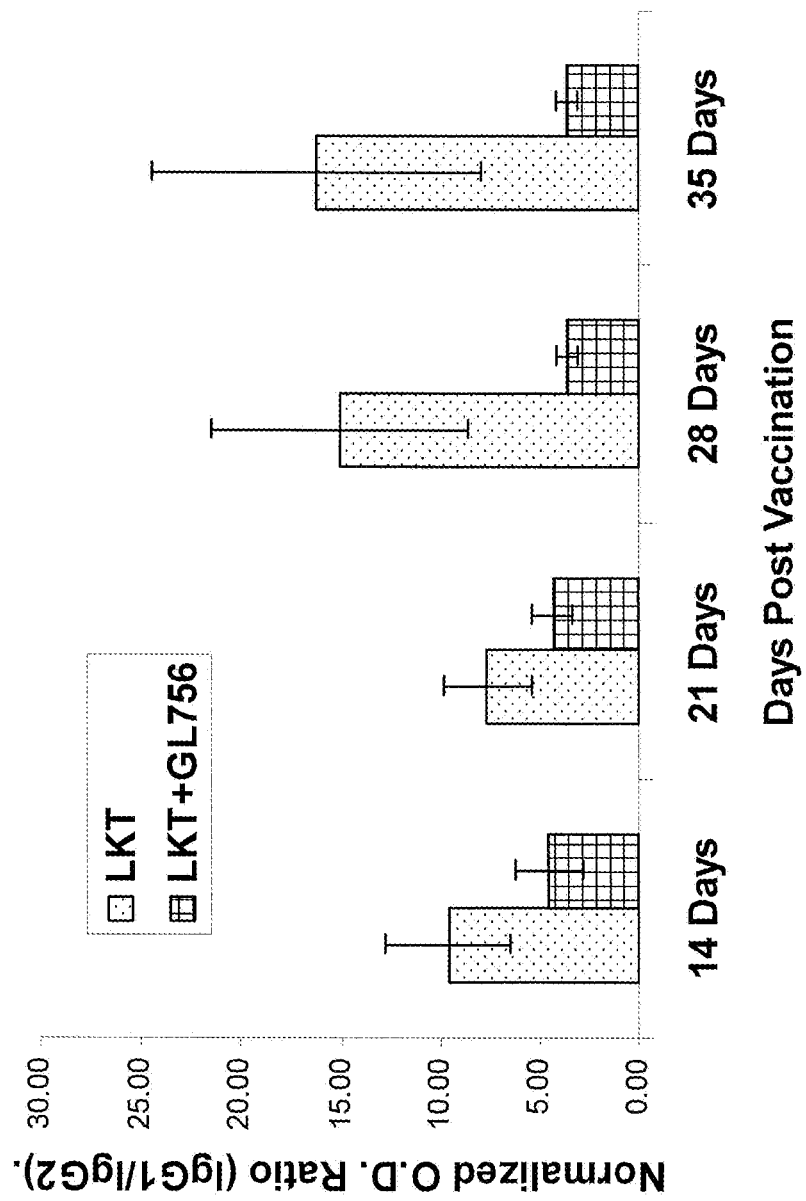

The results in FIG. 12 showed that the LkT-specific IgG1/IgG2 ratio for sera from calves administered LkT and BHV-1 was reduced compared to calves administered LkT alone. These data indicated that BHV-1 can alter (decrease) the IgG1/IgG2 subtype ratio for an immunogen administered along with BHV-1.

Example 4

BHV-1 Administration Caused a Suppressed Antigen Recall Response to a Co-Administered Immunogen in Calves To examine the effect of BHV-1 on antigen recall to a non-BHV-1 immunogen co-administered with BHV-1 (as measured by IL-2 production), blood was drawn from the calves used in the study described in Example 2 on day 23. The blood was diluted and LkT antigen was added to the samples. IL-2 levels were subsequently measured in the samples using ELISA.

Figure 13:
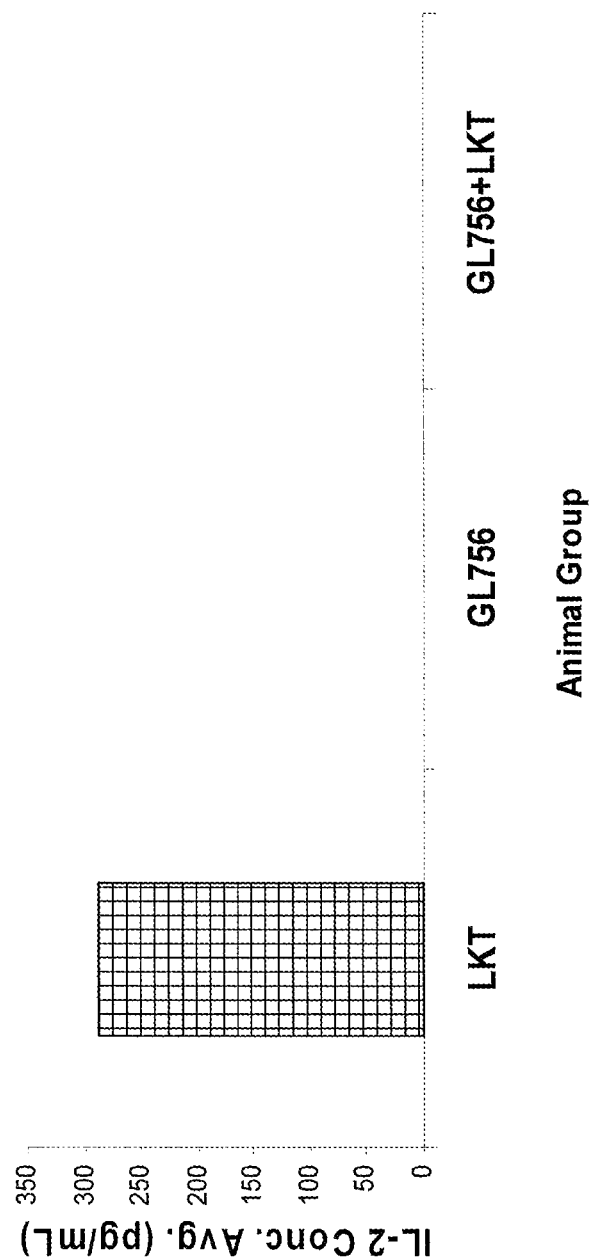

The results in FIG. 13 showed that IL-2 production in response to recall antigen was suppressed in samples from calves administered BHV-1 plus LkT, as compared to calves administered LkT alone. These data indicated that BHV-1 can suppress a recall response to an immunogen administered with BHV-1.

Example 5

Figures 1, 14:
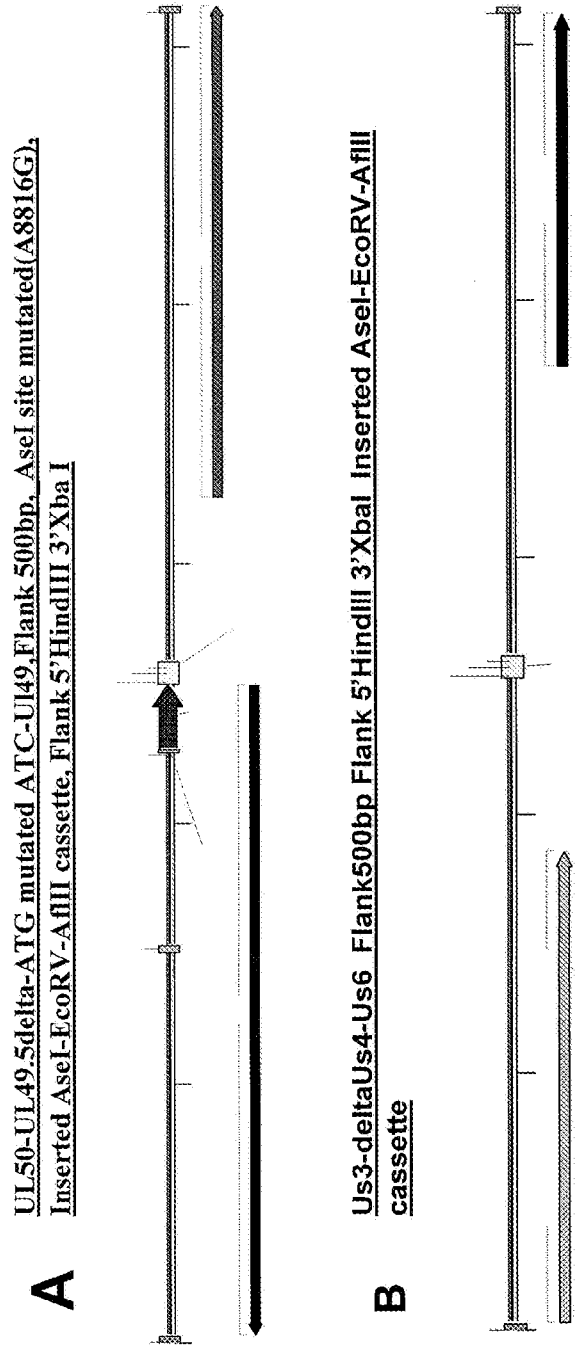
Figure 16:
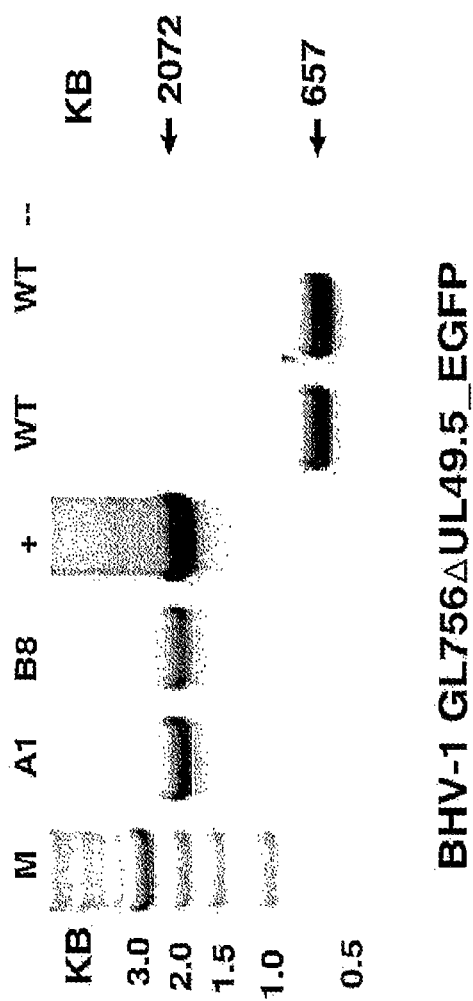
Figure 17:
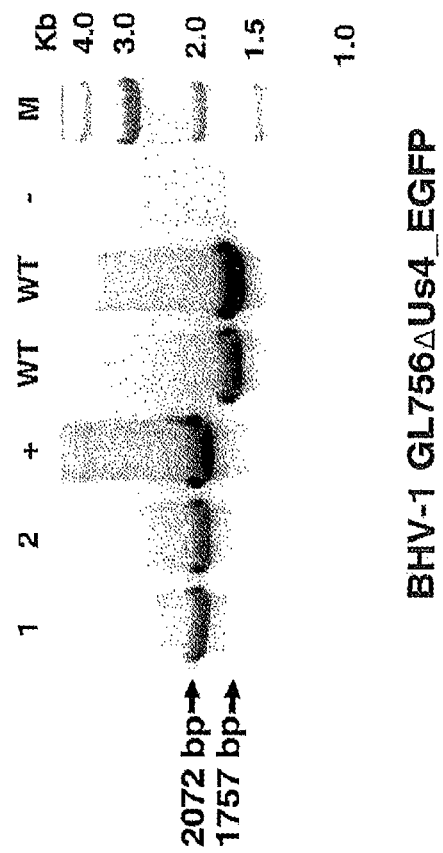

Construction of BHV-1 Deletion Mutants Using Deletion Recombination Constructs in Mammalian Cells BHV-1 GL756 deletion mutants for UL49.5, clones A1, A5, B7 and B8, were generated using deletion recombination constructs (DRC) as shown in FIG. 14A and in SEQ ID NO: 17 in FIG. 14. Enhanced Green Fluorescent Protein (EGFP) was inserted into the constructs to allow for isolation of recombinant viruses. DRC were transfected into MDBK cells and the cells were subsequently infected with BHV-1 GL756. Infected cell culture supernatant was diluted and plagued on new MDBK cells. Viral plaques exhibiting green fluorescence were isolated, plaque purified and identity confirmed by a recombinant polymerase chain reaction (PCR) screen. The PCR screen used primers flanking the site of deletion/recombination. Expected size of PCR product was 2072 base pairs (bp) for the mutants and 657 bp for the wild-type/parent virus. FIG. 16 shows the expected pattern for the A1 and B8 mutants.

Infected cell culture lysates were used to screen BHV-1 GL756ΔUL49.5 A1 and B8 by SDS-Polyacrylamide Gel Electrophoresis (PAGE) and Western blot to confirm deletion of the targeted gene. Expected size of the protein product from the UL49.5 gene is approximately 15 kDa in background virus. FIG. 18 shows that the A1, A5, B7 and B8 clones did not express the protein product of the UL 49.5 gene. Mock infected cells were used as the control.

BHV-1 GL756 deletion mutants for Us4, clones 1 and 2, were generated using deletion recombination constructs (DRC) as shown in FIG. 14B and in SEQ ID NO: 18 in FIG. 14. EGFP was inserted into the constructs to allow for isolation of recombinant viruses. DRC were transfected into MDBK cells and the cells were subsequently infected with BHV-1 GL756. Infected cell culture supernatant was diluted and plagued on new MDBK cells. Viral plaques exhibiting green fluorescence were isolated, plaque purified and identity confirmed by PCR screen. The PCR screen primers flanking the site of deletion/recombination. Expected size of PCR product was 2072 bp for the mutants and 1757 bp for the wild-type/parent virus. FIG. 17 shows the expected pattern for the 1 and 2 mutants.

Infected cell culture lysates were used to screen BHV-1 GL75ΔUs4-1 and 2 by SDS-PAGE and Western blot to confirm deletion of the targeted gene. Expected size of the protein product from the Us4 gene is approximately 40 kDa in background virus. FIG. 19 shows that the 1 and 2 clones did not express the protein product of the Us4 gene. Mock infected cells were used as the control.

Example 6

Construction of BHV-1 Deletion Mutants Using Bacterial Artificial Chromosome Constructs in Mammalian Cells A procedure using bacterial artificial chromosome constructs (BAC) was used to generate BHV-1 mutants used in some studies. The procedure has been described in Tischer et al. (2006) BioTechniques 20:191. In general, the procedure uses recombinant transfer plasmids that contain the mutation desired to be placed into BHV-1 which is flanked by wild-type BHV-1 sequences. The recombinant transfer plasmids contained the gene encoding Green Fluorescent Protein (GFP) and also a bacterial origin of replication. The recombinant transfer plasmids were transfected into MDBK cells and subsequently infected with BHV-1 GL756. Infected cell culture supernatant was diluted and plaqued on new MDBK cells. Viral plaques exhibiting green fluorescence were isolated, plaque purified and the viral DNA was electroporated into *E. coli* cells. DNA from the transformed *E. coli* clones was screened by restriction digests and Southern blotting to obtain the desired BHV-1 mutants. Unwanted GFP and bacterial replication origin sequences were then removed from the BHV-1 mutant clones using en passant mutagenesis, as described in the Tischer et al. reference. This method uses Red-catalyzed insertion to create a sequence that is excised, along with the GET and bacterial origin sequences, in a subsequent Red-catalyzed step. The resulting BHV-1 clones were transfected into MDBK cells and infectious mutant virus stocks were obtained.

Five different BHV-1 mutant or modified viruses were produced using the above procedures. All BHV-1 mutant viruses were made in the GL756 strain background. One mutant BHV-1 virus contained a modification in the UL49.5 gene. The DNA sequence of the UL49.5 mutant is shown as SEQ ID NO: 23 in FIG. 9. The underlined nucleotides in the DNA sequence illustrated in FIG. 9 indicate nucleotides that were inserted into the GL756 wild-type UL49.5 sequence. The underlined nucleotides add two in-frame translational stop codons to the coding sequence. The proteins translated from this gene are truncated.

Another mutant BHV-1 virus contained a complete deletion of the UL41 coding sequence. A third mutant BHV-1 virus contained both of the already described UL49.5 and UL41 mutations. Therefore, this particular BHV-1 contained modifications in two genes, UL49.5 and UL41. FIG. 20 illustrates the locations of the UL49.5 and UL41 gene regions within the BHV-1 genuine, as well as the above-described modifications.

A fourth mutant BHV-1 virus contained a partial deletion of the Us4 coding sequence, but also an insertion of a new sequence into the location of the deletion. The DNA (SEQ ID NO: 11) and amino acid (SEQ ID NO: 12) sequences of the Us4 gene from the Cooper strain of BHV-1 are illustrated in FIG. 6 and are the same as the Us4 gene from the GL756 strain. The underlined nucleotides illustrated in the DNA sequence of FIG. 6 are the nucleotides that were deleted in the BHV-1 Us4 mutant. Deletion of these nucleotides resulted in deletion of the underlined amino acids in the amino acid sequence of FIG. 6. The deletion was an in-frame deletion. Therefore, the amino acid sequence encoded by nucleotides downstream of the deletion are the same as those encoded by nucleotides of the wild-type Us4 sequence.

In addition to these deletions, the Us4 mutant gene also had an insertion of 24 nucleotides (GGATCTGGTAGTGGCTC-CGGGAGC; SEQ ID NO: 21) into the region where the above-described deletion was located. These 24 nucleotides encoded the amino acid sequence Gly Ser Gly Ser Gly Ser Gly Ser (SEQ ID NO: 22). Because the insertion was an in-frame deletion, the protein encoded by the modified Us4 gene contained the Gly Ser Gly Ser Gly Ser Gly Ser amino acids in place of the underlined amino acids shown in SEQ ID NO: 12 illustrated in FIG. 6. FIG. 21 illustrates the location of the Us4 gene region within the BHV-1 genome, as well as the modification.

A fifth mutant BHV-1 virus contained a complete deletion of the Circ coding sequence. FIG. 22 illustrates the location of the Circ gene region within the BHV-1 genome, as well as the modification.

Example 7

Growth of BHV-1 Viruses Containing Modifications

To examine the effect of modifications within genes of interest on growth properties of the BHV-1 virus, MDBK cells were infected with the viruses described in Example 6, and virus titer was determined at various times thereafter. Viruses examined included BHV-1 with none of the described modifications (GL756; BHV-1 WT), with the modification in UL49.5 (BHV-1ΔUL49.5), two different clones of BHV-1 with the modification in UL41 (BHV-1ΔUL41:1606 and BHV-1ΔUL41:1607), two different clones of BHV-1 with the modifications in both UL49.5 and UL41 (BHV-1ΔUL41/UL49.5:1614 and BHV-1ΔUL41/UL49.5:1616), with the modification in Circ (BHV-1ΔCirc:1697), and with the modification in Us4 (BHV-1ΔUs4gG:1698).

The results in FIG. 23 show that all of the tested BHV-1 viruses with modifications had growth kinetics similar to the BHV-1 with no modifications. These data indicated that modifications in the tested genes did not affect the growth properties of the virus.

Example 8

Restoration of MHC Class I Expression on Infected Cells by Infection with BHV-1 Viruses Containing Modifications To evaluate the effect of BHV-1 viruses containing modifications on expression of MHC class I on the surface of infected cells, MDBK cells were infected with the modified BHV-1 viruses described in Example 5 (data for these experiments shown in FIG. 24) or the modified BHV-1 viruses described in Example 6 (data for these experiments shown in FIGS. 25-31). For the experiments where MHC class I expression was examined, as described in this example, MDBK cells were infected by the viruses at an moi of 10, or were mock infected. At 16-24 hours post infection, the cells were stained with monoclonal antibody PT85A (VMRD, Inc.; Pullman, Wash., USA), which is specific for MHC class I molecules. Negative control cells were stained with a non-reactive, isotype control antibody (MM605; Dr. Subramaniam Srikumaran, Washington State University). The primary antibodies were either labeled with Zenon® Mouse IgG Labeling Kits (Molecular Probes, Invitrogen Detection Technologies; Carlsbad, Calif., USA) or fluorescently labeled secondary antibodies were used. The cells were then analyzed for surface fluorescence by flow cytometry.

Figure 25:
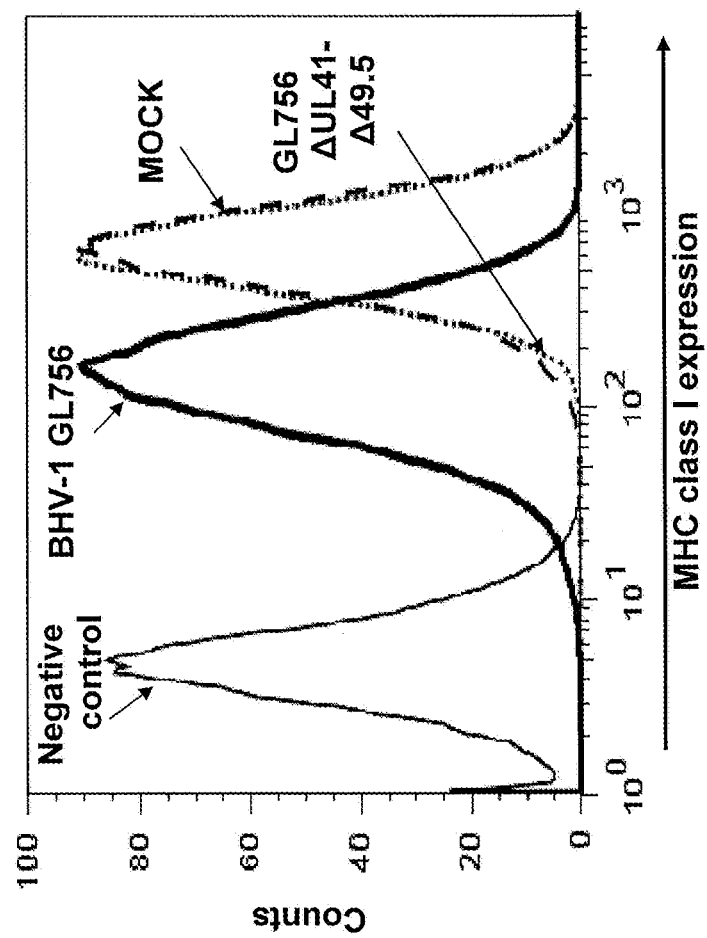

In FIG. 24, the data showed that cells infected with BHV-1ΔUL49.5 A1 or B8 (as described in Example 5) had partially reversed or restored MHC class I expression on the cell surface as compared to cells infected with BHV-1 not containing modification in the UL49.5 gene (BHV-1 GL756). In FIG. 25, the data showed that cells infected with BHV-1GL756ΔUL41-ΔUL49.5, containing modifications in both UL49.5 and UL41 (as described in Example 6) had fully reversed or restored MHC class I expression on the cell surface as compared to cells infected with BHV-1 not containing, the modifications (BHV-1 GL756). These data indicated that the BHV-1 viruses containing these modifications did not cause down regulation of MHC class I molecule expression, or at least did not cause down regulation of MHC class I to the extent that unmodified BHV-1 viruses caused down regulation of MHC class I expression.

Figure 26:
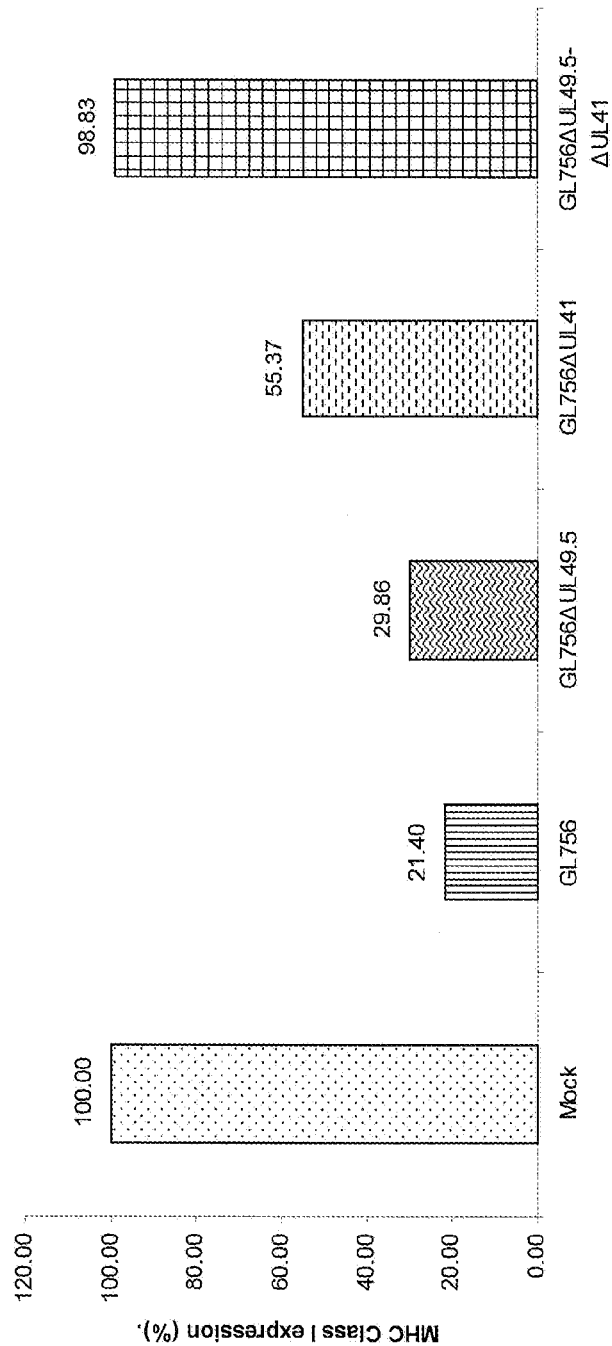

In FIG. 26, the data showed that cells infected with BHV-1 GL756ΔUL49.5, containing modification in UL49.5 (as described in Example 6), and with BHV-1 GL756ΔUL41, containing modification in UL41 (as described in Example 6), partially reversed or restored MHC class I expression on the surface of infected cells as compared to cells infected with BHV-1 GL756 that did not contain modifications. The data also showed that cells infected with BHV-1 GL756ΔUL49.5-ΔUL41, containing modifications in UL49.5 and UL41, fully reversed or restored MHC class I expression on the cell surface of infected cells as compared to cells infected with BHV-1 GL756 that did not contain the modifications.

Figure 27:
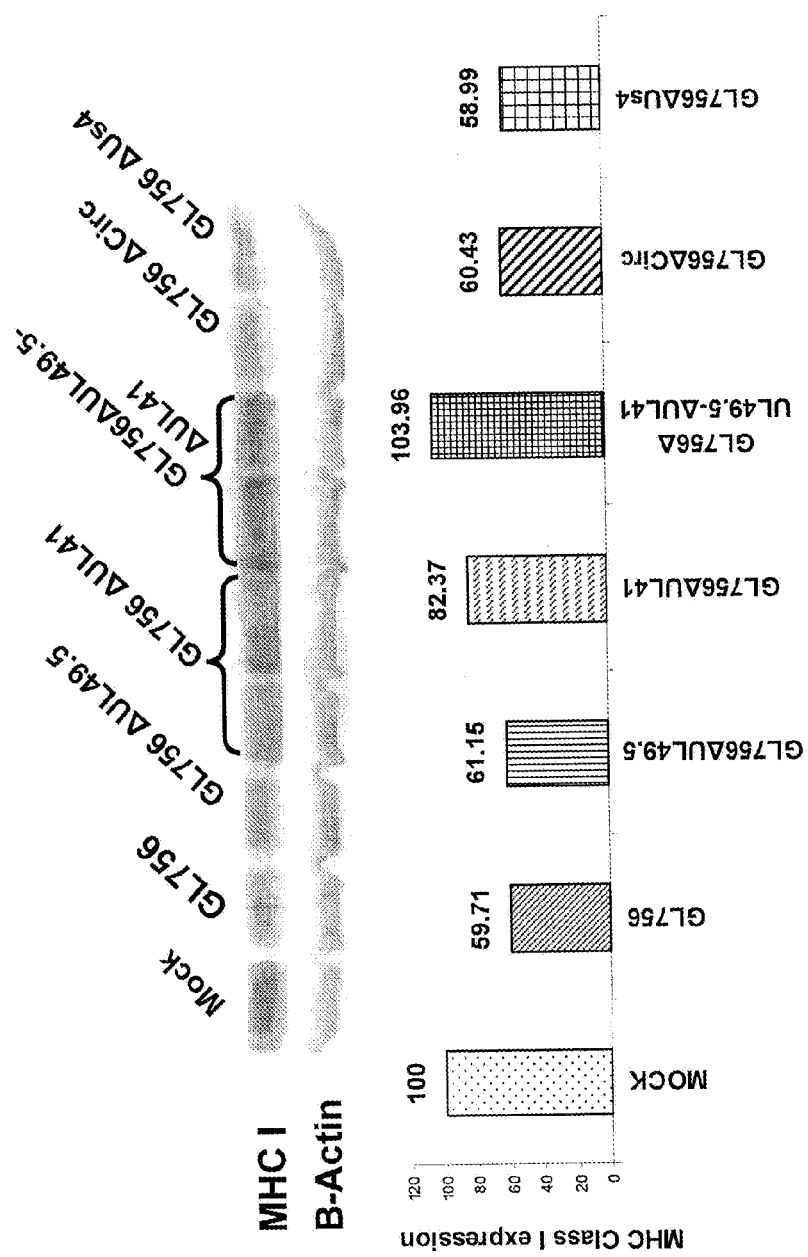

In addition to flow cytometry analysis of cell surface expression of MHC class I, lysates were prepared from cells infected as described above and were analyzed by SDS-PAGE and Western blotting using antibody reactive with MHC class II molecules. FIG. 27 (top) shows this analysis for cells infected with BHV-1 virus not containing modification (GL756), BHV-1 virus containing modification in UL49.5 (GL756 ΔUL49.5), two BHV-1 virus clones containing modification in UL41 (GL756 ΔUL41), two BHV-1 virus clones containing modifications in both UL49.5 and UL41 (GL756 ΔUL49.5-ΔUL41), BHV-1 virus containing modification in Circ (GL756 ΔCirc), and BHV-1 virus containing modification in Us4 (GL756 ΔUs4). These are the mutant BHV-1 viruses described in Example 6. FIG. 27 (bottom) shows densitometric quantification of the Western blots.

The data in FIG. 27 showed that, for BHV-1 viruses containing a modification in a single gene, BHV-1 with modified UL41 had the largest effect on restoration (least effect on suppression) of MHC class I expression as compared to BHV-1 not containing a modification. The data also showed that BHV-1 containing modifications in both UL49.5 and UL41 completely restored (had no effect on) MHC class I expression as compared to BHV-1 not containing a modification. The data showed that the modified BHV-1, GL756 ΔUL49.5-ΔUL41, may have even enhanced MHC class I expression as compared to mock infected cells.

Example 9

BHV-1 Down Regulation of MHC Class II Molecules on Infected Cells and Restoration of Class II expression by BHV-1 Viruses Containing Modifications To evaluate the effect of BHV-1 viruses and BHV-1 viruses containing modifications on expression of MHC class II molecules on the surface of infected cells, MDBK cells were infected with the modified BHV-1 viruses described in Example 6. Cells were infected with the viruses at an moi of 0.1, or were mock infected, incubated at 4'C for 30 mins, then at 37"C for 1 hour followed by IFN-γ treatment. At 72 hours post-infection, the cells were stained with monoclonal antibody CAT82A, specific for MHC class II molecules (VMRD). The CAT82A antibody was either labeled with Zenon® Mouse IgG Labeling Kits (Molecular Probes, Invitrogen Detection Technologies, Carlsbad, Calif., USA) or fluorescently labeled secondary antibodies were used. Negative control cells were unstained. The cells were then analyzed for fluorescence by flow cytometry.

Figure 28:
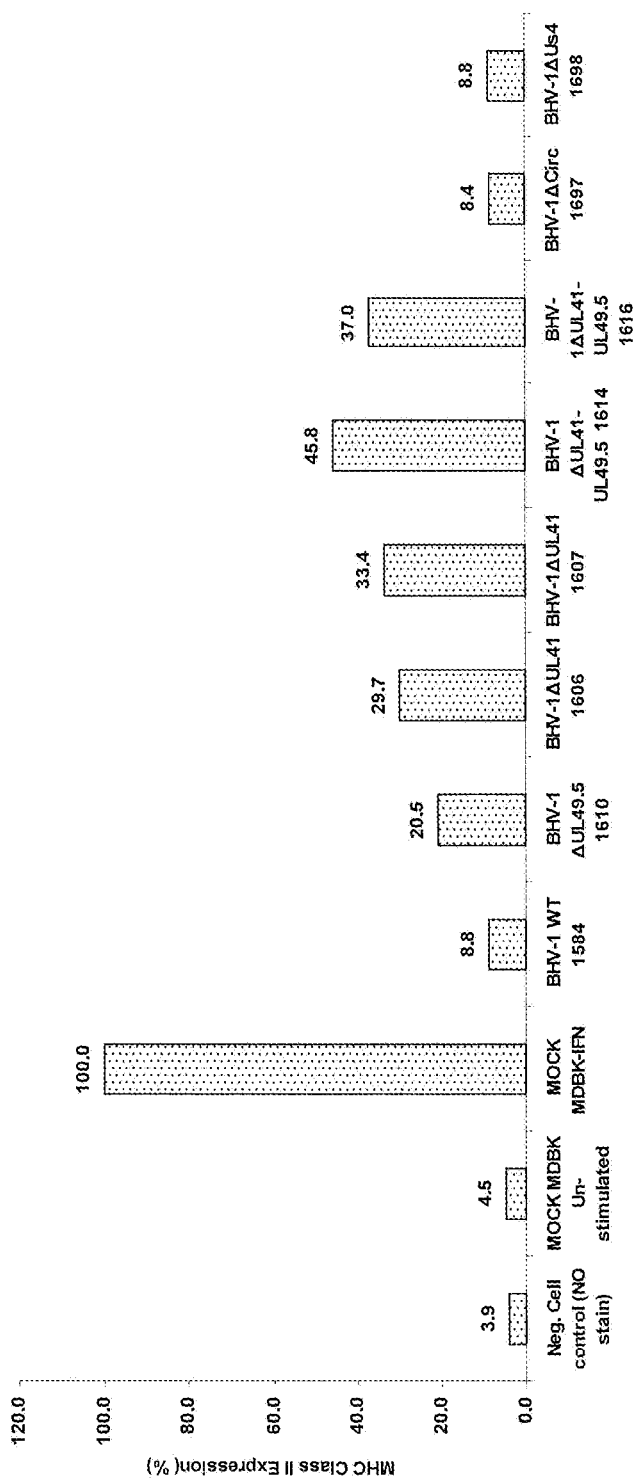
Figure 29:
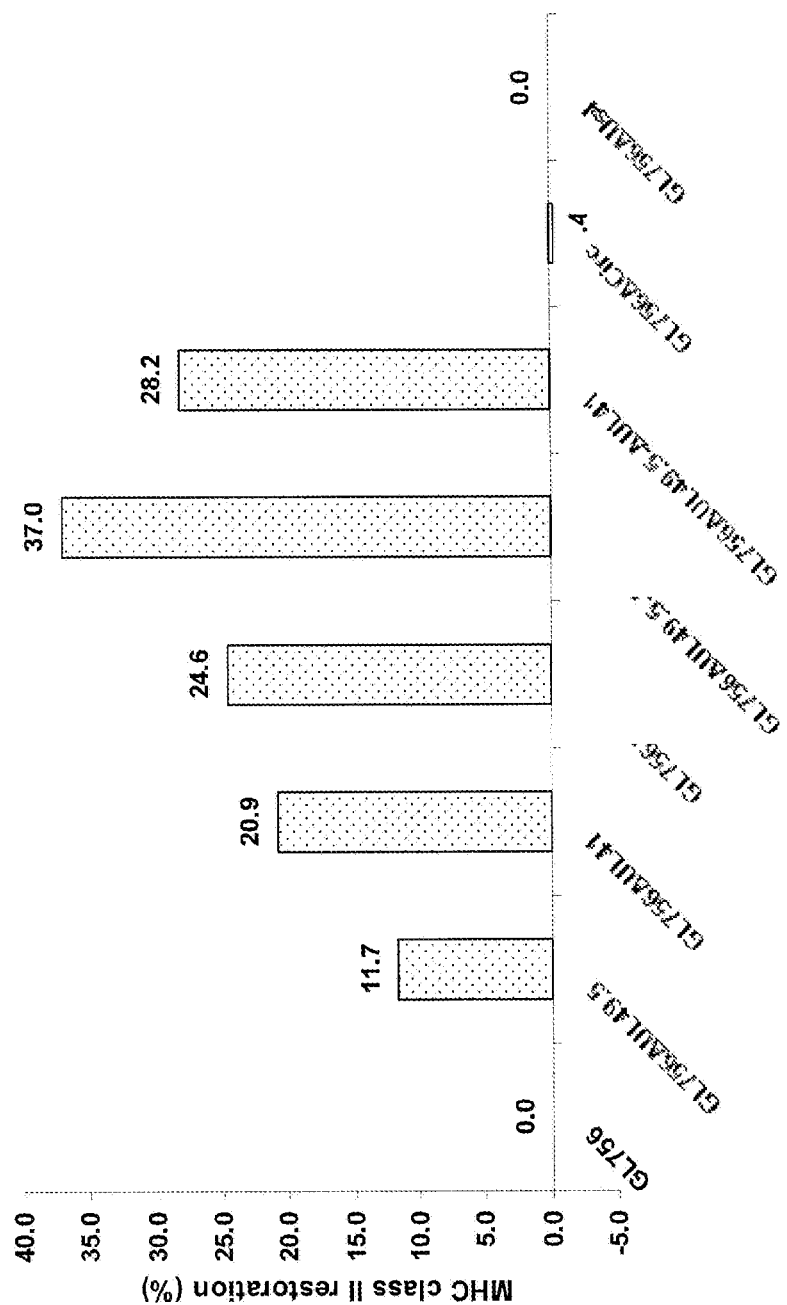

The data in FIG. 28 showed relative MHC class II expression in virus infected cells as compared to mock infected cells (mock infected cells indicated as 100% expression). The data in FIG. 29 showed percent restoration of MHC class II expression in cells by the viruses containing modifications as compared to cells infected with virus not containing modified genes (MHC class II levels in cells infected with BHV-1 GL756 given value of 0; mock infected cells have value of 100). The data showed that unmodified BHV-1 causes suppression of MHC class II molecule expression on the surface of infected cells. The data showed that BHV-1 viruses with modification in UL49.4, and BHV-1 viruses with modification in UL41, partially restored MHC class II expression (didn't suppress as significantly) as compared to unmodified or wild-type BHV-1. The data showed that BHV-1 viruses with modifications in both UL49.5 and UL41 suppressed MHC class II expression on infected cells less than viruses containing the single modifications (greater restoration of MHC class II as compared to BHV-1 containing modifications in single genes).

Example 10

Restoration and Enhancement of IgG1/IgG2 Subtype Ratio in Calves for IgG Specific to a Co-Administered Immunogen by BHV-1 Viruses Containing Modifications The data presented in Example 3 and FIG. 12 indicated that BHV-1 decreased the IgG1/IgG2 subtype ratio for IgG elicited, in response to an immunogen that is administered with BHV-1, as compared to the IgG1/IgG2 ratio for IgG elicited in response to an immunogen that was administered alone. To evaluate the effect of BHV-1 viruses containing modifications on the IgG1/IgG2 ratio for IgG reactive to an immunogen in administered with the virus, BHV-1 sero-negative calves (Hereford-Angus or Holstein-Dairy cross), 3-6 months of age, were used. The calves also had minimal amounts of LkT titers as measured by ELISA. Calves were subcutaneously administered in the neck either recombinant LkT from *Mannheimia haemolytica* alone (100 µg in 2 ml containing Emulsigen D adjuvant), LkT and BHV-1 GL756 (approximately $10^{5.5}$ BHV-1 GL756 strain in 2 ml), LkT and BHV-1 containing modifications in both UL49.5 and UL41 (GL756 ΔUL49.5-ΔUL41 as described in Example 6), or LkT and BHV-1 containing a modification in Us4 (GL756 ΔUs4 as described in Example 6). BHV-1, or modified BHV-1, and LkT were co-administered approximately 5 cm apart on day 0. LkT was administered again to the calves alone (without virus) on day 21. Blood was drawn and sera collected on days 14, 21, 28 and 35. IgG1 and IgG2 serum antibodies reactive with LkT were measured for each time point using ELISA plates coated with LkT and IgG subtype-specific antibodies.

Figure 30:
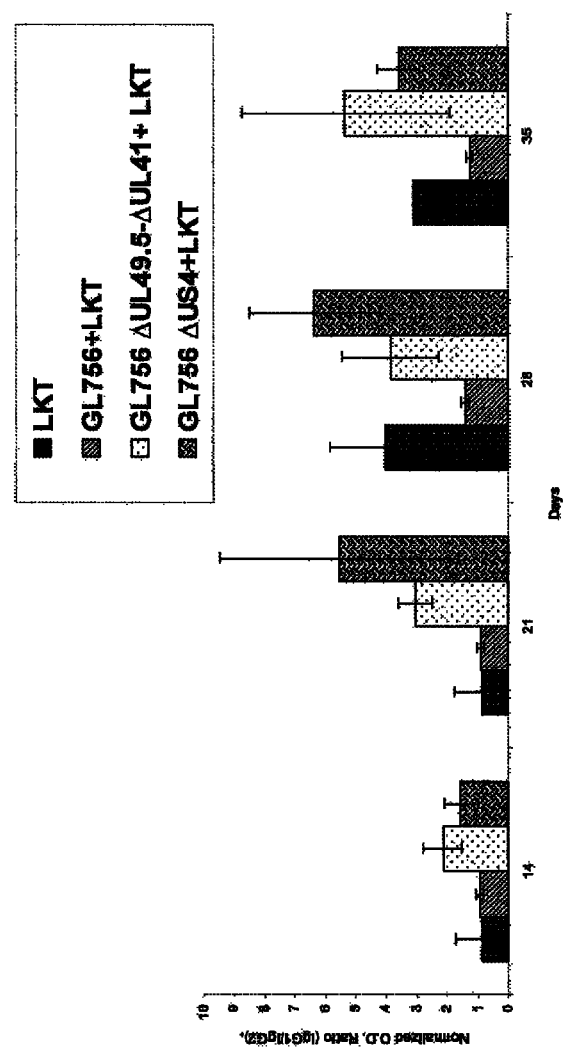

The results in FIG. 30 showed that administration of wild-type BHV-1 (GL756) along with LkT decreased the ratio of LkT-specific IgG1/IgG2 as compared to the ratio of LkT-specific IgG1/IgG2 obtained after administration of LkT alone (see 28 and 35 day time points). These results are the same as those discussed in Example 3 and illustrated in FIG. 12. The data in FIG. 30 also showed that this suppression of IgG1/IgG2 was not observed when LkT was administered with BHV-1 viruses that had modifications in both UL49.5 and UL41, or BHV-1 viruses that had modifications in Us4. The data showed that, in contrast to the suppression of the LkT-specific IgG1/IgG2 ratio seen after administration of LkT with wild-type BHV-1 (as compared to LkT alone), the LkT-specific IgG1/IgG2 ratio seen after administration of LkT with either of the two modified BHV-1 viruses was enhanced (greater than the IgG1/IgG2 seen after administration of LkT alone). These data indicated that the modified BHV-1 viruses could reverse the suppression of the IgG1/IgG2 ratio for antibodies specific for an immunogen co-administered immunogen with wild-type BHV-1. These data also indicated that the modified BHV-1 viruses could even enhance the IgG1/IgG2 ratio for antibodies specific for a co-administered immunogen, as compared to the IgG1/IgG2 ratio for the antibodies elicited after administration of the immunogen alone (without wild-type BHV-1).

Example 11

Restoration of Antigen Recall Response to a Co-Administered Immunogen in Calves by BHV-1 Viruses Containing Modifications The data presented in Example 4 and FIG. 14 indicated that BHV-1 could suppress a recall response to an immunogen co-administered with wild-type BHV-1, as compared to the recall response to the immunogen administered alone. To evaluate the effect of BHV-1 viruses containing modifications on the recall response to an immunogen administered with the virus, as measured by IL-2 production, blood was drawn from the calves used in the study described in Example 10 on day 23. The blood was diluted and LkT antigen was added to the samples. IL-2 levels were subsequently measured in the samples using ELISA.

Figure 31:
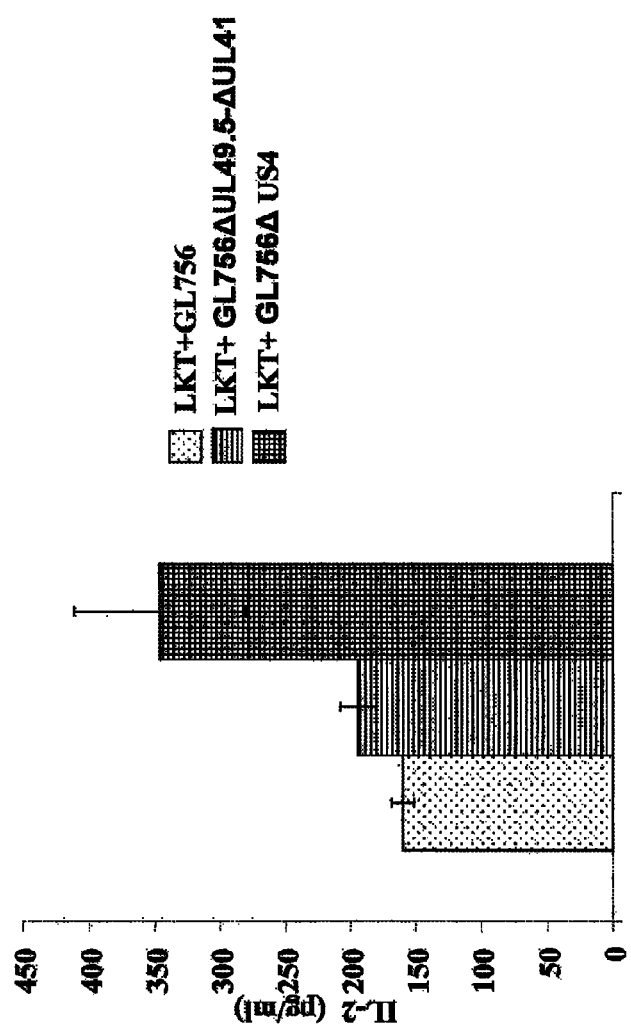

The results illustrated in FIG. 31 showed that antigen recall, as measured by IL-2 production from cells in the blood, was increased when LkT was administered to calves with BHV-1 virus containing modifications in both UL49.5 and UL41 (GL756ΔUL49.5-UL41 as described in Example 6) as compared to LkT administered to calves with BHV-1 that did not contain the modifications (GL756). The data showed that antigen recall was further increased when LkT was administered to calves with BHV-1 containing a modification in Us4 (GL756ΔUs4 as described in Example 6).

While example compositions, methods, and so on have been illustrated by description, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the invention is not limited to the specific details and examples shown and described. Thus, this application is intended, to embrace alterations, modifications, and variations that fall within the scope of the application. Furthermore, the preceding description is not meant to limit the scope of the invention. Rather, the scope of the invention is to be determined by the appended claims and their equivalents. To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive.

The invention claimed is:

1. A composition, comprising:
   a) a live BHV-1 that has modifications of UL49.5 and at least one additional gene encoding protein that can affect a host immunological response to an immunogen; and
   b) an additional immunogen which is not encoded by a foreign gene inserted in the genome of the live BHV-1, where following administration of the composition to a host, a ratio of IgG1/IgG2 for IgG specific for the additional immunogen in the host is higher than a ratio of IgG1/IgG2 for IgG specific for the additional immunogen in a host administered a composition of live BHV-1 that does not have the modifications and the additional immunogen.

2. The composition of claim 1, where the at least one additional gene is UL41 or Us4.

3. The composition of claim 1, where following administration of the composition of live BHV-1 that has the modifications and the additional immunogen to the host, cell samples obtained from blood of the host and contacted with the additional immunogen have higher levels of interleukin-2 (IL-2) as compared to levels of IL-2 from cell samples obtained from blood of the host administered the composition of live BHV-1 that does not have the modifications and the additional immunogen, and contacted with the additional immunogen.

4. The composition of claim 3, where the at least one additional gene is UL41.

5. The composition of claim 1, where the additional immunogen includes a bacterial, viral or parasitic immunogen.

6. The composition of claim 1, where the additional immunogen includes an immunogen from Bovine Viral Diarrhea Virus (BVDV) I, BVDV II, BVDV III, Bovine Respiratory Syncytial Virus (BRSV), Parainfluenza 3 Virus (PI3), *Rotavirus* (BRV), *Coronavirus* (BCV), *Mannheimia haemolytica*, *Histophilus somni*, *Mycoplasma bovis*, *Leptospira* species, *Vibrio* species, *Clostridia* species, *Pasteurella multocida*, *Fusobacterium necrophorum*, *E. coli* O157:H7, *Salmonella enterica*, *Neospora caninum* or *Trichomonas* species.

7. The composition of claim 1, where the additional immunogen includes LkT from *Mannheimia haemolytica*.

8. A method for eliciting an immunological response in a host, comprising administering to the host a composition including:
   a) an immunogen other than a BHV-1 antigen (non-BHV-1 immunogen), which is not encoded by a foreign gene inserted in a BHV-1 genome; and
   b) a live BHV-1 that has modifications of UL49.5 and at least one additional gene encoding protein that can affect a host immunological response to an immunogen, where following administration of the composition to the host, a ratio of IgG1 to IgG2 in the host for IgG specific for the non-BHV-1 immunogen is higher than a ratio of IgG1 to IgG2 for IgG specific for the non-BHV-1 immunogen in a host administered a composition of the non-BHV-1 immunogen and live BHV-1 that does not have the modifications.

9. The method of claim 8, where the non-BHV-1 immunogen and the live BHV-1 are co-administered or administered to the host in a combination vaccine.

10. The method of claim 8, where the at least one additional gene is UL41 or Us4.

11. The method of claim 8, where following administration of the composition of non-BHV-1 immunogen and live BHV-1 that has the modifications to the host, cell samples obtained from blood of the host and contacted with the non-BHV-1 immunogen have higher levels of interleukin-2 (IL-2) as compared to levels of IL-2 from cell samples obtained from blood of the host administered the composition of the non-BHV-1 immunogen and live BHV-1 that does not have the modifications, and contacted with the non-BHV-1 immunogen.

12. The method of claim 11, where the at least one additional gene is UL41.

13. The method of claim 8, wherein the host is an ungulate.

\* \* \* \* \*

UNITED STATES PATENT AND TRADEMARK OFFICE
CERTIFICATE OF CORRECTION

PATENT NO. : 8,637,046 B2  Page 1 of 1
APPLICATION NO. : 13/121566
DATED : January 28, 2014
INVENTOR(S) : Osterrieder et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 382 days.

Signed and Sealed this
Twenty-second Day of September, 2015

Michelle K. Lee
*Director of the United States Patent and Trademark Office*